United States Patent
An

(10) Patent No.: US 9,556,144 B2
(45) Date of Patent: *Jan. 31, 2017

(54) COMPOUND AS WNT SIGNALING INHIBITOR, COMPOSITION, AND USE THEREOF

(75) Inventor: Songzhu An, Gunagdong (CN)

(73) Assignee: CUREGENIX, INC., Guangzhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 14/408,254

(22) PCT Filed: Jun. 15, 2012

(86) PCT No.: PCT/CN2012/077032
§ 371 (c)(1),
(2), (4) Date: Dec. 15, 2014

(87) PCT Pub. No.: WO2013/185353
PCT Pub. Date: Dec. 19, 2013

(65) Prior Publication Data
US 2015/0119387 A1 Apr. 30, 2015

(51) Int. Cl.
A61K 31/54 (2006.01)
A61K 31/50 (2006.01)
A61K 31/495 (2006.01)
A61K 31/4965 (2006.01)
A61K 31/44 (2006.01)
A61K 31/501 (2006.01)
A61K 31/497 (2006.01)
A61K 31/47 (2006.01)
C07D 217/00 (2006.01)
C07D 217/22 (2006.01)
C07D 471/02 (2006.01)
C07D 471/00 (2006.01)
C07D 491/00 (2006.01)
C07D 487/00 (2006.01)
C07D 495/00 (2006.01)
C07D 497/00 (2006.01)
C07D 401/00 (2006.01)
C07D 403/00 (2006.01)
C07D 405/00 (2006.01)
C07D 409/00 (2006.01)
C07D 411/00 (2006.01)
C07D 413/00 (2006.01)
C07D 417/00 (2006.01)
C07D 419/00 (2006.01)
C07D 401/14 (2006.01)
C07D 401/12 (2006.01)
C07D 471/04 (2006.01)

(52) U.S. Cl.
CPC ........ C07D 401/14 (2013.01); C07D 217/22 (2013.01); C07D 401/12 (2013.01); C07D 471/04 (2013.01)

(58) Field of Classification Search
None
See application file for complete search history.

(56) References Cited

FOREIGN PATENT DOCUMENTS

| CN | 102558173 A | 7/2012 |
| WO | WO 2004/043925 A2 * | 5/2004 |
| WO | WO2004043925 | 5/2004 |
| WO | WO 2006/074428 A2 * | 7/2006 |
| WO | WO2007076092 | 7/2007 |
| WO | 2008/086462 A2 | 7/2008 |
| WO | 2012/003189 A1 | 1/2012 |
| WO | WO2013185353 | 12/2013 |

OTHER PUBLICATIONS

CAS Registry database, No. 5565053-76-0. Entered Jul. 28, 2003.*
CAS Registry No. 679000-13-6, entered in STN May 3, 2004.*
Registry RN 556053-76-0, entered STN Jul. 28, 2003.
Tropsha, Alexander et al. Development of kNN QSAR models for 3-arylisoquinoline antitumor agents. Bull. Korean Chem. Soc. 2011, 32(7): 2397-2404.
International Search report and written opinion for PCT/CN2012/077032.
File Registry [Online]; Jun. 5, 2011, registry No. 1305542-20-4.
File Registry [Online]; Sep. 13, 2009, registry No. 1183116-75-7.
File Registry [Online]; Jun. 8 2009, registry No. 1153789-26-4.
File Registry [Online]; Apr. 22, 2011, registry No. 1284058-56-5.
File Registry [Online]; Jun. 9, 2011, registry No. 1308218-48-5.
Lanier et al., Wnt inhibition correlates with human embryonic stem cell cardiomyogenesis: a structure-activity relationship study based on inhibitors for the Wnt response. Journal of Medicinal Chemistry, 55(2):697-708 (2012).
Supplementary European Search Report completed on Nov. 19, 2015, for European Patent Application No. 12878945.0 filed on Jun. 15, 2012.

* cited by examiner

Primary Examiner — Noble Jarrell
Assistant Examiner — Ben S Michelson
(74) Attorney, Agent, or Firm — K&L Gates LLP; Brent A. Johnson; Louis C. Cullman

(57) ABSTRACT

The present invention relates to a compound having the structure of Formula I as inhibitor of WNT signal transduction pathways, as well as a composition comprising the compound. Further, the present invention relates to the use of the compound and the method of inhibiting the WNT signal transduction pathways.

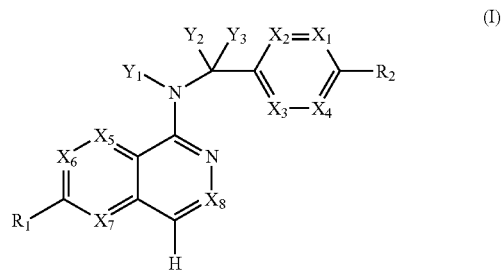

(I)

19 Claims, No Drawings

COMPOUND AS WNT SIGNALING INHIBITOR, COMPOSITION, AND USE THEREOF

FIELD OF THE INVENTION

The present invention relates to a compound as inhibitor of WNT signal transduction pathway, as well as a composition comprising the same. Further, the present invention relates to the use of the compound and the method of inhibiting the WNT signal transduction pathway.

BACKGROUND OF THE INVENTION

WNT signaling is important to both embryogenesis and homeostasis in adult animals. The WNT pathway is comprised in general of a network of proteins that regulate the following processes: 1, the production and secretion of WNT proteins; 2, the binding of WNT with cellular receptors; and 3, the intracellular transduction of the biochemical responses triggered by the interaction (Mikels and Nusse, 2006; MacDonald, 2009; Moon, 2005).

The so-called canonical WNT pathway triggered by binding of WNT proteins to cell surface co-receptors Frizzled LRP5/6 results in a change in the amount of β-catenin that reaches the nucleus where it interacts with TCF/LEF family transcription factors to promote transcription of specific genes.

The non-canonical WNT pathway transduced by a different set of intracellular proteins controls planar cell polarity in insects and several processes such as gastrulation in vertebrates.

WNT signaling is also known for its roles in controlling pluripotency and differentiation of embryonic and adult stem cells (Nusse, 2008). For example, formation of the primitive streak during gastrulation was associated with localized WNT activation in the embryoid bodies (ten Berge, 2008). The derivation of a number of cell types, such as heart cells, pancreatic beta cells, dopminergic neurons and liver hepatocytes from embryonic stem cells or iPS cells is influenced by WNT modulation (Yang, 2008; D'Amour, 2006; Inestrosa and Arenas, 2010; Sullivan, 2010). The WNT pathway plays a particularly important role in skeletal tissue development such as osteogenesis and chondrogenesis (Hoeppner, 2009; Chun, 2008). WNT signaling is also associated with neuro-regeneration of the adult central nervous system (Lie, 2005).

Diseases may arise from altered WNT pathway activity. For example, hyperactivation of the canonical WNT pathway can lead to aberrant cell growth (Reya and Clevers, 2005). Notably, 90% of colorectal cancers are initiated by the loss of the adenomatosis polyposis *coli* (APC) gene, a suppressor of the WNT/β-catenin pathway (Kinzler and Vogelstein, 1996). Increased expression of WNT proteins and loss of extracellular inhibitors that normally suppress WNT protein function may give rise to WNT-dependent tumors (Polakis, 2007). On the other hand, the non-canonical WNT pathway has also been shown to play a role in the progression of certain cancers (Camilli and Weeraratna, 2010). More recently, WNT signaling is also implicated in cancer stem cells (Takahashi-Yanaga and Kahn, 2010).

Evidence suggests that targeting the Wnt-mediated signal transduction pathway would be therapeutically useful in a broad range of diseases (Barker and Clevers, 2006). Mutations of APC, beta-catenin or axin-1 leading to constitutive activation of the canonical Wnt pathway are critical events in a variety of human cancers including colorectal cancer, melanoma, hepatocellular carcinoma, gastric cancer, ovarian cancer and others (Polakis, 2007). Blockade of the Wnt pathway in a variety of cancers using either genetic or chemical approaches has been shown to abrogate aberrant cell growth (Herbst and Kolligs, 2007). Furthermore, inhibition of this pathway may directly influence the cells that sustain cancer cell growth and enable metastasis, and that are thought to be resistant to traditional chemotherapeutic agents.

In addition to activation caused by mutations of gene products downstream of the receptors, aberrant Wnt pathway activity caused by other mechanisms have been associated with a broad range of cancers. These cancers include but not limited to: lung (small cell and non-small cell), breast, prostate, carcinoid, bladder, scarcinoma, esophageal, ovarian, cervical, endometrial, mesothelioma, melanoma, sarcoma, osteosarcoma, liposarcoma, thyroid, desmoids, chronic myelocytic leukemia (AML), and chronic myelocytic leukemia (CML). There are now multiple examples of cancer cells dependent upon upregulated autocrine or paracrine Wnt signaling, and cell lines from osteosarcoma, breast, head and neck and ovarian cancers have been shown to derive protection from apoptosis by autocrine or paracrine Wnt signaling (Kansara, 2009; Bafico, 2004; Akiri, 2009; DeAlmeida, 2007; Chan, 2007; Chen, 2009; Rhee, 2002).

Furthermore, aberrant Wnt pathway has been implicated in the development of fibrosis, include but are not limited to: lung fibrosis, such as idiopathic pulmonary fibrosis and radiation-induced fibrosis, renal fibrosis and liver fibrosis (Morrisey, 2003; Hwang, 2009; Cheng, 2008).

Other disorders associated with aberrant WNT signaling, include but are not limited to bone and cartilage disorders, such as osteoporosis and osteoarthritis, obesity associated type II diabetes, and neurodegenerative diseases such as Alzheimer's disease (Hoeppner, 2009; Ouchi, 2010; Blom, 2010; Boonen, 2009). WNT signaling also contributes to the self-renewal and maintenance of HSC's, and dysfunctional WNT signaling is responsible for various disorders resulting from HSC's, such as leukemias and various other blood related cancers (Reya, 2005).

Accordingly, identification of methods and compounds that modulate the WNT-dependent cellular responses may offer an avenue for regulating physiological functions and therapeutic treatment of diseases associated with aberrant activity of the pathways.

SUMMARY OF THE INVENTION

The present invention generally provides a compound and a pharmaceutical composition thereof, while the compound is used as WNT signaling inhibitor, and the use of such compound for inhibiting WNT signaling pathway.

DEFINITION

As used herein, "WNT signaling pathway" or "WNT pathway" refers to the pathway by which binding of the WNT protein to cellular receptors results in changes of cell behavior. The WNT pathway involves a variety of proteins including Frizzled, Disheveled, Axin, APC, GSK3β, β-catenin, LEF/TCF transcription factors, and molecules involved in the synthesis and secretion of WNT proteins. Examples of proteins implicated in the secretion of functional WNTs include, but are not limited to wntless/evenness interrupted (Wls/Evi), porcupine (Porcn), and Vps35p. Wls/Evi is a 7 pass transmembrane protein which resides in the Golgi apparatus and is required for secretion of Wg (*drosophila*) MOM-2 (*C. elegans*) and Wnt3A. It contains a conserved structural motif whose structure and function are both unknown. Porcupine (Porcn) is a member of the membrane-bound O-acyltransferase (MBOAT) family of palmitoyl transferases. Fatty acid modification of Wnts is critical for their function. Wnts are palmitoylated on one or two highly conserved sites. Inhibitors of Porcn may therefore block all functional Wnt signaling. Vps35p is a subunit of a multiprotein complex called the retromer complex which is involved in intracellular protein trafficking. Vps35p functions in binding target proteins like WNTs for recruitment into vesicles.

"WNT pathway inhibitor" or "WNT signaling inhibitor" is a small organic molecule that inhibits WNT signaling activity and typically has a molecular weight of about 800 g/mol or less.

The term "a method of inhibiting WNT pathway" refers to methods of inhibiting known biochemical events associated with production of functional WNT proteins or with cellular responses to WNT proteins. As discussed herein, small organic molecules may inhibit WNT response in accordance with this definition.

"WNT protein" is a protein binds to Frizzled and LRP5/6 co-receptors so as to activate canonical or non-canonical WNT signaling. Specific examples of WNT proteins include: WNT-1 (NM005430), WNT-2 (NM003391), WNT-2B/WNT-13 (NM004185), WNT-3 (NM030753), WNT3a (NM033131), WNT-4 (NM030761), WNT-5A (NM003392), WNT-5B (NM032642), WNT-6 (NM006522), WNT-7A (NM004625), WNT-7B (NM058238), WNT-8A (NM058244), WNT-8B (NM003393), WNT-9A/WNT-14) (NM003395), WNT-9B/WNT-15 (NM003396), WNT-10A (NM025216), WNT-10B (NM003394), WNT-11 (NM004626), WNT-16 (NM016087).

"WNT pathway disorder" is a condition or disease state with aberrant WNT signaling. In one aspect, the aberrant WNT signaling is a level of WNT signaling in a cell or tissue suspected of being diseased that exceeds the level of WNT signaling in a normal cell or tissue. In one specific aspect, a WNT-mediated disorder includes cancer or fibrosis.

The term "cancer" refers to the pathological condition in humans that is characterized by unregulated cell proliferation. Examples include but are not limited to: carcinoma, lymphoma, blastoma, and leukemia. More particular examples of cancers include but are not limited to: lung (small cell and non-small cell), breast, prostate, carcinoid, bladder, gastric, pancreatic, liver (hepatocellular), hepatoblastoma, colorectal, head and neck squamous cell carcinoma, esophageal, ovarian, cervical, endometrial, mesothelioma, melanoma, sarcoma, osteosarcoma, liposarcoma, thyroid, desmoids, chronic myelocytic leukemia (AML), and chronic myelocytic leukemia (CML).

The term "fibrosis" refers to the pathological condition in humans that is typically characterized by uncontrolled proliferation of fibroblast cells and tissue hardening. Specific examples include but not limited to: lung fibrosis (idiopathic pulmonary fibrosis and radiation-induced fibrosis), renal fibrosis and liver fibrosis including liver cirrhosis.

"Inhibiting" or "treating" or "treatment" refers to reduction, therapeutic treatment and prophylactic or preventative treatment, wherein the objective is to reduce or prevent the aimed pathologic disorder or condition. In one example, following administering of a WNT signaling inhibitor, a cancer patient may experience a reduction in tumor size. "Treatment" or "treating" includes (1) inhibiting a disease in a subject experiencing or displaying the pathology or symptoms of the disease, (2) ameliorating a disease in a subject that is experiencing or displaying the pathology or symptoms of the disease, and/or (3) affecting any measurable decrease in a disease in a subject or patient that is experiencing or displaying the pathology or symptoms of the disease. To the extent the WNT pathway inhibitor may prevent growth and/or kill cancer cells, it may be cytostatic and/or cytotoxic.

The term "therapeutically effective amount" refers to an amount of a WNT pathway inhibitor effective to "treat" a WNT pathway disorder in a subject or mammal. In the case of cancer, the therapeutically effective amount of the drug may either reduce the number of cancer cells, reduce the tumor size, inhibit cancer cell infiltration into peripheral organs, inhibit tumor metastasis, inhibit tumor growth to certain extent, and/or relieve one or more of the symptoms associated with the cancer to some extent.

Administration "in combination with" one or more further therapeutic agents includes simultaneous (concurrent) and consecutive administration in any order. As used herein, the term "pharmaceutical combination" refers to a product obtained from mixing or combining active ingredients, and includes both fixed and non-fixed combinations of the active ingredients. The term "fixed combination" means that the active ingredients, e.g. a compound of Formula (1) and a co-agent, are both administered to a patient simultaneously in the form of a single entity or dosage. The term "non-fixed combination" means that the active ingredients, e.g. a compound of Formula (1) and a co-agent, are both administered to a patient as separate entities either simultaneously, concurrently or sequentially with no specific time limits, wherein such administration provides therapeutically effective levels of the active ingredients in the body of the patient. The latter also applies to cocktail therapy, e.g. the administration of three or more active ingredients.

A "chemotherapeutic agent" is a chemical compound useful in the treatment of cancer. Examples are but not limited to: Gemcitabine, Irinotecan, Doxorubicin, 5-Fluorouracil, Cytosine arabinoside ("Ara-C"), Cyclophosphamide, Thiotepa, Busulfan, Cytoxin, TAXOL, Methotrexate, Cisplatin, Melphalan, Vinblastine and Carboplatin.

DESCRIPTION OF THE INVENTION

In one aspect, the present invention provides a compound as WNT signaling inhibitor, which has the structure of Formula I:

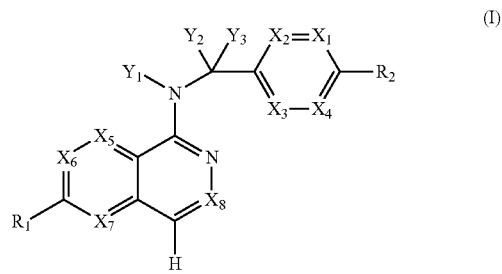

or a physiologically acceptable salt thereof,
wherein,
$X_1, X_2, X_3, X_4, X_5, X_6, X_7$ and $X_8$ are independently $CR_4$ or N;
$Y_1$ is hydrogen or —$C(R_4)_3$, each $R_4$ is same or different;
$Y_2$ and $Y_3$ are independently hydrogen, halogen or —$C(R_3)_3$, each $R_3$ is same or different;

$R_1$ and $R_2$ are independently selected from hydrogen, halogen, $C_{1-6}$ alkyl, quinolinyl,

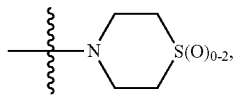

$C_{6-30}$ aryl, 3 to 6 membered heterocycloalkyl containing 1-2 heteroatoms selected from N, O and S, and 5 or 6 membered heteroaryl containing 1-4 heteroatoms selected from N, O and S, wherein each of quinolinyl,

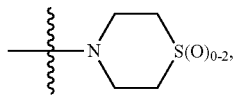

$C_{6-30}$ aryl, 3 to 6 membered heterocycloalkyl, and 5 or 6 membered heteroaryl can be optionally substituted with one or two, and same or different $R_4$;

each $R_3$ is independently selected from hydrogen, halogen, cyano, $C_{1-6}$ alkyl, and $C_{1-6}$ alkoxy, wherein each of the $C_{1-6}$ alkyl and $C_{1-6}$ alkoxy can be optionally substituted with halo, amino, hydroxyl, $C_{1-6}$ alkoxy or cyano;

each $R_4$ is independently selected from hydrogen, halogen, cyano, $C_{1-6}$ alkoxy, $-S(O)_2R_5$, $-C(O)OR_5$, $-C(O)R_5$, $-C(O)NR_6R_7$, $C_{1-6}$ alkyl, $C_{2-6}$ alkenyl and $C_{2-6}$ alkynyl, wherein each of $C_{1-6}$ alkoxy, $-S(O)_2R_5$, $-C(O)OR_5$, $-C(O)R_5$, $-C(O)NR_6R_7$, $C_{1-6}$ alkyl, $C_{2-6}$ alkenyl and $C_{2-6}$ alkynyl can be optionally substituted with halo, amino, hydroxyl, $C_{1-6}$ alkoxy or cyano; and $R_5$, $R_6$ and $R_7$ are independently selected from hydrogen, $C_{1-6}$ alkyl, $C_{2-6}$ alkenyl and $C_{2-6}$ alkynyl, in which each of the $C_{1-6}$ alkyl, $C_{2-6}$ alkenyl and $C_{2-6}$ alkynyl can be optionally substituted with halo, amino, hydroxyl, $C_{1-6}$ alkoxy or cyano.

In particular, Formula (I) represents the following core structures but not limited to:

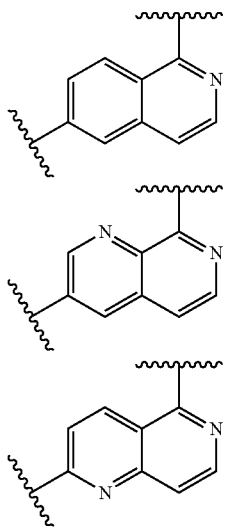
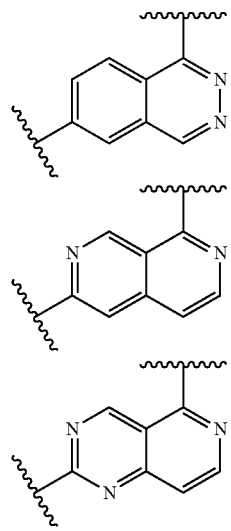
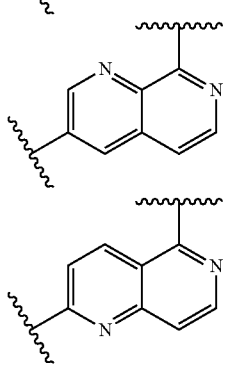
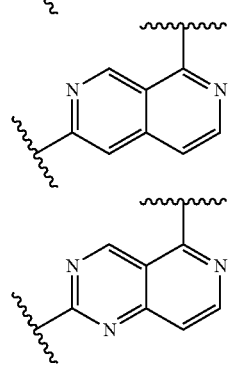

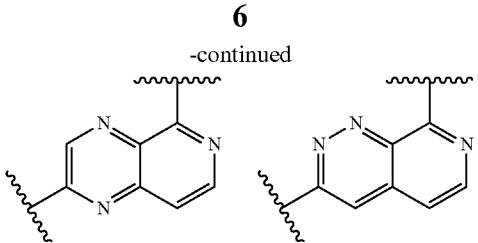

In Formula I, the ring defined by $X_1$, $X_2$, $X_3$ and $X_4$ may be any of the following groups but not limited to:

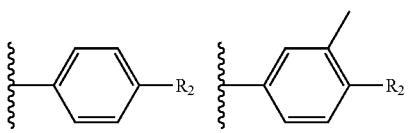
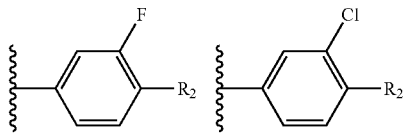
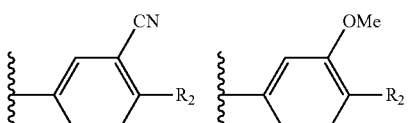
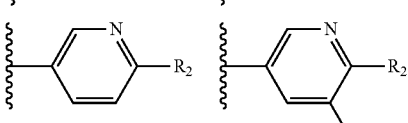
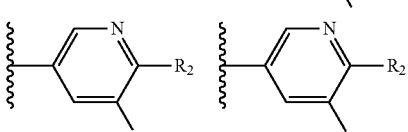
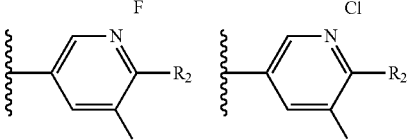
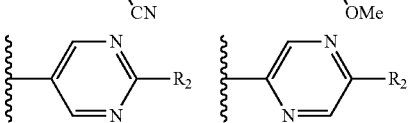
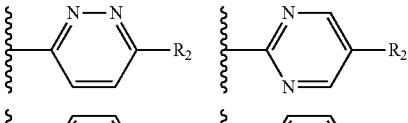
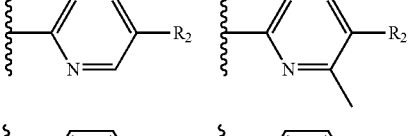
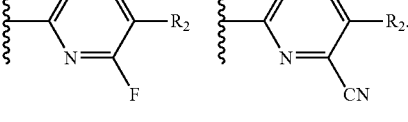

Preferably, $R_1$ and $R_2$ in Formula I may be independently selected from hydrogen, fluorine, chlorine, methyl,

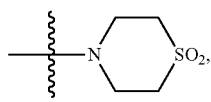

phenyl, morpholinyl, piperazinyl, and the 5 or 6 membered heteroaryl selected from:

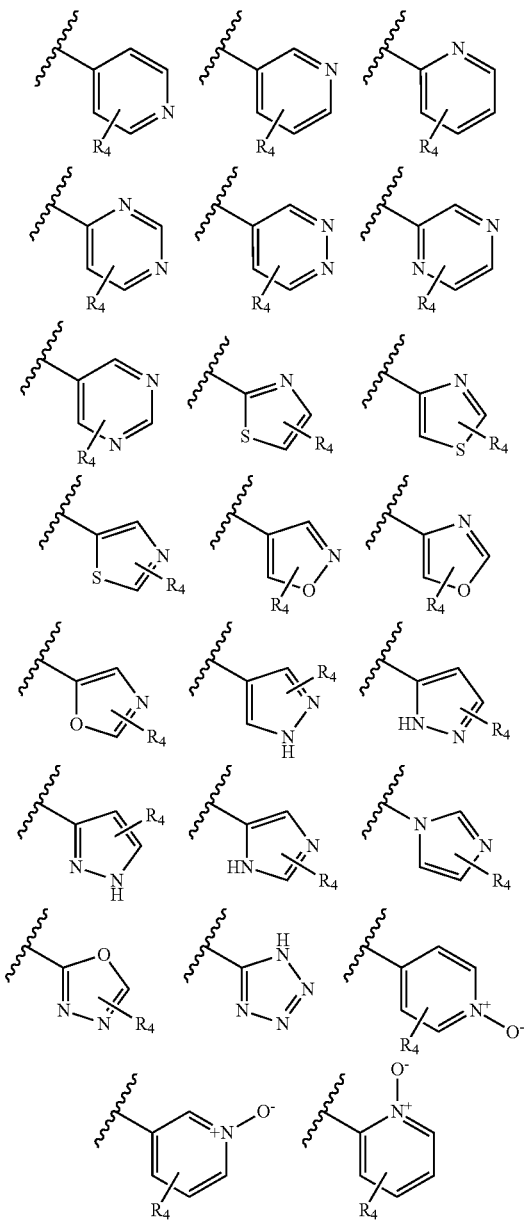

Preferably, $R_4$ may be same or different and each independently selected from hydrogen, chlorine, fluorine, cyano, —$CH_3$, —$CHF_2$, —$CF_3$, —$OCH_3$, —$COOCH_3$.

In one embodiment, at least one atom in Formula I is at least one of corresponding isotope(s) selected from $^2H$, $^3H$, $^{11}C$, $^{13}C$, $^{14}C$, $^{15}N$, $^{17}O$, $^{18}O$, $^{35}S$, $^{18}F$, $^{36}Cl$ and $^{123}I$.

As used herein, an H atom for example in any substituent groups (e.g., $CH_2$) encompasses all suitable isotopic variations, e.g., H, $^2H$ and $^3H$.

As used herein, other atoms for example in any substituent groups encompasses all suitable isotopic variations, including but not limited to $^{11}C$, $^{13}C$, $^{14}C$, $^{15}N$, $^{17}O$, $^{18}O$, $^{35}S$, $^{18}F$, $^{36}Cl$ and/or $^{123}I$.

In a preferred embodiment, example of the compound of the invention includes but is not limited to:
N-((6-(2-methylpyridin-4-yl)pyridin-3-yl)methyl)-7-phenylquinazolin-4-amine;
N-((5-(2-methylpyridin-4-yl)pyridin-2-yl)methyl)-7-phenylquinazolin-4-amine;
N-(4-morpholinobenzyl)-7-phenylquinazolin-4-amine;
N-((6-morpholinopyridin-3-yl)methyl)-7-phenylquinazolin-4-amine;
N-((6-(2-methylmorpholino)pyridin-3-yl)methyl)-7-phenylquinazolin-4-amine;
N-((6-(4-methylpiperazin-1-yl)pyridin-3-yl)methyl)-7-phenylquinazolin-4-amine;
4-(5-(((7-phenylquinazolin-4-yl)amino)methyl)pyridin-2-yl)thiomorpholine 1,1-dioxide;
N-((6-(6-methylpyridin-3-yl)pyridin-3-yl)methyl)-7-phenylquinazolin-4-amine;
N-((6-(5-methylpyridin-3-yl)pyridin-3-yl)methyl)-7-phenylquinazolin-4-amine;
7-phenyl-N-((6-(pyridin-4-yl)pyridin-3-yl)methyl)quinazolin-4-amine;
7-phenyl-N-((6-(pyridin-3-yl)pyridin-3-yl)methyl)quinazolin-4-amine;
7-phenyl-N-((6-(pyridin-2-yl)pyridin-3-yl)methyl)quinazolin-4-amine;
7-phenyl-N-((6-(pyridazin-4-yl)pyridin-3-yl)methyl)quinazolin-4-amine;
7-phenyl-N-((6-(pyrazin-2-pyridin-3-yl)methyl)quinazolin-4-amine;
7-phenyl-N-((6-(pyrimidin-5-yl)pyridin-3-yl)methyl)quinazolin-4-amine;
N-((6-(2-fluoropyridin-4-yl)pyridin-3-yl)methyl)-7-phenylquinazolin-4-amine;
N-((6-(4-methyl-1H-imidazol-1-yl)pyridin-3-yl)methyl)-7-phenylquinazolin-4-amine;
N-((6-(1-methyl-1H-pyrazol-4-yl)pyridin-3-yl)methyl)-7-phenylquinazolin-4-amine;
N-((5-(6-methylpyridin-3-yl)pyridin-2-yl)methyl)-7-phenylquinazolin-4-amine;
N-(4-(2-methylpyridin-4-yl)benzyl)-7-phenylquinazolin-4-amine;
N-(4-(2-fluoropyridin-4-yl)benzyl)-7-phenylquinazolin-4-amine;
N-benzyl-7-(2-methylpyridin-4-yl)quinazolin-4-amine;
N-(4-methylbenzyl)-7-(2-methylpyridin-4-yl)quinazolin-4-amine;
N-(4-methoxybenzyl)-7-(2-methylpyridin-4-yl)quinazolin-4-amine;
N-(4-fluorobenzyl)-7-(2-methylpyridin-4-yl)quinazolin-4-amine;
N-(4-chlorobenzyl)-7-(2-methylpyridin-4-yl)quinazolin-4-amine;
N-(4-bromobenzyl)-7-(2-methylpyridin-4-yl)quinazolin-4-amine;
N-(4-(trifluoromethyl)benzyl)-7-(2-methylpyridin-4-yl)quinazolin-4-amine;
4-((7-(2-methylpyridin-4-yl)quinazolin-4-ylamino)methyl)benzonitrile;
N-(4-morpholinobenzyl)-7-(2-methylpyridin-4-yl)quinazolin-4-amine;
N-(4-phenylbenzyl)-7-(2-methylpyridin-4-yl)quinazolin-4-amine;

N-(3-fluoro-4-phenylbenzyl)-7-(2-methylpyridin-4-yl)quinazolin-4-amine;
N-(4-(3-fluorophenyl)benzyl)-7-(2-methylpyridin-4-yl)quinazolin-4-amine;
7-(3-fluorophenyl)-N-((6-(2-methylpyridin-4-yl)pyridin-3-yl)methyl)quinazolin-4-amine;
7-(3-chlorophenyl)-N-((6-(2-methylpyridin-4-yl)pyridin-3-yl)methyl)quinazolin-4-amine;
N-((6-(2-methylpyridin-4-yl)pyridin-3-yl)methyl)-7-m-tolylquinazolin-4-amine;
3-(4-((6-(2-methylpyridin-4-yl)pyridin-3-yl)methylamino)quinazolin-7-yl)benzonitrile;
4-(4-((6-(2-methylpyridin-4-yl)pyridin-3-yl)methylamino)quinazolin-7-yl)benzonitrile;
7-(2-methylpyridin-4-yl)-N-((6-(2-methylpyridin-4-yl)pyridin-3-yl)methyl)quinazolin-4-amine;
7-(6-methylpyridin-3-yl)-N-((6-(2-methylpyridin-4-yl)pyridin-3-yl)methyl)quinazolin-4-amine;
7-(5-methylpyridin-3-yl)-N-((6-(2-methylpyridin-4-yl)pyridin-3-yl)methyl)quinazolin-4-amine;
N-((6-(2-methylpyridin-4-yl)pyridin-3-yl)methyl)-7-(pyridin-2-yl)quinazolin-4-amine;
N-((6-(2-methylpyridin-4-yl)pyridin-3-yl)methyl)-7-(pyridin-3-yl)quinazolin-4-amine;
N-((6-(2-methylpyridin-4-yl)pyridin-3-yl)methyl)-7-(pyridin-4-yl) quinazolin-4-amine;
N-((6-(2-methylpyridin-4-yl)pyridin-3-yl)methyl)-7-(pyridazin-4-yl)quinazolin-4-amine;
N-((6-(2-methylpyridin-4-yl)pyridin-3-yl)methyl)-7-(pyrazin-2-yl)quinazolin-4-amine;
N-((6-(2-methylpyridin-4-yl)pyridin-3-yl)methyl)-7-(pyrimidin-5-yl)quinazolin-4-amine;
7-(2-fluoropyridin-4-yl)-N-((6-(2-methylpyridin-4-yl)pyridin-3-yl)methyl)quinazolin-4-amine;
7-(2-(trifluoromethyl)pyridin-4-yl)-N-((6-(2-methylpyridin-4-yl)pyridin-3-yl)methyl)quinazolin-4-amine;
7-(2-methoxypyridin-4-yl)-N-((6-(2-methylpyridin-4-yl)pyridin-3-yl)methyl)quinazolin-4-amine;
7-(3-methylpyridin-4-yl)-N-((6-(2-methylpyridin-4-yl)pyridin-3-yl)methyl)quinazolin-4-amine;
N-((6-(2-methylpyridin-4-yl)pyridin-3-yl)methyl)-7-morpholinoquinazolin-4-amine;
N-((6-(2-methylpyridin-4-yl)pyridin-3-yl)methyl)-7-(piperidin-1-yl)quinazolin-4-amine;
7-(4-methylpiperazin-1-yl)-N-((6-(2-methylpyridin-4-yl)pyridin-3-yl)methyl)quinazolin-4-amine;
1-(4-(4-((6-(2-methylpyridin-4-yl)pyridin-3-yl)methylamino)quinazolin-7-yl)piperazin-1-yl)ethanone;
4-(4-(((2'-methyl-[2,4'-bipyridin]-5-yl)methyl)amino)quinazolin-7-yl)thiomorpholine1,1-dioxide;
7-(1,2,3,6-tetrahydropyridin-4-yl)-N-((6-(2-methylpyridin-4-yl)pyridin-3-yl)methyl)quinazolin-4-amine;
7-(1,2,3,6-tetrahydropyridin-4-yl)-N-((6-(2-methylpyridin-4-yl)pyridin-3-yl)methyl)quinazolin-4-amine;
1-(4-(4-((6-(2-methylpyridin-4-yl)pyridin-3-yl)methylamino)quinazolin-7-yl)piperidin-1-yl)ethanone;
N-((2'-methyl-[2,4'-bipyridin]-5-yl)methyl)-7-(4-(methylsulfonyl)piperazin-1-yl)quinazolin-4-amine;
7-(1-methyl-1H-pyrazol-4-yl)-N-((6-(2-methylpyridin-4-yl)pyridin-3-yl)methyl)quinazolin-4-amine;
7-(isoxazol-4-yl)-N-((6-(2-methylpyridin-4-yl)pyridin-3-yl)methyl)quinazolin-4-amine;
N-((6-(2-methylpyridin-4-yl)pyridin-3-yl)methyl)-7-(thiazol-2-yl)quinazolin-4-amine;
N-(3-methyl-4-(2-methylpyridin-4-yl)benzyl)-7-(2-methylpyridin-4-yl)quinazolin-4-amine;
N-(3-fluoro-4-(2-methylpyridin-4-yl)benzyl)-7-(2-methylpyridin-4-yl)quinazolin-4-amine;
N-(4-(2-methylpyridin-4-yl)benzyl)-7-(pyrazin-2-yl)quinazolin-4-amine;
N-(4-(2-methylpyridin-4-yl)benzyl)-7-(2-fluoropyridin-4-yl)quinazolin-4-amine;
N-(4-(2-methylpyridin-4-yl)benzyl)-7-morpholinoquinazolin-4-amine;
2-(3-fluorophenyl)-N-(4-(2-methylpyridin-4-yl)benzyl)pyrido[3,4-b]pyrazin-5-amine;
2-(3-fluorophenyl)-N-((2'-methyl-[2,4'-bipyridin]-5-yl)methyl)pyrido[3,4-b]pyrazin-5-amine;
2-(3-fluorophenyl)-N-(3-methyl-4-(2-methylpyridin-4-yl)benzyl)pyrido[3,4-b]pyrazin-5-amine;
N-(3-fluoro-4-(2-methylpyridin-4-yl)benzyl)-2-(3-fluorophenyl)pyrido[3,4-b]pyrazin-5-amine;
2-(2-methylpyridin-4-yl)-N-(4-(2-methylpyridin-4-yl)benzyl)pyrido[3,4-b]pyrazin-5-amine;
N-((2'-methyl-[2,4'-bipyridin]-5-yl)methyl)-2-(2-methylpyridin-4-yl)pyrido[3,4-b]pyrazin-5-amine;
N-(3-methyl-4-(2-methylpyridin-4-yl)benzyl)-2-(2-methylpyridin-4-yl)pyrido[3,4-b]pyrazin-5-amine;
N-(3-fluoro-4-(2-methylpyridin-4-yl)benzyl)-2-(2-methylpyridin-4-yl)pyrido[3,4-b]pyrazin-5-amine;
N-((2',3-dimethyl-[2,4'-bipyridin]-5-yl)methyl)-6-(pyrazin-2-yl)-2,7-naphthyridin-1-amine;
6-(2-methylmorpholino)-N-(4-(2-methylpyridin-4-yl)benzyl)-2,7-naphthyridin-1-amine;
(S)-6-(2-methylmorpholino)-N-(4-(2-methylpyridin-4-yl)benzyl)-2,7-naphthyridin-1-amine;
(R)-6-(2-methylmorpholino)-N-(4-(2-methylpyridin-4-yl)benzyl)-2,7-naphthyridin-1-amine;
1-(4-(8-((4-(2-methylpyridin-4-yl)benzyl)amino)-2,7-naphthyridin-3-yl)piperazin-1-yl)ethanone;
6-(1H-imidazol-1-yl)-N-(4-(2-methylpyridin-4-yl)benzyl)-2,7-naphthyridin-1-amine;
6-(4-methyl-1H-imidazol-1-yl)-N-(4-(2-methylpyridin-4-yl)benzyl)-2,7-naphthyridin-1-amine;
N-(4-(2-methylpyridin-4-yl)benzyl)-6-(1H-tetrazol-5-yl)-2,7-naphthyridin-1-amine;
6-(5-methyl-1,3,4-oxadiazol-2-yl)-N-(4-(2-methylpyridin-4-yl)benzyl)-2,7-naphthyridin-1-amine;
6-(1-methyl-1H-pyrazol-3-yl)-N-(4-(2-methylpyridin-4-yl)benzyl)-2,7-naphthyridin-1-amine;
N-(4-(2-methylpyridin-4-yl)benzyl)-6-(thiazol-5-yl)-2,7-naphthyridin-1-amine;
N-(4-(2-methylpyridin-4-yl)benzyl)-6-(oxazol-5-yl)-2,7-naphthyridin-1-amine;
N-((2',3-dimethyl-[2,4'-bipyridin]-5-yl)methyl)-6-(5-methylpyridin-3-yl)-2,7-naphthyridin-1-amine;
N-((2',3-dimethyl-[2,4'-bipyridin]-5-yl)methyl)-6-(2-methylpyridin-4-yl)-2,7-naphthyridin-1-amine;
N-((3-fluoro-2'-methyl-[2,4'-bipridin]-5-yl)methyl)-6-(2-methylpyridin-4-yl)-2,7-naphthyridin-1-amine;
N-((2',3-dimethyl-[2,4'-bipyridin]-5-yl)methyl)-6-(5-fluoropyridin-3-yl)-2,7-naphthyridin-1-amine;
N-(3-methyl-4-(2-methylpyridin-4-yl)benzyl)-6-(pyrazin-2-yl)-2,7-naphthyridin-1-amine;
N-(3-fluoro-4-(2-methylpyridin-4-yl)benzyl)-6-(pyrazin-2-yl)-2,7-naphthyridin-1-amine;
methyl-4-(8-((4-(2-methylpyridin-4-yl)benzyl)amino)-2,7-naphthyridin-3-yl)piperazine-1-carboxylate;
4-(8-((4-(2-methylpyridin-4-yl)benzyl)amino)-2,7-naphthyridin-3-yl)piperazin-2-one;
2-(4-(8-((4-(2-methylpyridin-4-yl)benzyl)amino)-2,7-naphthyridin-3-yl)piperazin-1-yl)acetonitrile;

2-methyl-4-(4-(((6-(2-methylpyridin-4-yl)-2,7-naphthyridin-1-yl)amino)methyl)phenyl)pyridine 1-oxide;
6-(2-chloropyridin-4-yl)-N-((2',3-dimethyl-[2,4'-bipyridin]-5-yl)methyl)-2,7-naphthyridin-1-amine;
6-(2-chloropyridin-4-yl)-N-(4-(2-methylpyridin-4-yl)benzyl)-2,7-naphthyridin-1-amine;
2'-methyl-4-(((6-(2-methylpyridin-4-yl)-2,7-naphthyridin-1-yl)amino)methyl)-2H-[1,4'-bipyridin]-2-one;
2-(2-methylpyridin-4-yl)-5-(((6-(2-methylpyridin-4-yl)-2,7-naphthyridin-1-yl)amino)methyl)benzonitrile;
N-(3-methoxy-4-(2-methylpyridin-4-yl)benzyl)-6-(2-methylpyridin-4-yl)-2,7-naphthyridin-1-amine;
N-((3-chloro-2'-methyl-[2,4'-bipyridin]-5-yl)methyl)-6-(2-methylpyridin-4-yl)-2,7-naphthyridin-1-amine;
N-(4-(2-(difluoromethyl)pyridin-4-yl)benzyl)-6-(2-methylpyridin-4-yl)-2,7-naphthyridin-1-amine;
or physiologically acceptable salts thereof.

In another aspect, the present invention provides a pharmaceutical composition comprising the compound of the present invention, and usually comprising at least one pharmaceutically acceptable carrier or diluent, in which said compound is in free form or in a pharmaceutically acceptable salt form. Such composition may be an oral composition, injectable composition or suppository. And the composition may be manufactured in a conventional manner by mixing, granulating or coating methods.

In an embodiment of the invention, the composition is an oral composition and it may be a tablet or gelatin capsule. Preferably, the oral composition comprises the present compound together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets, together with c) binders, e.g., magnesium aluminum silicate, starch paste, gelatin, tragamayth, methylcellulose, sodium carboxymethylcellulose and or polyvinylpyrrolidone; and if desired, d) disintegrants, e.g., starches, agar, alginic acid or its sodium salt, or effervescent mixtures; and/or e) additives, e.g., absorbents, colorants, flavors and sweeteners.

In another embodiment of the invention, the composition is an injectable composition, and may be an aqueous isotonic solution or suspension.

In yet another embodiment of the invention, the composition is a suppository and may be prepared from fatty emulsion or suspension.

Preferably, the composition is sterilized and/or contains adjuvant. Such adjuvant can be preserving, stabilizing, wetting or emulsifying agent, solution promoter, salt for regulating the osmotic pressure, buffer and/or any combination thereof.

Alternatively or in addition, the composition may further contain other therapeutically valuable substances for different applications, like solubilizers, stabilizers, tonicity enhancing agents, buffers and/or preservatives.

In an embodiment of the invention, the composition may be a formulation suitable for transdermal application. Such formulation includes an effective amount of the compound of the present invention and a carrier. Preferably, the carrier may include absorbable pharmacologically acceptable solvents to assist passage through the skin of the host. A transdermal device contain the formulation may also be used. The transdermal device may be in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Otherwise, a matrix transdermal formulation may also be used.

In another embodiment of the invention, the composition may be a formulation suitable for topical application, such as to the skin and eyes, and may be aqueous solution, ointment, cream or gel well known in the art.

In another aspect, the present invention provides a method of inhibiting WNT secretion from a cell by contacting the cell with an effective amount of the above said compound or physiologically acceptable salt thereof, or the above said pharmaceutical composition.

In another aspect, the present invention provides a method of inhibiting WNT signaling in a cell with an effective amount of the above said compound or physiologically acceptable salt thereof, or the above said pharmaceutical composition. In one embodiment, the cell is contained within a mammal, and the administered amount is a therapeutically effective amount. In another embodiment, the inhibition of WNT signaling further results in the inhibition of the growth of the cell. In a further embodiment, the cell is a cancer cell. In yet another embodiment, the cell is a fibrogenic cell.

Cell proliferation is measured by using methods known to those skilled in the art. For example, a convenient assay for measuring cell proliferation is the CellTiter-Glo™ Assay commercially available from Promega (Madison, Wis.). The assay procedure involves adding the CellTiter-Glo® reagent to cells cultured on multi-well dishes. The luminescent signal, measured by a luminometer or an imaging device, is proportional to the amount of ATP present, which is directly proportional to the number of viable cells present in culture. In addition, cell proliferation may also be measured using colony formation assays known in the art.

The present invention also provides a method for treating cancers or fibroses related to the WNT signaling pathway with an effective amount of the present compound. Those skilled in the art would readily be able to determine whether a cancer is related to the Wnt pathway by analyzing cancer cells using one of several techniques known in the art. For example, one could examine cancer cells for aberrations in the levels of proteins or mRNAs involved in Wnt signaling using immune and nucleic acid detection methods.

Cancers or fibroses related to the Wnt pathway include those in which activity of one or more components of the Wnt signaling pathways are upregulated from basal levels. In one embodiment, inhibiting the Wnt pathway may involve inhibiting Wnt secretion. As another example, inhibiting the Wnt pathway may involve inhibiting components downstream of the cell surface receptors. In another embodiment, inhibition of Wnt secretion may involve inhibiting the activity of any of the proteins implicated in the secretion of functional WNTs.

Furthermore, the invention provides a method for treating a WNT pathway disorder in a subject suffering from the disorder by administering to the subject a therapeutically effective amount of a WNT inhibitor. In one embodiment, the disorder is a cell proliferative disorder associated with aberrant, e.g., increased, activity of WNT signaling. In another embodiment, the disorder results from increased amount of a WNT protein. In yet another embodiment, the cell proliferative disorder is cancer, include but are not limited to: lung (small cell and non-small cell), breast, prostate, carcinoid, bladder, gastric, pancreatic, liver (hepatocellular), hepatoblastoma, colorectal, head cancer and neck squamous cell carcinoma, esophageal, ovarian, cervical, endometrial, mesothelioma, melanoma, sarcoma, osteosarcoma, liposarcoma, thyroid, desmoids, chronic myelocytic leukemia (AML), and chronic myelocytic leukemia (CML). In yet another embodiment, the cell proliferative disorder is fibrosis, include but are not limited to: lung fibrosis, such as idiopathic pulmonary fibrosis and radiation-induced fibrosis, renal fibrosis and liver fibrosis including liver cirrhosis. In yet another embodiment, the disorder is osteoarthritis, Parkinson's disease, retinopathy, macular degeneration.

For therapeutically use, the compound of the present invention could be administered in a therapeutically effective amount via any acceptable way known in the art singly. As used herein, the therapeutically effective amount may vary widely depending on the severity of the disease, the age and relative health of the subject, the potency of the compound used and other factors. Generally, the satisfactory result is indicated to be obtained systemically at a daily dosage of about 0.03 to 2.5 mg/kg per body weight of the subject. In one embodiment, the indicated daily dosage for larger mammal as human is in the range from about 0.5 mg to about 100 mg. Preferably, the compound is administered in divided doses up to four times a day or in retard form. In another embodiment, suitable unit dosage forms for oral administration comprise from ca. 1 to 100 mg active ingredient.

Alternatively, the compound of the present invention may be administered in a therapeutically effective amount as the active ingredient in combination with one or more therapeutic agents, such as pharmaceutical combinations. There may be synergistic effects when the compound of the present invention is used with a chemotherapeutic agent known in the art. The dosage of the co-administered compounds could vary depending on the type of co-drug employed, the specific drug employed, the condition being treated and so forth.

The compound of the present invention or the composition thereof may be administered by any conventional route. In one embodiment, it is administered enterally, such as orally, and in the form of tablets or capsules. In another embodiment, it is administered parenterally and in the form of injectable solutions or suspensions. In yet another embodiment, it is administered topically and in the form of lotions, gels, ointments or creams, or in a nasal or suppository form.

In another aspect, the invention also provides a pharmaceutical combination, preferably, a kit, comprising a) a first agent which is the compound of the present invention as disclosed herein, in free form or in pharmaceutically acceptable salt form, and b) at least one co-agent. In addition, the kit may comprise instructions for its administration.

The combination of the present invention may be used in vitro or in vivo. Preferably, the desired therapeutic benefit of the administration may be achieved by contacting cell, tissue or organism with a single composition or pharmacological formulation that includes the compound of the present invention and one or more agents, or by contacting the cell with two or more distinct compositions or formulations, wherein one composition includes one agent and the other includes another. The agents of the combination may be administered at the same time or separately within a period of time. Preferably, the separate administration can result in a desired therapeutic benefit. The present compound may precede, be co-current with and/or follow the other agents by intervals ranging from minutes to weeks. A person skilled in the art could generally ensure the interval of the time of each delivery, wherein the agents administered separately could still be able to exert an advantageously combined effect on the cell, tissue or organism. In one embodiment, it is contemplated that one may contact the cell, tissue or organism with two, three, four or more modalities substantially simultaneously as the candidate substance, i.e., with less than about one minute. In another embodiment, one or more agents may be administered about between 1 minute to 14 days.

In another aspect, the present provides the use of the present compound or physiologically acceptable salt thereof, or the present pharmaceutical composition for the manufacture of a medicament for treating a WNT pathway mediated disorder as the above described.

In another aspect, the present provides a process for preparing the compound of the present invention or the salts or derivatives thereof.

In one embodiment, the compound having Formula (I) may be prepared following any one of the synthetic methodologies described in Examples below. In the reactions described, reactive functional groups, for example hydroxy, amino, imino, thio or carboxy groups, where these are desired in the final product, may be protected to avoid their unwanted participation in the reactions. Conventional protecting groups may be used in accordance with standard practice (see e.g., T. W. Greene and P. G. M. Wuts in "Protective Groups in Organic Chemistry", John Wiley and Sons, 1991). Suitable leaving groups for use in the synthetic methodologies described include halogen leaving groups and other conventional leaving groups known in the art. Preferably, the leaving group is chloro or bromo.

In another embodiment, the compound of the invention or the salts thereof may also be obtainable in the form of hydrates, or their crystals may include for example the solvent used for crystallization (present as solvates). Salts can usually be converted to compounds in free form by treating with suitable basic agents, preferably with alkali metal carbonates, alkali metal hydrogen carbonates, or alkali metal hydroxides, more preferably with potassium carbonate or sodium hydroxide. A compound of the invention in a base addition salt form may be converted to the corresponding free acid by treating with a suitable acid, such as hydrochloric acid. In view of the close relationship between the novel compounds in free form and those in the form of their salts, including those salts that may be used as intermediates, for example in the purification or identification of the novel compounds, any reference to the free compounds is to be understood as referring also to the corresponding salts, as appropriate.

Salts of the present compound with a salt-forming group may be prepared in a manner known in the art. Acid addition salts of compound of Formula (I) may thus be obtained by treatment with an acid or with a suitable anion exchange reagent. Pharmaceutically acceptable salts of the compound of the invention may be formed as acid addition salts from compound of Formula (I) with a basic nitrogen atom with organic or inorganic acids.

Preferably, suitable inorganic acids include, but are not limited to, halogen acids, such as hydrochloric acid, sulfuric acid, or phosphoric acid.

Preferably, suitable organic acids include, but are not limited to, carboxylic, phosphoric, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, suberic acid, azelaic acid, -malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4 aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, 2-hydroxysulfonic acid, 2-naphthalenesulfonic acid, 1,5-naphthalene-disulfonic acid, 2-, 3- or 4 methylbenzenesulfonic acid, methylsulfuric acid, ethylsulfuric acid, dodecylsulfuric acid, N cyclohexylsulfamic acid, N-methyl-, N-ethyl- or N-propyl-sulfamic acid, or other organic protonic acids, such as ascorbic acid.

Alternatively, it is also possible to use pharmaceutically unacceptable salts for isolation or purification, for example picrates or perchlorates. But for therapeutic use, only pharmaceutically acceptable salts or free compounds are employed, where applicable in the form of pharmaceutical preparations.

In yet another embodiment, compound of the present invention in unoxidized form may be prepared from N-oxides of compound of the invention by treating with a reducing agent in a suitable inert organic solvent at 0 to 80° C. Preferably, the reducing agent is sulfur, sulfur dioxide, triphenyl phosphine, lithium borohydride, sodium borohydride, phosphorus trichloride, tribromide, or the like. Preferably, the invert organic solvent is acetonitrile, ethanol, aqueous dioxane, or the like.

In yet another embodiment, prodrug derivatives of the compound of the present invention may be prepared by methods known in the art (for further details see Saulnier et al., (1994), Bioorganic and Medicinal Chemistry Letters, Vol. 4, p. 1985). In a preferable embodiment, an appropriate prodrug may be prepared by reacting a non-derivatized compound of the invention with a suitable carbamylating agent such as 1,1-acyloxyalkylcarbanochloridate, para-nitrophenyl carbonate, or the like.

In yet another embodiment, protected derivatives of the compound of the present invention may be made by means known in the art. A detailed description of techniques applicable to the creation of protecting groups and their removal may be found in T. W. Greene, "Protecting Groups in Organic Chemistry", 3rd edition, John Wiley and Sons, Inc., 1999.

In yet another embodiment, compound of the present invention may be prepared as their individual stereoisomers. The process includes reacting a racemic mixture of the compound with an optically active resolving agent to form a pair of diastereoisomeric compounds, separating the diastereomers and recovering the optically pure enantiomers. Resolution of enantiomers may be carried out using covalent diastereomeric derivatives of the compound of the present invention, or by using dissociable complexes such as crystalline diastereomeric salts. Diastereomers have distinct physical properties presented by melting points, boiling points, solubilities, reactivity, etc., and may be readily separated by taking advantage of these dissimilarities. The diastereomers may be separated by fractionated crystallization, chromatography, or by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture may be found in Jean Jacques, Andre Collet, Samuel H. Wilen, "Enantiomers, Racemates and Resolutions", John Wiley And Sons, Inc., 1981.

In conclusion, the compound of the present invention could be made by the process described in the Examples; optionally a pharmaceutically acceptable salt may be converted from the compound of the present invention;

optionally a pharmaceutically acceptable N-oxide may be converted from an unoxidized form of the compound the present invention;

optionally an individual isomer of the compound of the present invention is resolved from a mixture of isomers; and optionally a pharmaceutically acceptable prodrug derivative may be converted from a non-derivatized compound of the present invention.

Insofar as the production of the starting materials is not particularly described, the compounds are known or can be prepared analogously to methods known in the art or as disclosed in the Examples hereinafter. One of skill in the art will appreciate that the above transformations are only representative of methods for preparation of the compounds of the present invention, and that other well known methods can similarly be used.

DETAILED DESCRIPTION OF PREFERRED EMBODIMENTS

The present invention is further exemplified, but not limited, by the following and Examples that illustrate the preparation of the compounds of the invention.

| Abbreviation | Definition or Explanation |
|---|---|
| DCM | Dichloromethane |
| DIEA | N,N'-Diisopropylethylamine |
| DMF | N,N-Dimethylformamide |
| eq. | equivalents |
| TEA | Triethylamine |
| THF | Tetrahydrofuran |
| RT | Room Temperature |
| EA | Ethyl acetate |
| $Pd_2(dba)_3$ | Tris(dibenzylideneacetone)dipalladium(0) |
| s-Phos | 2-Dicyclohexylphosphino-2',6'-dimethoxybiphenyl |
| $Pd(PPh_3)_4$ | Tetrakis(triphenylphosphine)palladium |

Example 1

N-(4-(2-methylpyridin-4-yl)benzyl)-6-(2-methylpyridin-4-yl)-2,7-naphthyridin-1-amine (Compound No. 1)

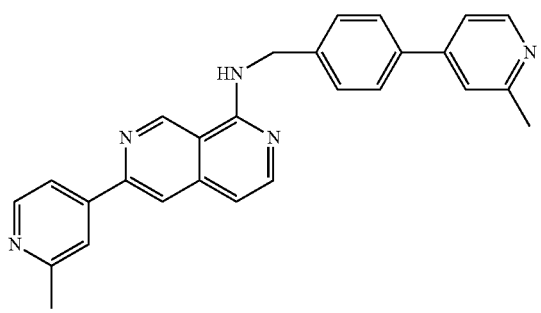

Step 1:

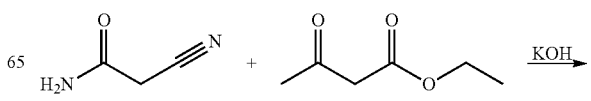

-continued

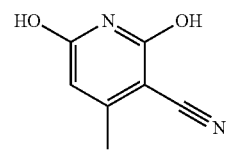

2-Cyanoacetamide (50 g, 601.8 mmol) and ethyl acetoacetate (75 mL, 601.8 mmol) were dissolved in MeOH. KOH (37.0 g, 1.1 eq) was dissolved in MeOH, and added dropwise into the mixture, some white solid came out. The mixture was heated up to reflux at oil bath for 8 h, and then cooled down to RT. The solid was filtered and then re-dissolved into hot water, and then filtered again. 6N HCl was added into the filtration to neutralize till pH<7. The white solid was out again and filtered. The solid was further washed with MeOH, water and MeOH, and then dried by vacuum to get the final product 3-ethynyl-4-methylpyridine-2,6-diol (yield ~41%).

Step 2:

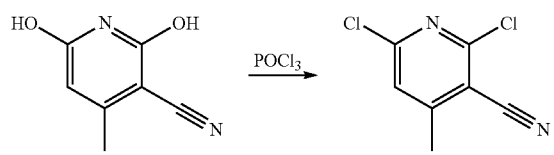

3-ethynyl-4-methylpyridine-2,6-diol (28.0 g, 195.2 mmol) was dissolved in POCl₃ (60.0 mL). The reaction mixture was sealed in a pressure tube and heated up to 180° C. for 6 h. After the reaction was cooled down to room temperature, the excessive POCl₃ was removed under the vacuum. Slowly added crushed ice into the mixture, and the solid came out. Filtered the solid out and dried under the vacuum to get the final product 2,6-dichloro-4-methylpyridine-3-carbonitrile (yield ~92%) without further purity.

Step 3:

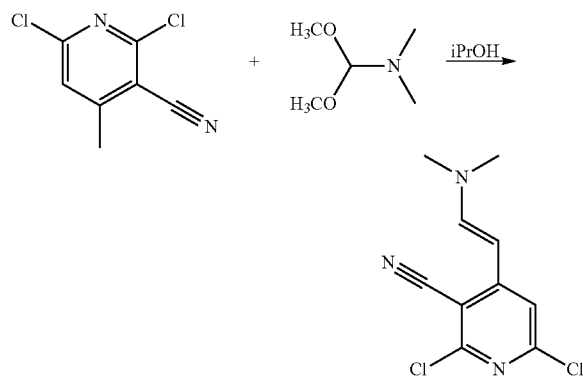

2,6-dichloro-4-methylpyridine-3-carbonitrile (20.0 g, 107.5 mmol) in 200 mL of isopropyl alcohol was added N,N-dimethylformamide dimethylacetal (12.82 g, 107.5 mmol) and the reaction was stirred at 65° C. for 18 h. After cooling down the reaction to RT, the precipitate was collected by filtration and washed with 50 mL of isopropyl alcohol, and air dried to give the product 2,6-dichloro-4-((E)-2-(dimethylamino)vinyl)pyridine-3-carbonitrile (yield ~26%) without further purification.

Step 4:

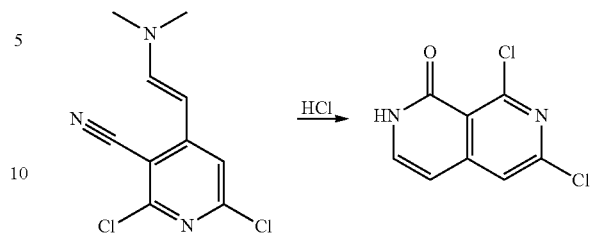

2,6-dichloro-4-((E)-2-(dimethylamino)vinyl)pyridine-3-carbonitrile (4.0 g, 16.6 mmol) was added with 20 mL concentrated HCl in a sealed tube. The reaction is stirred at 45° C. for 18 h. After cooling down the reaction to RT, ice water was added to the solution resulting heavy yellow slurry. The precipitate was collected by filtration, washed with cold water, ether and ethyl acetate, and dried under vacuum to get light yellow solid 6,8-dichloro-2,7-naphthyridin-1(2H)-one (yield ~80%). MS m/z 215.0 (M+1). ¹HNMR (300 MHz, DMSO-d6): δ11.75 (s, 1H), 7.76 (s, 1H), 7.50 (t, J=6.6 Hz, 1H), 6.52 (d, J=6.6 Hz, 1H).

Step 5:

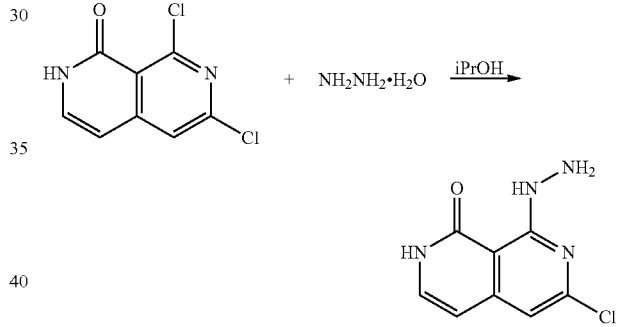

6,8-dichloro-2,7-naphthyridin-1(2H)-one (3.0 g, 13.96 mmol) was dissolved in iPrOH (120 mL) to form a kind of suspension. The solution was cooled down to 0° C. in ice bath, and then hydrazine solution (5.6 g, 80%, 10 eq) was added dropwise. The mixture was stirred at RT for 15 minutes, and then heated in oil bath at 55° C. for overnight. After the reaction mixture was cooled down to RT, filtered to get the solid directly, and then the solid was washed with 70 mL MeOH and dried by vacuum. The product 6-chloro-8-hydrazinyl-2,7-naphthyridin-1(2H)-one (yield ~98%) was used in the next step reaction directly without further purification.

Step 6:

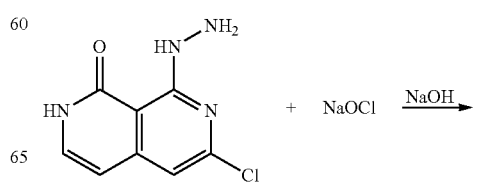

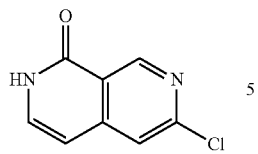

6-chloro-8-hydrazinyl-2,7-naphthyridin-1(2H)-one (1.50 g, 7.12 mmol) was dissolved into MeCN (90 mL) to form a kind of suspension. 1N NaOH (17.80 mL, 2.5 eq) was added, and then equal amount of water (107.80 mL) was added into the mixture. The reaction mixture was heated at 50° C., stirred till becoming the clear solution. The solution was cooled down to 0° C. again, and NaOCl (11.05 g, 12% solution, 2.5 eq) was added dropwise, and then reaction was stirred at RT for overnight. After the reaction was done, the solution was cooled down to 0° C. and then added into 1N HCl to neutralize (pH ~6). Precipitate was collected and the filtrate was extracted with 100 mL×2 EA. The organic layer was combined and dried over Na$_2$SO$_4$ and evaporated to give additional crude product. The combined solid material 6-chloro-2,7-naphthyridin-1(2H)-one (yield ~93%) was used in the next reaction without further purification. MS m/z 181.1 (M+1).

Step 7:

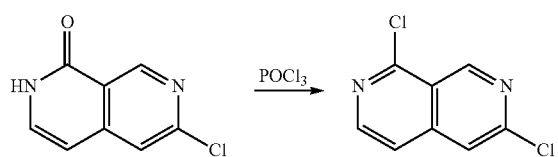 [SMILES: O=c1[nH]ccc2cc(Cl)ncc12 ; "POCl3" ; Clc1cc2ccnc(Cl)c2cn1]

6-chloro-2,7-naphthyridin-1(2H)-one (400 mg, 2.2 mmol) was added in POCl$_3$ (20.0 mL) in a pressure tube. The reaction mixture was heated up to 160° C. for 4 h to get a clear solution. The solution was cooled down to room temperature and poured in DCM, and added crushed ice slowly. Saturated NaHCO$_3$ was added into the mixture to neutralize HCl generated in the reaction. Vacuum to remove DCM and the left water solution was extracted by 100 mL×2 EA. The combined organic layers were washed with brine once, and dried by Na$_2$SO$_4$, and then evaporated under the vacuum to get the solid 1,6-dichloro-2,7-naphthyridine (yield ~73%) to use in the next step reaction without further purifications. MS m/z 199.0 (M+1).

Step 8:

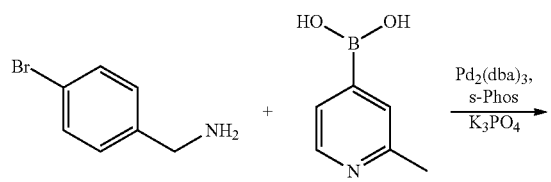

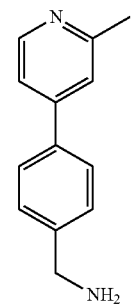

(4-bromophenyl)methanamine (1.00 g, 5.37 mmol) and 2-methylpyridin-4-yl-4-boronic acid (883.30 mg, 6.45 mmol) were dissolved in BuOH (10.0 mL) and water (2.0 mL). K$_3$PO$_4$ (2.28 g, 10.75 mmol), Pd$_2$(dba)$_3$ (120.20 mg, 0.27 mmol) and S-phos (220.70 mg, 0.54 mmol) were added in under N$_2$. The reaction mixture was sealed in a pressure tube and heated up to 125° C. for 1 h. After cooling down the reaction to RT, the mixture was poured into the water and extracted by 100 mL×3 EA. The combined organic layer was washed with brine, dried over Na$_2$SO$_4$, and concentrated under the vacuum to give the crude product. The solid was purified by silicone gel column with 10% MeOH (containing ~2N NH$_3$) in DCM to get the pure (4-(2-methylpyridin-4-yl)phenyl)methanamine (yield ~89%). MS m/z 199.1 (M+1).

Step 9:

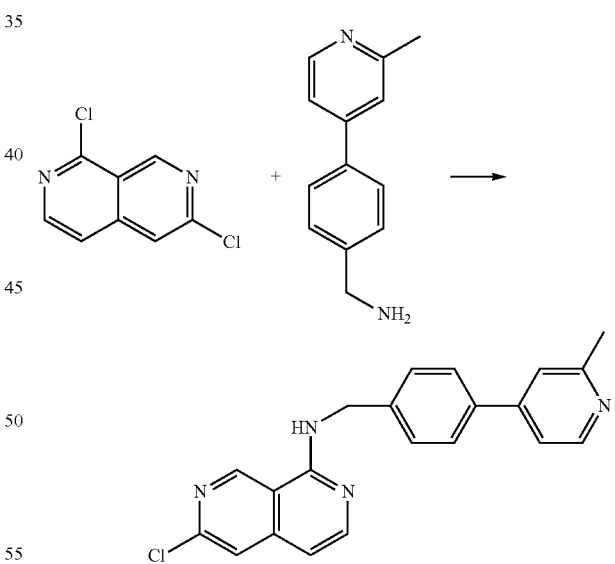

1,6-dichloro-2,7-naphthyridine (160 mg, 0.80 mmol) and (4-(2-methylpyridin-4-yl)phenyl)methanamine (239.10 mg, 1.21 mmol) were dissolved in BuOH (5.0 mL) and heated up to 115° C. for overnight. After the reaction was cooled down to RT, the organic solvent was removed under the vacuum. The crude product was purified by silicone gel flash chromatography with EA/Hexane (1:1) to get the solid N-(4-(2-methylpyridin-4-yl)benzyl)-6-chloro-2,7-naphthyridin-1-amine (yield ~90%). MS m/z 361.1 (M+1).

Step 10:

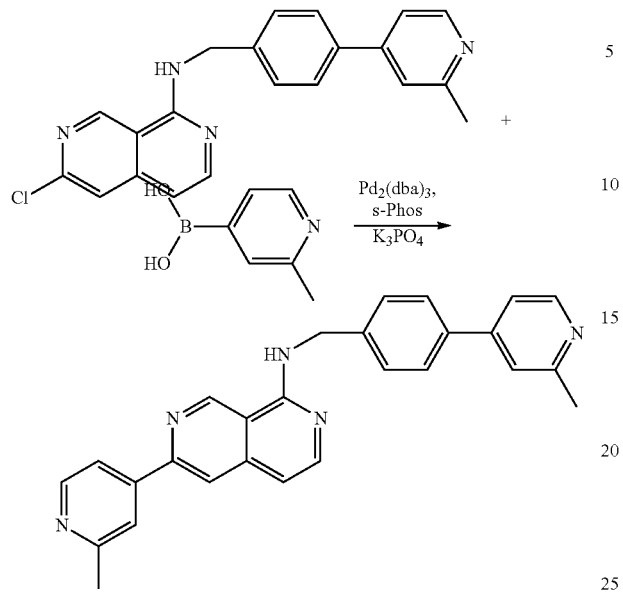

N-(4-(2-methylpyridin-4-yl)benzyl)-6-chloro-2,7-naphthyridin-1-amine (50.00 mg, 0.14 mmol) and 2-methylpyridin-4-yl-4-boronic acid (56.90 mg, 0.42 mmol) were dissolved in BuOH (3.0 mL) and water (0.6 mL). K$_3$PO$_4$ (88.20 mg, 0.028 mmol), Pd$_2$(dba)$_3$ (6.20 mg, 0.014 mmol) and S-phos (11.40 mg, 0.011 mmol) were added into the mixture under N$_2$. The reaction was sealed in a pressure tube and heated up to 105° C. for overnight. After cooling down the reaction to RT, the mixture was poured in water and extracted by EA for three times. The combined organic layer was washed with brine, dried by Na$_2$SO$_4$, and concentrated under the vacuum. The crude product was further purified by prep-TLC with 5% MeOH in DCM to get the final product N-(4-(2-methylpyridin-4-yl)benzyl)-6-(2-methylpyridin-4-yl)-2,7-naphthyridin-1-amine (yield ~70%). MS m/z 418.2 (M+1). $^1$HNMR (300 MHz, CDCl$_3$): δ2.46 (s, 3H), 2.63 (s, 3H), 4.94 (d, J=5.10 Hz, 2H), 5.94 (br, 1H), 6.97 (d, J=5.70 Hz, 1H), 7.31 (d, J=4.20 Hz, 1H), 7.36 (s, 1H), 7.54 (d, J=8.10 Hz, 2H), 7.63 (d, J=8.40 Hz, 2H), 7.90 (s, 1H), 8.19 (d, J=6.00 Hz, 1H), 8.22 (s, 1H), 8.51 (m, 2H), 9.08 (s, 1H), 9.30 (s, 1H).

Example 2

N-(3-methyl-4-(2-methylpyridin-4-yl)benzyl)-6-(2-methylpyridin-4-yl)-2,7-naphthyridin-1-amine (Compound No. 2)

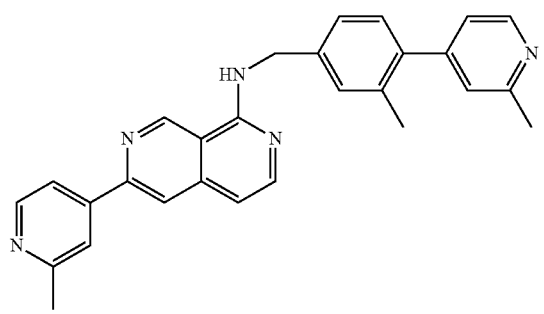 [SMILES: Cc1cc(-c2cc3ccnc(NCc4ccc(-c5ccnc(C)c5)c(C)c4)c3cn2)ccn1]

Step 1:

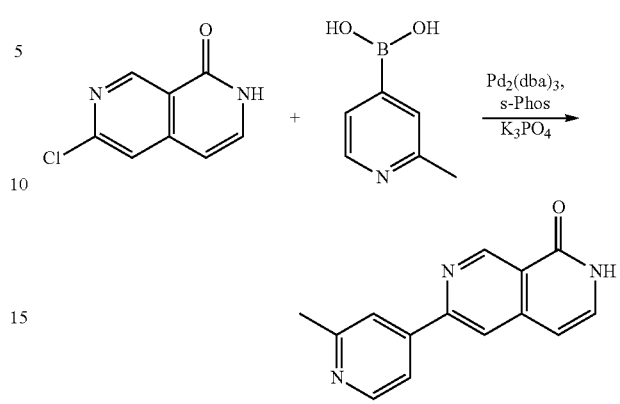

6-chloro-2,7-naphthyridin-1(2H)-one (200 mg, 1.10 mmol) and 2-methylpyridin-4-yl-4-boronic acid (227.60 mg, 1.66 mmol) were dissolved in BuOH (5.0 mL) and water (1.0 mL). K$_3$PO$_4$ (705.20 g, 3.32 mmol), Pd$_2$(dba)$_3$ (49.60 mg, 0.22 mmol) and S-phos (91.00 mg, 0.11 mmol) were added under N$_2$. The reaction mixture in the pressure tube was heated up to 130° C. for 1 h. After cooling down the reaction to RT, poured the mixture into the water, extracted by EA for three times. The combined organic layer was washed with brine, dried over Na$_2$SO$_4$, concentrated under the vacuum to get the crude. The crude product was purified by column with 5% MeOH in DCM to get the final compound 6-(2-methylpyridin-4-yl)-2,7-naphthyridin-1(2H)-one (yield ~61%). MS m/z 238.1 (M+1).

Step 2:

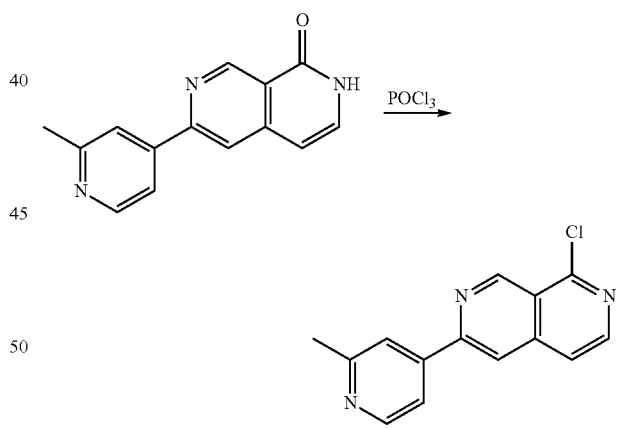

6-(2-methylpyridin-4-yl)-2,7-naphthyridin-1(2H)-one (150 mg, 0.63 mmol) was dissolved in POCl$_3$(15.0 mL), the pressure tube was sealed and heated up to 160° C. for 4 h. After cooling down the reaction to RT, excessive POCl$_3$ was removed under vacuum. Crushed ice was slowly added into the mixture, and then added into NaHCO$_3$ to neutralize until pH ~7.5. Extracted the solution by EA three times, the combined organic layer was washed with brine, dried over Na$_2$SO$_4$, and concentrated under vacuum. The crude was purified by column with EA/Hexane (1:1) to get the compound 1-chloro-6-(2-methylpyridin-4-yl)-2,7-naphthyridine (yield ~55%). MS m/z 256.1 (M+1).

Step 3:

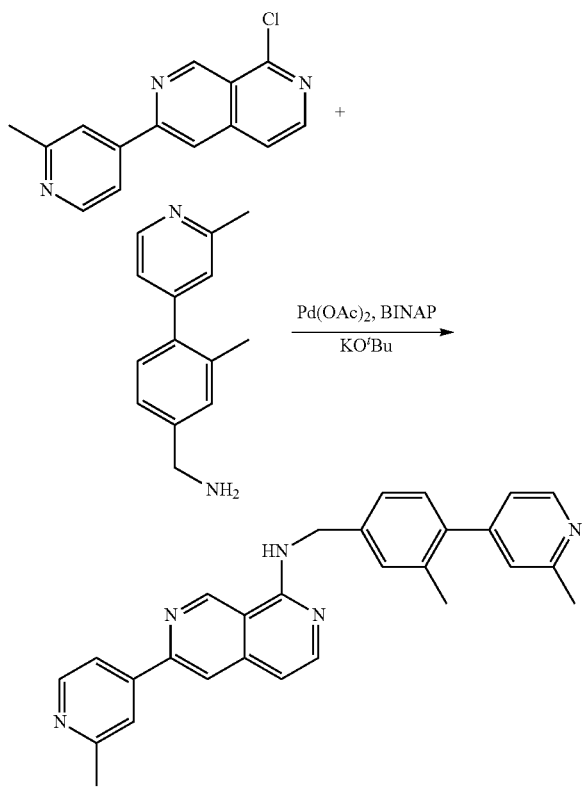

1-chloro-6-(2-methylpyridin-4-yl)-2,7-naphthyridine (10.00 mg, 0.039 mmol) and (3-methyl-4-(2-methylpyridin-4-yl)phenyl)methanamine (10.00 mg, 0.047 mmol) were dissolved in Toluene (1.0 mL). KO'Bu (8.80 mg, 0.078 mmol), Pd(OAc)$_2$ (0.90 mg, 0.0039 mmol) and BINAP (4.90 mg, 0.0078 mmol) was added into the mixture under N$_2$, The reaction was heated up to 100° C. for overnight. After cooling down the reaction to RT, poured the mixture into the water, extracted by EA for three times. The combined organic layer was washed with brine, dried over Na$_2$SO$_4$, then concentrated under vacuum. The crude product was purified by prep-TLC by EA/Hexane (4:1) to get N-(3-methyl-4-(2-methylpyridin-4-yl)benzyl)-6-(2-methylpyridin-4-yl)-2,7-naphthyridin-1-amine (8.8 mg, yield ~52%). 1H NMR (300 MHz, CDCl3): δ2.31 (s, 3H), 2.63 (s, 3H), 2.70 (s, 3H), 4.91 (d, J=5.10 Hz, 2H), 5.88 (br, 1H), 7.00 (d, J=5.40 Hz, 1H), 7.08 (d, J=5.10 Hz, 1H), 7.12 (s, 1H), 7.22 (d, J=7.50 Hz, 1H), 7.36 (m, 2H), 7.77 (d, J=4.50 Hz, 1H), 7.88 (s, 1H), 7.98 (s, 1H), 8.24 (d, J=6.00 Hz, 1H), 8.53 (d, J=4.80 Hz, 1H), 8.64 (d, J=5.40 Hz, 1H), 9.31 (s, 1H). MS m/z 432.2 (M+1).

Example 3

6-(3-fluorophenyl)-N-((6-(2-methylpyridin-4-yl)pyridin-3-yl)methyl)isoquinolin-1-amine (Compound No. 3)

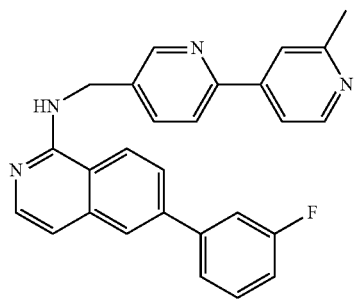 [SMILES: Cc1cc(-c2ccc(CNc3nccc4cc(-c5cccc(F)c5)ccc34)cn2)ccn1]

Step 1:

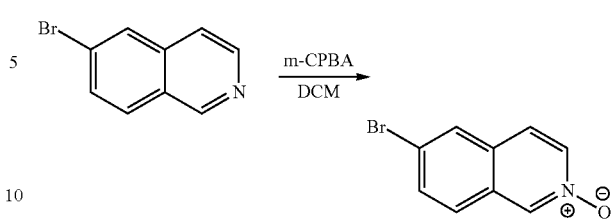

6-bromoisoquinoline (1.80 g, 8.66 mmol) was dissolved in DCM (40 mL), after cooling down the reaction to 0° C. m-CPBA (2.30 g, 1.3 eq, 77% max) was added slowly in small portion. The reaction was warmed up to RT to become a kind of white suspension. In 4 hours, 100 mL DCM was added into the solution, and washed with saturated Na$_2$CO$_3$ solution, water and brine. The separated organic layer was dried over Na$_2$SO$_4$ and removed under the vacuum to get the yellow solid N-oxide 6-bromoisoquinoline without further purification (1.82 g, yield ~93%).

Step 2:

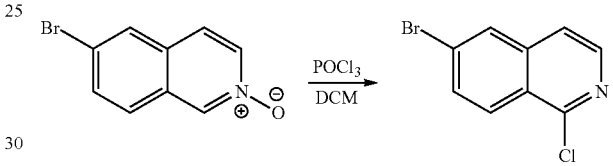

N-oxide 6-bromoisoquinoline (1.82 g, 8.12 mmol) was dissolved in dry DCM (80 mL), POCl$_3$ (1.12 ml, 1.5 eq) was added dropwise at RT. The reaction was heated to 45° C. for 2 hours. After cooling down the reaction to RT, DCM and excessive POCl$_3$ were removed under the vacuum. The crude was re-dissolved into 100 mL DCM and was washed by saturated Na$_2$CO$_3$, water and brine. The separated organic layer was dried over Na$_2$SO$_4$, and concentrated to give brown solid. The crude was purified by flash column using 2% MeOH in DCM to get the pale yellow solid 6-bromo-1-chloroisoquinoline (1.27 g, yield ~65%). MS m/z 242.0 (M+1).

Step 3:

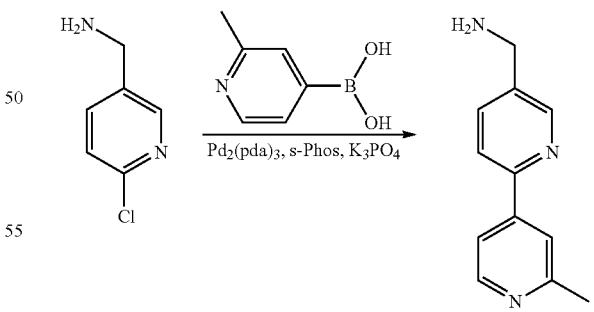

(6-chloropyridin-3-yl)methanamine (300 mg, 2.1 mmol) and 2-methylpyridin-4-ylboronic acid (345 mg, 2.52 mmol) were dissolved in a pressure tube with n-butanol (10 mL) and water (2 mL). K$_3$PO$_4$ (893 mg, 4.2 mmol), Pd$_2$(dba)$_3$ (96.3 mg, 0.105 mmol), and S-phos (86.4 mg, 0.21 mmol) were added under the nitrogen protection. The reaction was heated to 125° C. for 30 minutes and then cooled down to room temperature. The solution was pull in water and extracted by EA for three times. The combined organic layer was washed by brine and dried over Na₂SO₄, and concentrated under the vacuum. The crude was further purified by flash chromatography with 10% MeOH (containing ~2N NH₃) in DCM to get the pure (6-(2-methylpyridin-4-yl)pyridin-3-yl)methanamine (0.19 g, yield ~45%). MS m/z 200.1 (M+1).

Step 4:

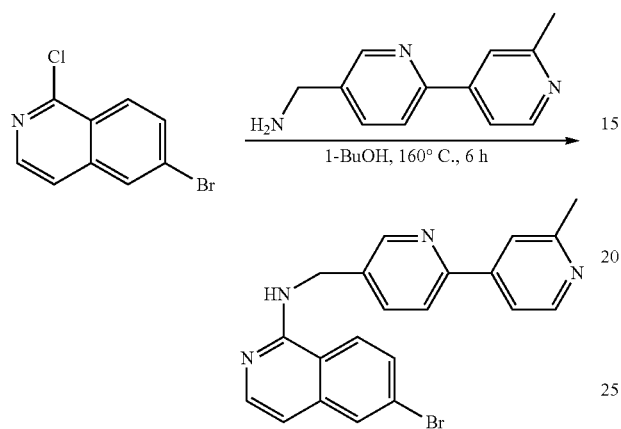

6-bromo-1-chloroisoquinoline (100 mg, 0.41 mmol) and (6-(2-methylpyridin-4-yl)pyridin-3-yl)methanamine (165 mg, 0.82 mmol) were dissolved in 0.5 mL n-BuOH in a sealed tube. The reaction was heat up to 160° C. for 6 h and cooled down to RT. The crude was purified by flash chromatography using 8% MeOH (containing ~2N NH3) in DCM to get the pure 6-bromo-N-((6-(2-methylpyridin-4-yl)pyridin-3-yl)methyl)isoquinolin-1-amine (116 mg, ~70%). MS m/z 405.2 (M+1).

Step 5:

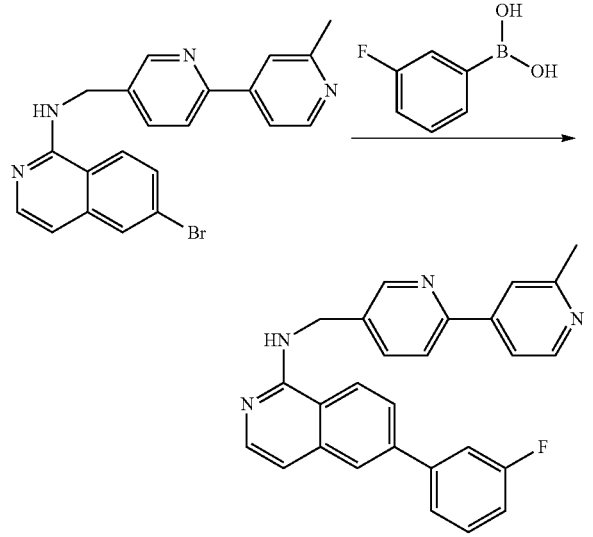

6-bromo-N-((6-(2-methylpyridin-4-yl)pyridin-3-yl)methyl)isoquinolin-1-amine (20 mg, 0.05 mmol), 3-fluorophenylboronic acid (10.5 mg, 0.075 mmol), Na₂CO₃ (21 mg, 0.2 mmol) and Tetrakis(triphenylphosphine)palladium (5.8 mg, 0.005 mmol) were added in a pressure tube. Dioxane/water (3:1, 2 mL) was added into the tube and heated to 125° C. for 10 minutes. After cooling down the reaction to RT, the solution was diluted by 50 ml, water and extracted by EA for 3 times. The combined organic layer was dried over Na₂SO₄, and concentrated under the vacuum. The crude was further purified by flash chromatography with 10% MeOH (containing ~2N NH3) in DCM to get the pure 6-(3-fluorophenyl)-N-((6-(2-methylpyridin-4-yl)pyridin-3-yl)methyl)isoquinolin-1-amine (15.8 mg, ~75%). 1H NMR (400 MHz, CDCl3): δ2.71 (s, 3H), 5.00 (d, 2H), 7.32-7.38 (m, 2H), 7.59-7.65 (m, 1H), 7.75-7.83 (m, 3H), 8.10 (d, J=8.4 Hz, 1H), 8.21 (d, J=8.8 Hz, 1H), 8.27-8.31 (m, 2H), 8.39 (s, 2H), 8.72 (d, J=8.8 Hz, 1H), 8.79 (d, J=6.0 Hz, 1H), 8.91 (d, J=1.6 Hz, 1H), 10.02 (s, 1H). MS m/z 421.2 (M+1).

Example 4

N-(4-(2-methylpyridin-4-yl)benzyl)-2-(2-methylpyridin-4-yl)-1,6-naphthyridin-5-amine (Compound No. 4)

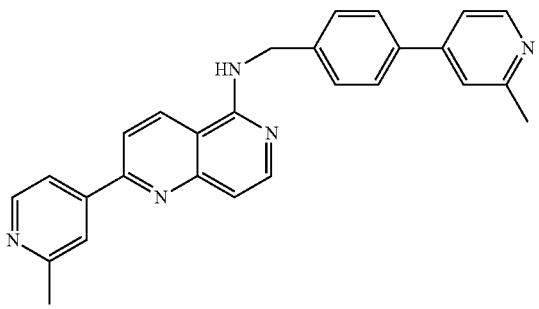

Step 1:

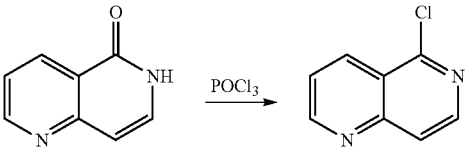

1,6-naphthyridin-5(6H)-one (2.9 g, 19.84 mmol) was dissolved in POCl₃ (40 mL) and heated up to 100° C. for 24 h. After cooling down the reaction to room temperature, the excessive POCl₃ was removed under the vacuum. Small amount crushed ice in saturated Na₂CO₃ solution was added slowly, and lots of bubbles and solid came out. The solid was filtered, and the solution was extracted by EA for 3 times. The combined organic layer was dried over Na₂SO₄, and concentrated under the vacuum. The combined solid was further dried under the vacuum to get 5-chloro-1,6-naphthyridine without further purification (2.6 g, yield ~80%). MS m/z 165.1 (M+1).

Step 2:

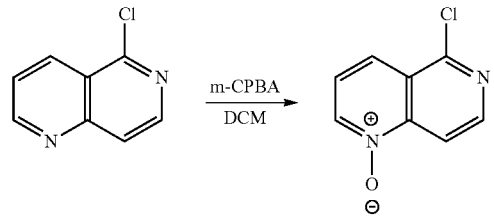 [SMILES: Clc1nccc2ncccc12 ; [O-][n+]1cccc2c(Cl)nccc21]

5-chloro-1,6-naphthyridine (1.5 g, 9.11 mmol) was dissolved in DCM (45 mL) and cooled down by ice bath, m-CPBA (3.7 g, 2 eq, 77% max) was added in small portion and slowly. The reaction was warmed up to RT and continued for 3 hours. 100 mL more DCM was added into the solution, and washed with saturated Na₂CO₃ solution, water and brine. The organic layer was dried over Na₂SO₄, and concentrated under the vacuum to get yellow solid N-oxide 5-chloro-1,6-naphthyridine without further purification (1.25 g, yield ~76%).

Step 3:

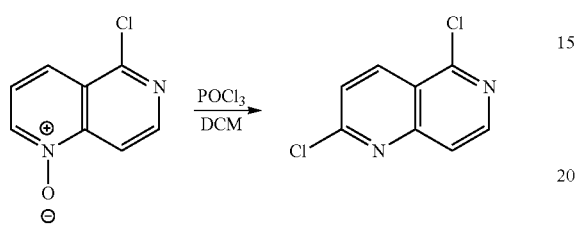

N-oxide 5-chloro-1,6-naphthyridine (1.2 g, 6.64 mmol) was dissolved in dry DCM (30 mL), Et3N (1.85 mL, 13.29 mmol) was added and followed by dropwise adding POCl₃ (0.93 mL, 9.97 mmol) in 5 mL dry DCM. The reaction was heated to 48° C. for 2 hours. 100 mL more DCM was added into the solution, and washed with saturated Na₂CO₃ solution, water and brine. The organic layer was dried over Na₂SO₄, and concentrated under the vacuum to get the yellow solid. The crude was further purified by silicon column using EA/Hexane (1:4) to get white solid 2,5-dichloro-1,6-naphthyridine (0.6 g, yield ~45%). MS m/z 199.0 (M+1)

Step 4:

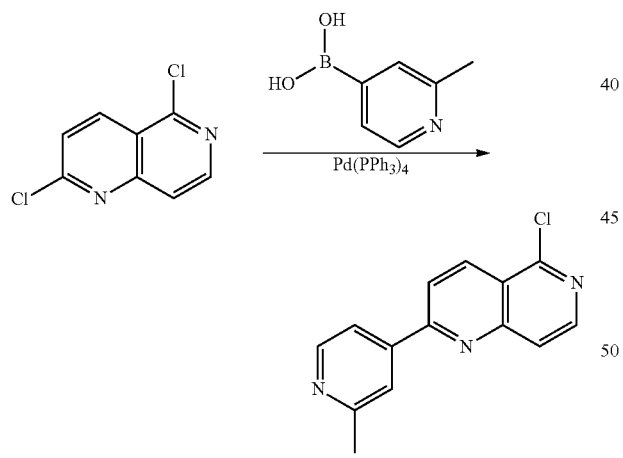

2,5-dichloro-1,6-naphthyridine (200 mg, 1.0 mmol), 2-methylpyridin-4-yl-4-boronic acid (137 mg, 1.0 mmol), Na₂CO₃ (424 mg, 4.0 mmol) and Tetrakis(triphenylphosphine)palladium (116 mg, 0.1 mmol) were added in a flask, dioxane 16 mL and water 4 mL were further added. The reaction was stirred very well and heated to 90° C. for 4 hours. After cooling down the reaction to RT, the solution was diluted by 100 mL water and extracted by EA for 3 times. The combined organic layer was dried over Na2SO4, and concentrated under the vacuum. The crude was further purified by flash chromatography with EA/Hexane (1:1) to get the solid 5-chloro-2-(2-methylpyridin-4-yl)-1,6-naphthyridine (143 mg, yield ~56%). MS m/z 256.1 (M+1)

Step 5:

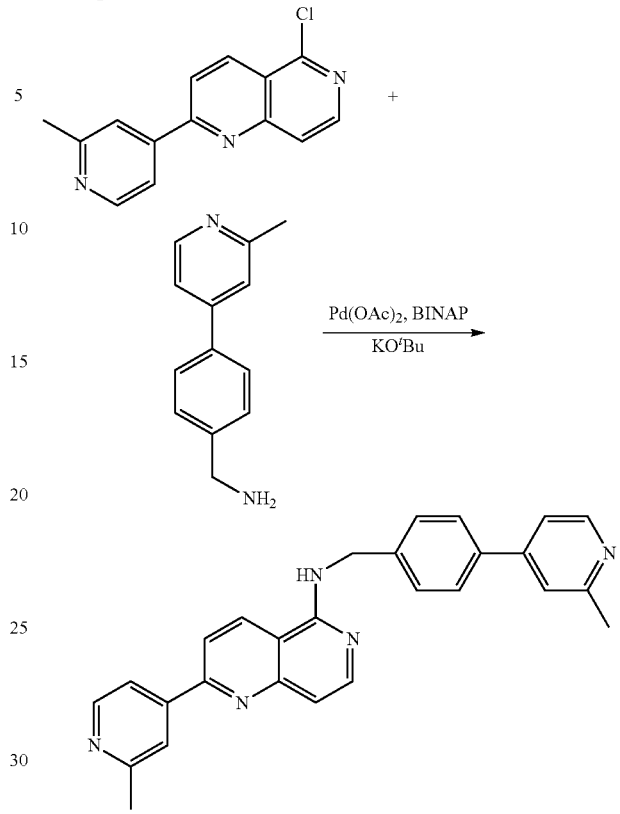

5-chloro-2-(2-methylpyridin-4-yl)-1,6-naphthyridine (20.00 mg, 0.078 mmol) and (4-(2-methylpyridin-4-yl)phenyl)methanamine (25 mg, 0.118 mmol) were dissolved in Toluene (2.0 mL). KO$^t$Bu (13.2 mg, 0.118 mmol), Pd(OAc)₂ (2.7 mg, 0.012 mmol) and BINAP (15.0 mg, 0.024 mmol) were added into the mixture under N₂, The reaction was heated up to 100° C. for overnight. After cooling down the reaction to RT, poured the mixture into the water, extracted by EA for three times. The combined organic layer was washed with brine, dried over Na₂SO₄, then concentrated under vacuum. The crude product was purified by prep-TLC by 8% MeOH in DCM to N-(4-(2-methylpyridin-4-yl)benzyl)-2-(2-methylpyridin-4-yl)-1,6-naphthyridin-5-amine (31 mg, yield ~61%). $^1$H NMR (400 MHz, DMSO-d6): δ9.12 (d, J=8.8 Hz, 1H), 8.77-8.83 (m, 2H), 8.49 (d, J=8.4 Hz, 1H), 8.40 (s, 1H), 8.31 (d, J=6.4 Hz, 1H), 8.21 (s, 1H), 8.11 (d, J=5.6 Hz, 1H), 8.06 (d, J=6.4 Hz, 1H), 7.99 (d, J=8.4 Hz, 2H), 7.65 (d, J=8.4 Hz, 2H), 7.23 (d, J=6.4 Hz, 1H), 5.76 (s, 1H), 4.93 (d, J=5.6 Hz, 2H), 2.72 (s, 6H). MS m/z 432.2 (M+1).

Example 5

N-(4-(2-methylpyridin-4-yl)benzyl)-2-phenylpyrido[4,3-b]pyrazin-5-amine (Compound No. 5)

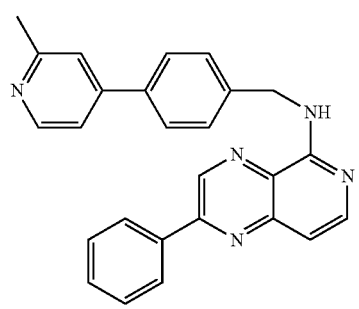 [SMILES: Cc1cc(-c2ccc(CNc3nccc4nc(-c5ccccc5)cnc34)cc2)ccn1]

Step 1:

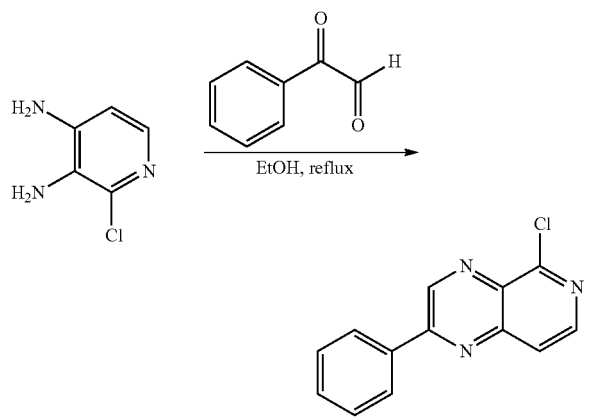

To 20 mL of ethanol was added phenyl gloyoxal monohydrate (940 mg, 6.99 mmol) and 2-chloro-3,4-diaminopyridine (1000 mg, 6.99 mmol). The mixture was refluxed for overnight. After cooling down the reaction, the crude precipitated product was filtered and washed with 15 mL ethanol and dried under vacuum to get 5-chloro-2-phenylpyrido[3,4-b]pyrazine without further purification (1.28 g, yield ~76%), MS m/z 241.0 (M+1); 1H NMR (300 MHz, DMSO-d6): δ 9.82 (s, 1H), 8.64 (d, J=6.0 Hz, 1H), 8.38-8.43 (m, 2H), 8.07 (d, J=6.0 Hz, 1H), 7.64-7.68 (m, 3H).

Step 2:

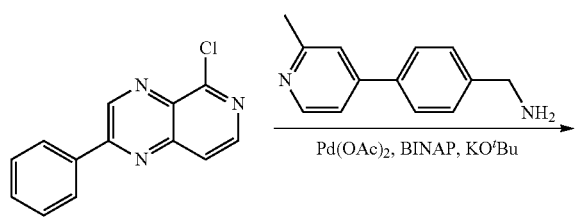

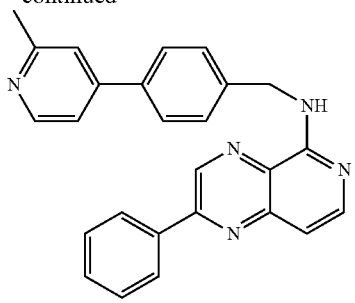

N-(4-(2-methylpyridin-4-yl)benzyl)-2-phenylpyrido[3,4-b]pyrazin-5-amine (50 mg, 0.21 mmol) and (4-(2-methylpyridin-4-yl)phenyl)methanamine (42 mg, 0.21 mmol) were dissolved in Toluene (4.0 mL). KO$^t$Bu (24 mg, 0.21 mmol), Pd(OAc)$_2$ (4.5 mg, 0.021 mmol) and BINAP (26.4 mg, 0.042 mmol) was added into the mixture under N$_2$. The reaction was heated up to 100° C. for overnight. After cooling down the reaction to RT, poured the mixture into the water, extracted by EA for three times. The combined organic layer was washed with brine, dried over Na$_2$SO$_4$, then concentrated under vacuum. The crude product was purified by flash chromatography using 7% MeOH in DCM to get N-(4-(2-methylpyridin-4-yl)benzyl)-2-phenylpyrido[4,3-b]pyrazin-5-amine (61 mg, yield ~72%). MS m/z=404.2 (M+1); $^1$H NMR (400 MHz, DMSO-d6) δ 9.53 (s, 1H), 8.77 (d, J=6.4 Hz, 1H), 8.35-8.39 (m, 2H), 8.21 (s, 1H), 8.11 (d, J=6.0 Hz, 1H), 8.07 (d, J=6.4 Hz, 1H), 7.96 (d, J=8.4 Hz, 2H), 7.60-7.65 (m, 5H), 7.14 (d, J=6.0 Hz, 1H), 5.76 (s, 1H), 4.90 (d, J=6.4 Hz, 2H), 2.71 (s, 3H).

A person skilled in the art can clearly understand and know that the other compounds could be prepared by the same strategy as examples 1-5.

Compounds Table:

| No. | Compound Structure | Compound physical characterization |
|---|---|---|
| 6 | 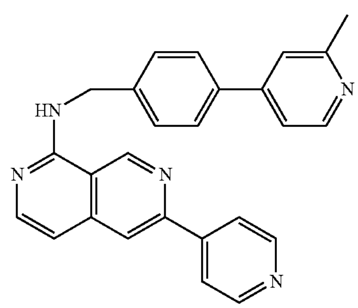 [SMILES: Cc1cc(-c2ccc(CNc3nccc4cc(-c5ccncc5)ncc34)cc2)ccn1] | MS m/z = 404.2 (M + 1); |
| 7 | 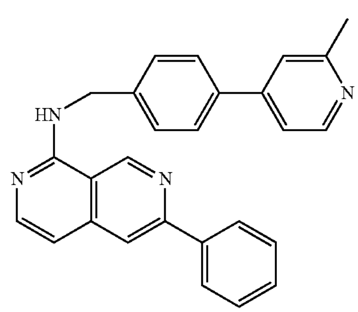 | MS m/z = 403.2 (M + 1); |

-continued

| No. | Compound Structure | Compound physical characterization |
|---|---|---|
| 8 | 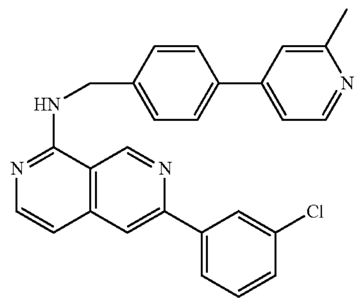 | MS m/z = 437.2 (M + 1); |
| 9 | 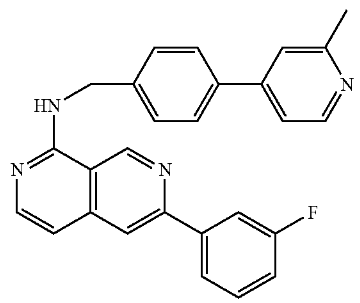 | MS m/z = 421.2 (M + 1); $^1$H NMR (400 MHz, DMSO-d6) δ 9.82 (s, 1H), 8.76 (d, J = 6.0 Hz, 1H), 8.39 (s, 1H), 8.17 (s, 1H), 7.95-8.18 (m, 6H), 7.58-7.66 (m, 3H), 7.35 (t, J = 8.0 Hz, 1H), 7.07 (d, J = 6.0 Hz, 1H), 5.77 (s, 1H), 4.92 (d, J = 6.0 Hz, 1H), 2.70 (s, 3H) |
| 10 | 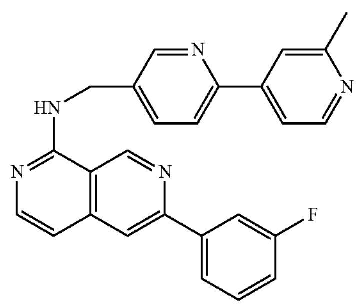 [SMILES: Cc1cc(-c2ccc(CNc3nccc4cc(-c5cccc(F)c5)ncc34)cn2)ccn1] | MS m/z = 422.2 (M + 1); |
| 11 | 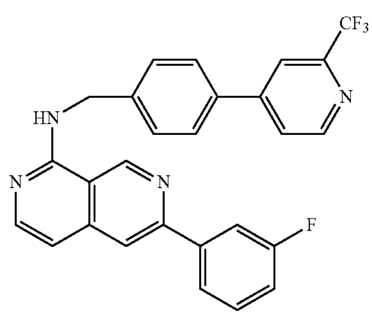 [SMILES: Fc1cccc(-c2cc3ccnc(NCc4ccc(-c5ccnc(C(F)(F)F)c5)cc4)c3cn2)c1] | MS m/z = 475.2 (M + 1); |
| 12 | 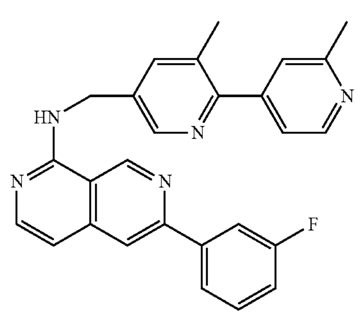 [SMILES: Cc1cc(-c2ncc(CNc3nccc4cc(-c5cccc(F)c5)ncc34)cc2C)ccn1] | MS m/z = 436.2 (M + 1); |

| No. | Compound Structure | Compound physical characterization |
|---|---|---|
| 13 | 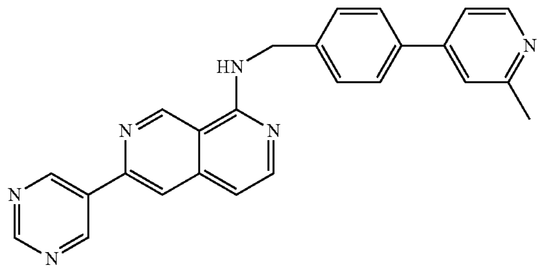 [SMILES: Cc1cc(-c2ccc(CNc3nccc4cc(-c5cncnc5)ncc34)cc2)ccn1] | MS m/z = 405.2 (M + 1); |
| 14 | 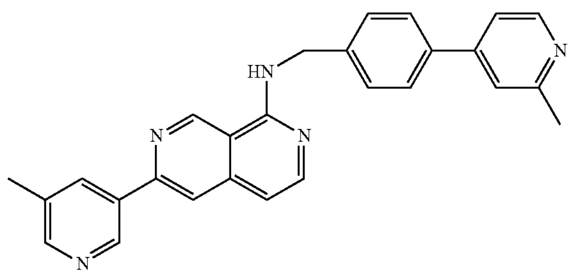 | MS m/z = 418.2 (M + 1); $^1$H NMR (300 MHz, CDCl$_3$): δ 2.46 (s, 3H), 2.63 (s, 3H), 4.94 (d, J = 5.10 Hz, 2H), 5.94 (br, 1H), 6.97 (d, J = 5.70 Hz, 1H), 7.31 (d, J = 4.20 Hz, 1H), 7.36 (s, 1H), 7.54 (d, J = 8.10 Hz, 2H), 7.63 (d, J = 8.40 Hz, 2H), 7.90 (s, 1H), 8.19 (d, J = 6.00 Hz, 1H), 8.22 (s, 1H), 8.51 (m, 2H), 9.08 (s, 1H), 9.30 (s, 1H). |
| 15 | 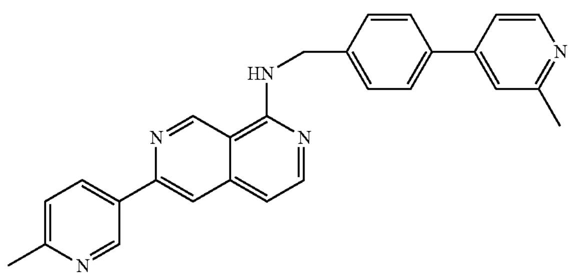 | MS m/z = 418.2 (M + 1); |
| 16 | 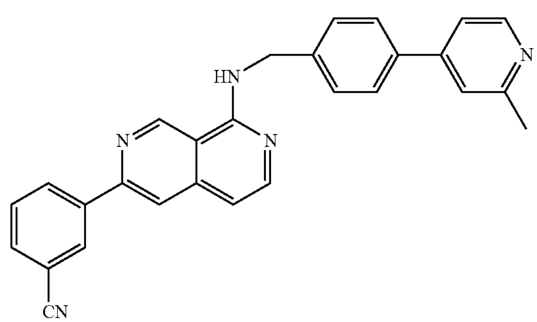 [SMILES: Cc1cc(-c2ccc(CNc3nccc4cc(-c5cccc(C#N)c5)ncc34)cc2)ccn1] | MS m/z = 428.2 (M + 1); $^1$H NMR (300 MHz, CDCl$_3$): δ 2.64 (s, 3H), 4.96 (d, J = 5.10 Hz, 2H), 5.99 (br, 1H), 7.31 (d, J = 5.10 Hz, 1H), 7.37 (s, 1H), 7.63 (m, 1H), 7.73 (m, 1H), 7.91 (s, 1H), 8.22 (d, J = 5.70 Hz, 1H), 8.33 (m, 1H), 8.44 (s, 1H), 8.53 (d, J = 5.10 Hz, 1H), 9.33 (s, 1H). |
| 17 | 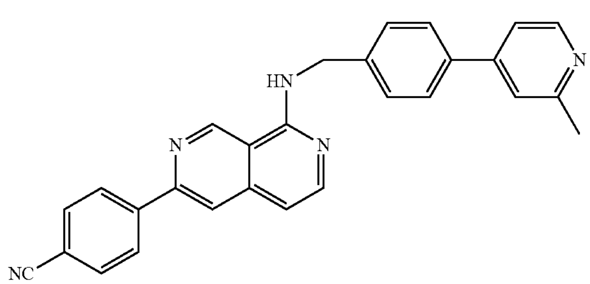 [SMILES: Cc1cc(-c2ccc(CNc3nccc4cc(-c5ccc(C#N)cc5)ncc34)cc2)ccn1] | MS m/z = 428.2 (M + 1); |

-continued

| No. | Compound Structure | Compound physical characterization |
|---|---|---|
| 18 | 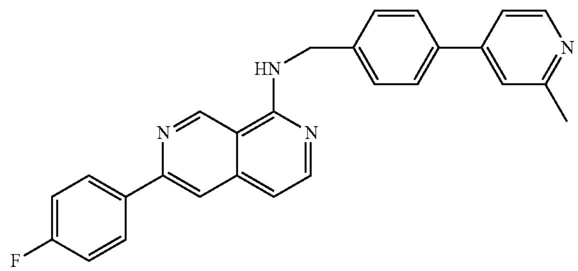 [SMILES: Cc1cc(-c2ccc(CNc3nccc4cc(-c5ccc(F)cc5)ncc34)cc2)ccn1] | MS m/z = 420.2 (M + 1); |
| 19 | 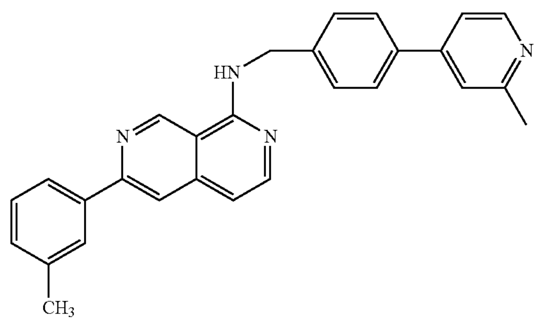 [SMILES: Cc1cccc(-c2cc3ccnc(NCc4ccc(-c5ccnc(C)c5)cc4)c3cn2)c1] | MS m/z = 417.2 (M + 1); |
| 20 | 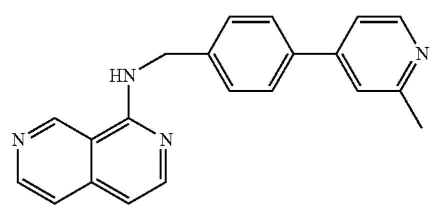 [SMILES: Cc1cc(-c2ccc(CNc3nccc4ccncc34)cc2)ccn1] | MS m/z = 326.1 (M + 1); $^1$H NMR (300 MHz, CDCl$_3$): δ 2.58 (s, 3H), 4.90 (d, J = 5.1 Hz, 2H), 5.96 (br, 1H), 6.91 (d, J = 6.0 Hz, 1H), 7.48-7.58 (m, 4H), 7.62 (d, J = 5.7 Hz, 1H), 7.70 (d, J = 8.4 Hz, 2H), 8.02 (d, J = 5.7 Hz, 1H), 8.40 (d, J = 5.1 Hz, 1H), 8.53 (d, J = 5.7 Hz, 1H), 9.50 (s, 1H). |
| 21 | 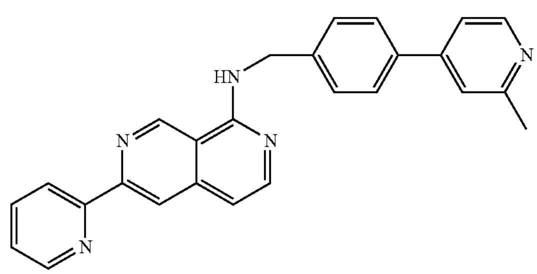 [SMILES: Cc1cc(-c2ccc(CNc3nccc4cc(-c5ccccn5)ncc34)cc2)ccn1] | MS m/z = 404.2 (M + 1); |
| 22 | 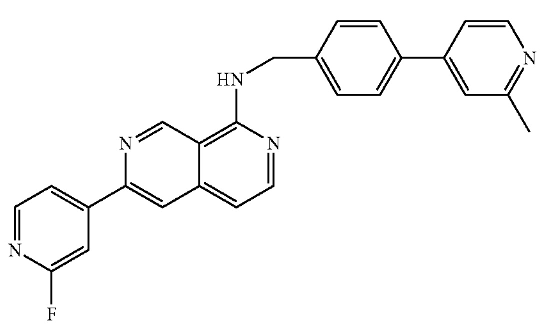 [SMILES: Cc1cc(-c2ccc(CNc3nccc4cc(-c5ccnc(F)c5)ncc34)cc2)ccn1] | MS m/z = 422.2 (M + 1); $^1$H NMR (300 MHz, CDCl$_3$): δ 2.64 (s, 3H), 4.96 (d, J = 5.40 Hz, 2H), 5.96 (br, 1H), 7.01 (d, J = 6.00 Hz, 1H), 7.31 (m, 1H), 7.37 (s, 1H), 7.56 (d, J = 8.10 Hz, 2H), 7.64 (d, J = 8.10 Hz, 2H), 7.88 (m, 1H), 7.99 (s, 1H), 8.25 (d, J = 6.00 Hz, 1H), 8.36 (d, J = 8.10 Hz, 1H), 9.32 (s, 1H). |

-continued

| No. | Compound Structure | Compound physical characterization |
|---|---|---|
| 23 | 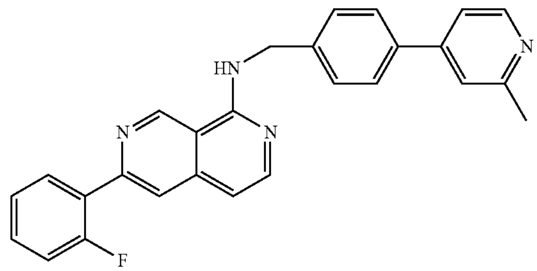 [SMILES: Cc1cc(-c2ccc(CNc3nccc4cc(-c5ccccc5F)ncc34)cc2)ccn1] | MS m/z = 421.2 (M + 1); |
| 24 | 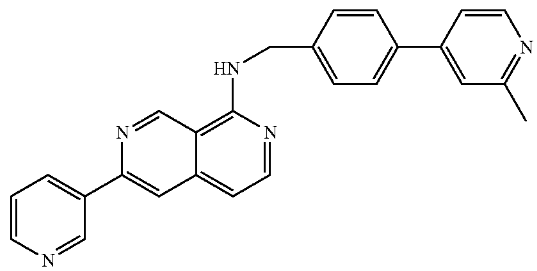 [SMILES: Cc1cc(-c2ccc(CNc3nccc4cc(-c5cccnc5)ncc34)cc2)ccn1] | MS m/z = 404.2 (M + 1); |
| 25 | 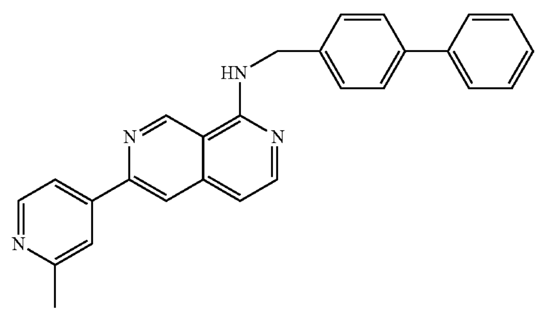 [SMILES: Cc1cc(-c2cc3ccnc(NCc4ccc(-c5ccccc5)cc4)c3cn2)ccn1] | MS m/z = 403.2 (M + 1); |
| 26 | 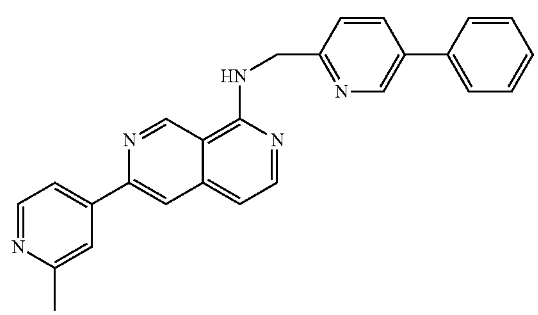 [SMILES: Cc1cc(-c2cc3ccnc(NCc4ccc(-c5ccccc5)cn4)c3cn2)ccn1] | MS m/z = 404.2 (M + 1); |
| 27 | 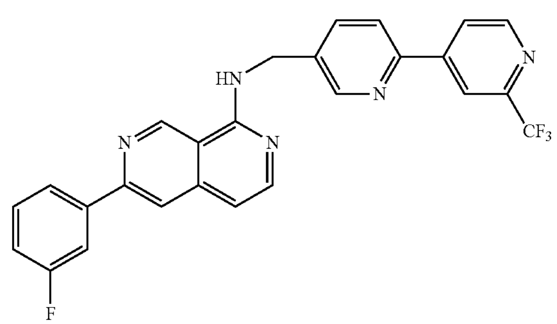 [SMILES: Fc1cccc(-c2cc3ccnc(NCc4ccc(-c5ccnc(C(F)(F)F)c5)nc4)c3cn2)c1] | MS m/z = 476.2 (M + 1); |

| No. | Compound Structure | Compound physical characterization |
|---|---|---|
| 28 | 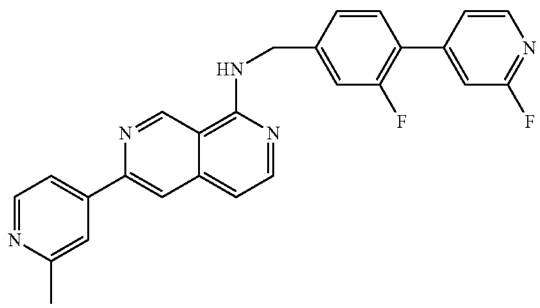 [SMILES: Cc1cc(-c2cc3ccnc(NCc4ccc(-c5ccnc(F)c5)c(F)c4)c3cn2)ccn1] | MS m/z = 440.2 (M + 1); 1H NMR (300 MHz, CDCl3): δ 2.61 (s, 3H), 4.88 (d, J = 5.70 Hz, 2H), 5.98 (br, 1H), 6.92 (d, J = 5.7 Hz, 1H), 7.02 (s, 1H), 7.26 (m, 3H), 7.37 (t, J = 7.8 Hz, 1H), 7.68 (d, J = 5.4 Hz, 1H), 7.79 (s, 1H), 7.89 (s, 1H), 8.11 (d, J = 6.0 Hz, 1H), 8.17 (d, J = 5.1 Hz, 1H), 8.55 (d, J = 5.4 Hz, 1H), 9.26 (s, 1H). |
| 29 | 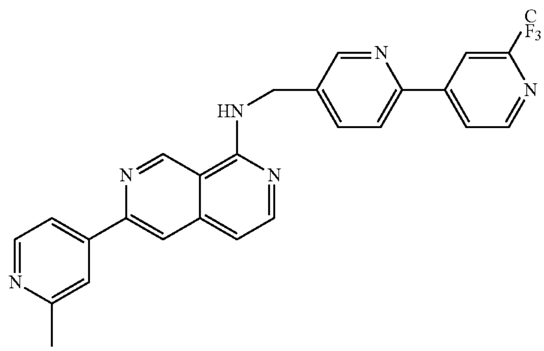 [SMILES: Cc1cc(-c2cc3ccnc(NCc4ccc(-c5ccnc(C(F)(F)F)c5)nc4)c3cn2)ccn1] | MS m/z = 473.2 (M + 1); |
| 30 | 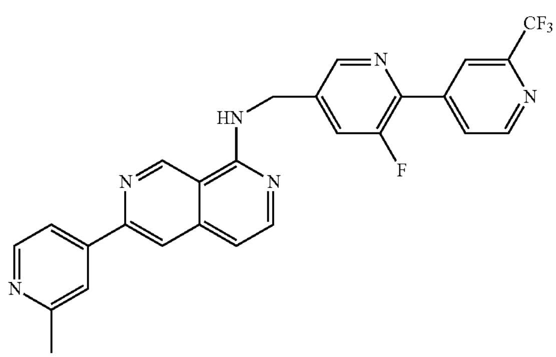 [SMILES: Cc1cc(-c2cc3ccnc(NCc4cnc(-c5ccnc(C(F)(F)F)c5)c(F)c4)c3cn2)ccn1] | MS m/z = 497.2 (M + 1); |
| 31 | 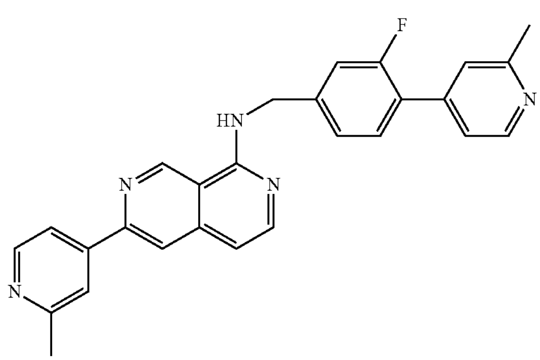 [SMILES: Cc1cc(-c2cc3ccnc(NCc4ccc(-c5ccnc(C)c5)c(F)c4)c3cn2)ccn1] | MS m/z = 436.2 (M + 1); $^1$H NMR (300 MHz, CDCl$_3$): δ 2.63 (s, 3H), 2.70 (s, 3H), 4.96 (d, J = 5.70 Hz, 2H), 6.02 (br, 1H), 7.02 (d, J = 5.70 Hz, 1H), 7.34 (s, 1H), 7.45 (d, J = 7.80 Hz, 2H), 7.61 (s, 1H), 7.78 (d, J = 4.80 Hz, 2H), 7.88 (s, 1H), 7.98 (s, 1H), 8.22 (d, J = 5.70 Hz, 1H), 8.55 (d, J = 5.10 Hz, 2H), 8.64 (d, J = 5.10 Hz, 2H), 9.34 (s, 1H). |

| No. | Compound Structure | Compound physical characterization |
|---|---|---|
| 32 | 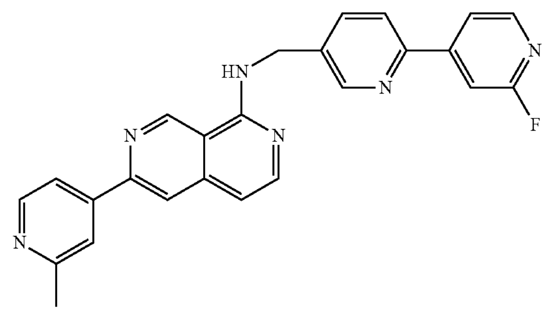 [SMILES: Cc1cc(-c2cc3ccnc(NCc4ccc(-c5ccnc(F)c5)nc4)c3cn2)ccn1] | MS m/z = 423.2 (M + 1); |
| 33 | 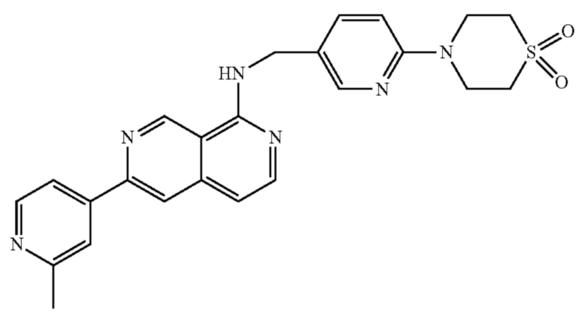 [SMILES: Cc1cc(-c2cc3ccnc(NCc4ccc(N5CCS(=O)(=O)CC5)nc4)c3cn2)ccn1] | MS m/z = 461.2 (M + 1); $^1$H NMR (300 MHz, CDCl$_3$): δ 2.69 (s, 3H), 3.06 (t, 4H), 4.18 (t, 4H), 4.79 (d, J = 5.40 Hz, 2H), 5.85 (br, 1H), 6.76 (d, J = 8.70 Hz, 1H), 6.99 d, J = 6.00 Hz, 1H), 7.69 (q, 1H), 7.76 (q, 1H), 7.86 (s, 1H), 7.96 (s, 1H), 8.22 (d, J = 6.00 Hz, 1H), 8.31 (s, 1H), 8.63 (d, J = 5.40 Hz, 1H), 9.27 (s, 1H). |
| 34 | 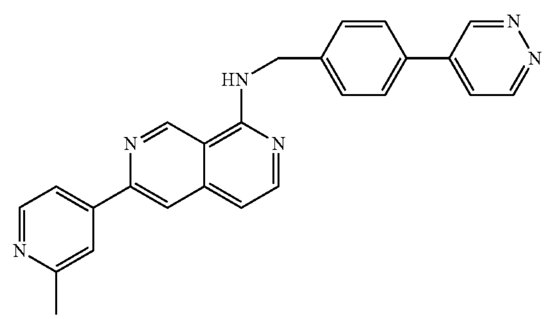 [SMILES: Cc1cc(-c2cc3ccnc(NCc4ccc(-c5ccnnc5)cc4)c3cn2)ccn1] | MS m/z = 405.2 (M + 1); |
| 35 | 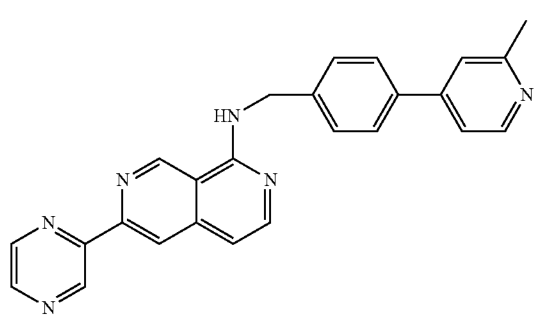 [SMILES: Cc1cc(-c2ccc(CNc3nccc4cc(-c5cnccn5)ncc34)cc2)ccn1] | MS m/z = 405.2 (M + 1); $^1$H NMR (300 MHz, CDCl$_3$): δ 2.64 (s, 3H), 4.96 (d, J = 5.40 Hz, 2H), 5.96 (br, 1H), 7.05 (d, J = 5.70 Hz, 1H), 7.31 (m, 1H), 7.37 (s, 1H), 7.56 (d, J = 8.40 Hz, 2H), 7.64 (d, J = 8.40 Hz, 2H), 8.23 (d, J = 5.70 Hz, 1H), 8.54 (d, J = 5.40 Hz, 1H), 8.57 (s, 1H), 8.64 (d, J = 2.40 Hz, 1H), 8.67 (m, 1H), 9.32 (s, 1H), 9.71 (d, J = 1.50 Hz, 1H). |
| 36 | 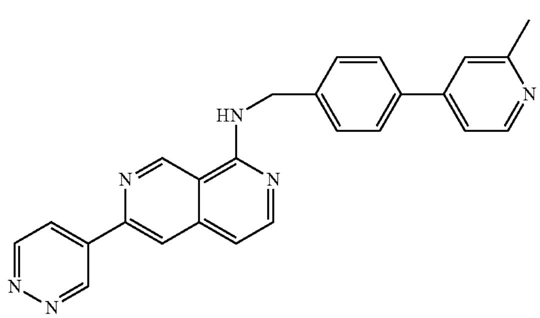 [SMILES: Cc1cc(-c2ccc(CNc3nccc4cc(-c5ccnnc5)ncc34)cc2)ccn1] | MS m/z = 405.2 (M + 1); |

-continued

| No. | Compound Structure | Compound physical characterization |
|---|---|---|
| 37 | 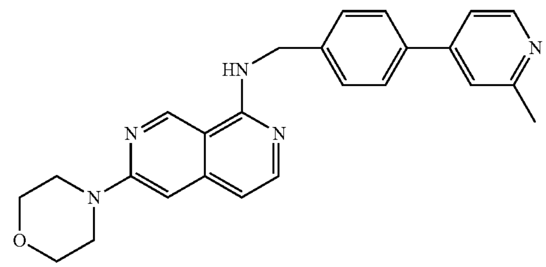 [SMILES: Cc1cc(-c2ccc(CNc3nccc4cc(N5CCOCC5)ncc34)cc2)ccn1] | MS m/z = 412.2 (M + 1); |
| 38 | 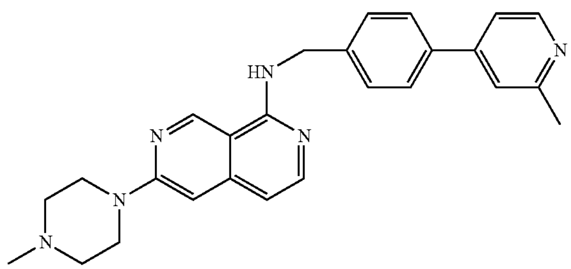 | MS m/z = 425.2 (M + 1); |
| 39 | 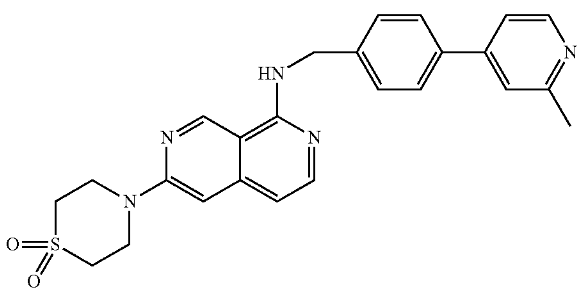 [SMILES: Cc1cc(-c2ccc(CNc3nccc4cc(N5CCS(=O)(=O)CC5)ncc34)cc2)ccn1] | MS m/z = 460.2 (M + 1); $^1$H NMR (300 MHz, CD$_3$OD): δ 2.56 (s, 3H), 3.13 (t, 4H), 4.28 (t, 4H), 4.81 (s, 2H), 6.79 (d, J = 6.30 Hz, 1H), 6.99 (s, 1H), 7.47 (m, 2H), 7.51 (s, 1H), 7.55 (d, J = 6.60 Hz, 2H), 7.71 (d, J = 8.40 Hz, 2H), 8.38 (d, J = 5.40 Hz, 1H), 9.27 (s, 1H). |
| 40 | 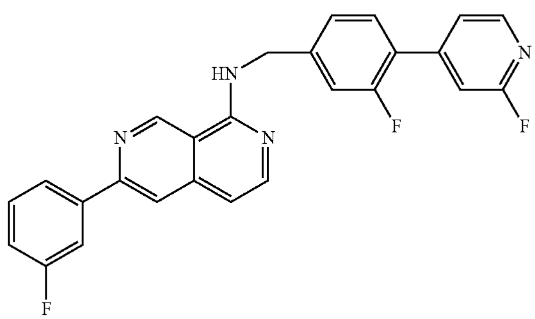 | MS m/z = 443.2 (M + 1); |
| 41 | 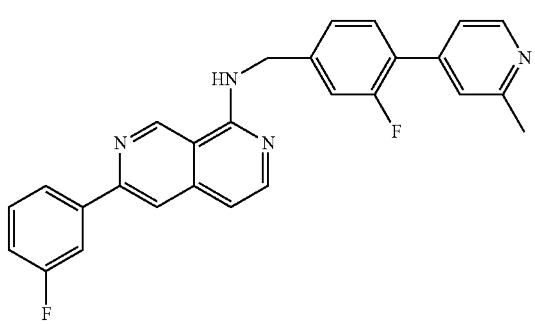 | MS m/z = 439.2 (M + 1); |

-continued

| No. | Compound Structure | Compound physical characterization |
|---|---|---|
| 42 | 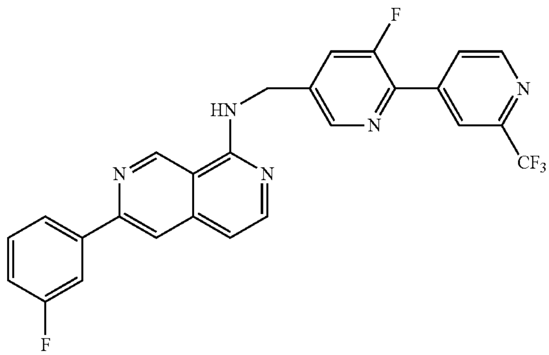 [SMILES: Fc1cccc(-c2cc3ccnc(NCc4cnc(-c5ccnc(C(F)(F)F)c5)c(F)c4)c3cn2)c1] | MS m/z = 494.2 (M + 1); |
| 43 | 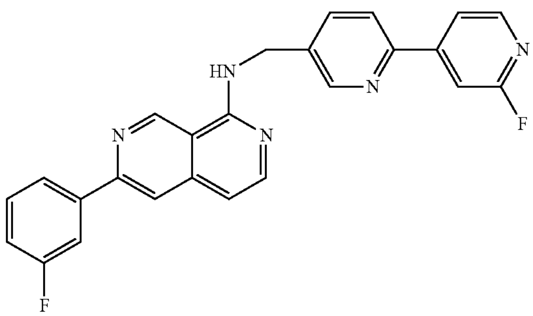 | MS m/z = 426.2 (M + 1); |
| 44 | 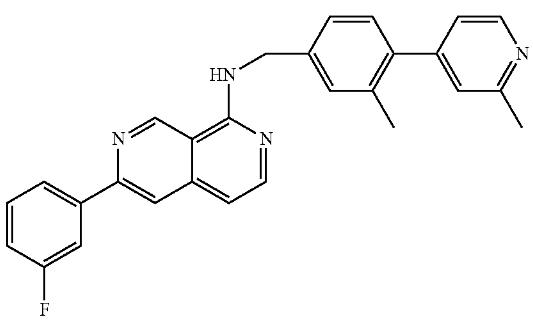 [SMILES: Cc1cc(-c2ccc(CNc3nccc4cc(-c5cccc(F)c5)ncc34)cc2C)ccn1] | MS m/z = 435.2 (M + 1); |
| 45 | 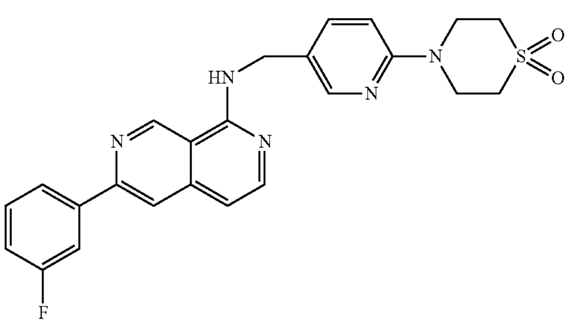 [SMILES: O=S1(=O)CCN(c2ccc(CNc3nccc4cc(-c5cccc(F)c5)ncc34)cn2)CC1] | MS m/z = 464.2 (M + 1); |

| No. | Compound Structure | Compound physical characterization |
|---|---|---|
| 46 | 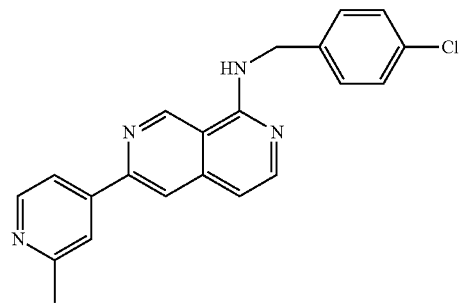 [SMILES: Cc1cc(-c2cc3ccnc(NCc4ccc(Cl)cc4)c3cn2)ccn1] | MS m/z = 361.2 (M + 1); |
| 47 | 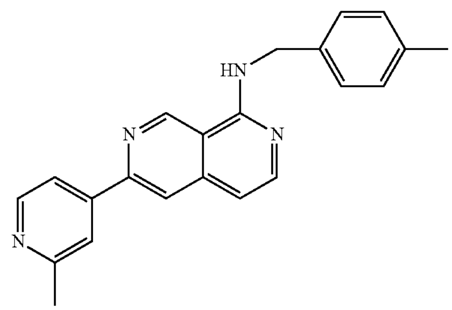 [SMILES: Cc1ccc(CNc2nccc3cc(-c4ccnc(C)c4)ncc23)cc1] | MS m/z = 341.1 (M + 1); $^1$H NMR (300 MHz, CD$_3$OD): δ 2.31 (s, 3H), 2.65 (s, 3H), 4.76 (s, 2H), 6.98 (m, 1H), 7.12 (d, J = 7.80 Hz, 2H), 7.28 (d, J = 8.10 Hz, 2H), 7.92 (m, 1H), 8.03 (m, 2H), 8.17 (s, 1H), 8.52 (d, J = 5.40 Hz, 1H), 9.56 (s, 1H). |
| 48 | 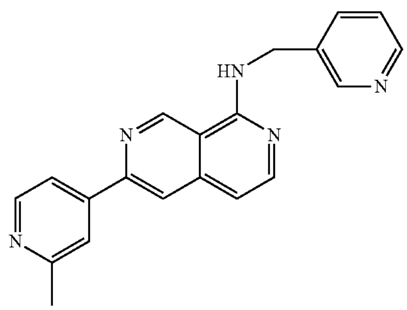 [SMILES: Cc1cc(-c2cc3ccnc(NCc4cccnc4)c3cn2)ccn1] | MS m/z = 328.1 (M + 1); |
| 49 | 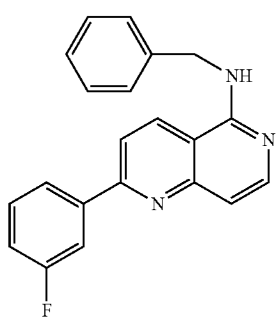 [SMILES: Fc1cccc(-c2ccc3c(NCc4ccccc4)nccc3n2)c1] | MS m/z = 330.1 (M + 1); |
| 50 | 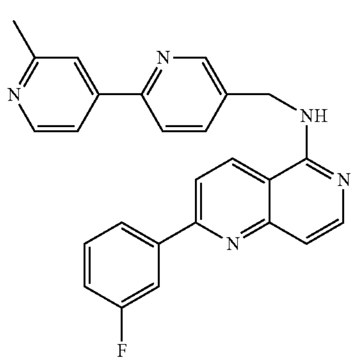 [SMILES: Cc1cc(-c2ccc(CNc3nccc4nc(-c5cccc(F)c5)ccc34)cn2)ccn1] | MS m/z = 422.2 (M + 1); $^1$H NMR (400 MHz, DMSO-d6) δ 8.96 (d, J = 8.4 Hz, 1H), 8.87 (s, 1H), 8.76 (d, J = 6.0 Hz, 1H), 802-8.37 (m, 8H), 7.61-7.67 (m, 1H), 7.42 (t, J = 8.0 Hz, 1H), 7.19 (d, J = 6.4 Hz, 1H), 5.76 (s, 1H), 4.93 (d, J = 5.6 Hz, 2H), 2.69 (s, 3H). |

-continued

| No. | Compound Structure | Compound physical characterization |
|---|---|---|
| 51 | 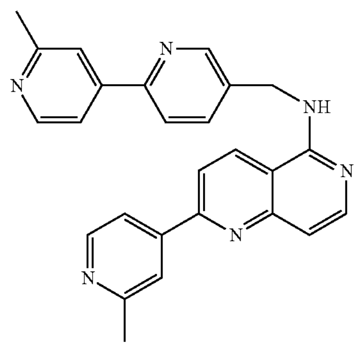 [SMILES: Cc1cc(-c2ccc(CNc3nccc4nc(-c5ccnc(C)c5)ccc34)cn2)ccn1] | MS m/z = 419.2 (M + 1); |
| 52 | 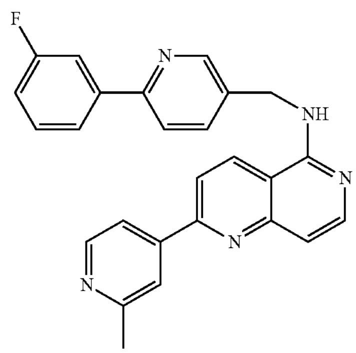 [SMILES: Cc1cc(-c2ccc3c(NCc4ccc(-c5cccc(F)c5)nc4)nccc3n2)ccn1] | MS m/z = 422.2 (M + 1); |
| 53 | 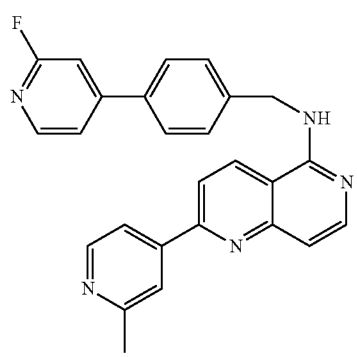 [SMILES: Cc1cc(-c2ccc3c(NCc4ccc(-c5ccnc(F)c5)cc4)nccc3n2)ccn1] | MS m/z = 422.2 (M + 1); |
| 54 | 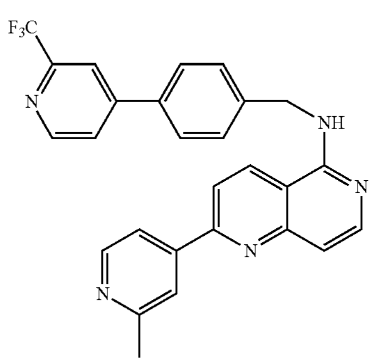 [SMILES: Cc1cc(-c2ccc3c(NCc4ccc(-c5ccnc(C(F)(F)F)c5)cc4)nccc3n2)ccn1] | MS m/z = 472.2 (M + 1); |

| No. | Compound Structure | Compound physical characterization |
|---|---|---|
| 55 | 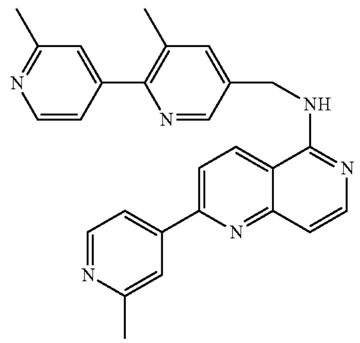 [SMILES: Cc1cc(-c2ccc3c(NCc4cnc(-c5ccnc(C)c5)c(C)c4)nccc3n2)ccn1] | MS m/z = 433.2 (M + 1); |
| 56 | 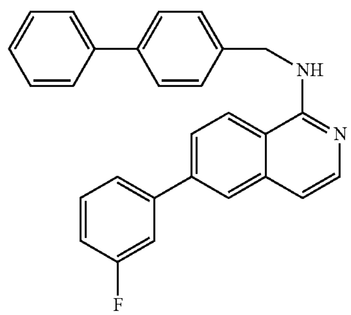 [SMILES: Fc1cccc(-c2ccc3c(NCc4ccc(-c5ccccc5)cc4)nccc3c2)c1] | MS m/z = 405.2 (M + 1); |
| 57 | 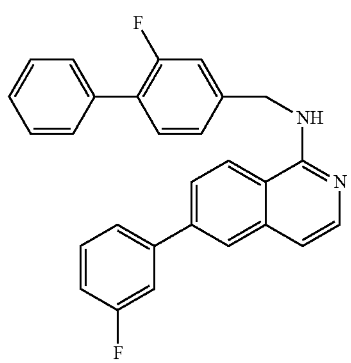 [SMILES: Fc1cccc(-c2ccc3c(NCc4ccc(-c5ccccc5)c(F)c4)nccc3c2)c1] | MS m/z = 423.2 (M + 1); |
| 58 | 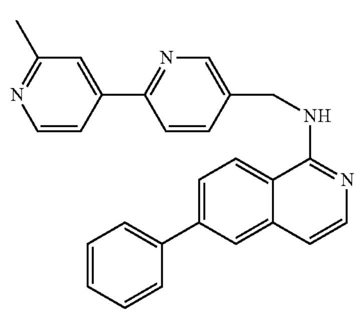 [SMILES: Cc1cc(-c2ccc(CNc3nccc4cc(-c5ccccc5)ccc34)cn2)ccn1] | MS m/z = 403.2 (M + 1); |

-continued

| No. | Compound Structure | Compound physical characterization |
|---|---|---|
| 59 | 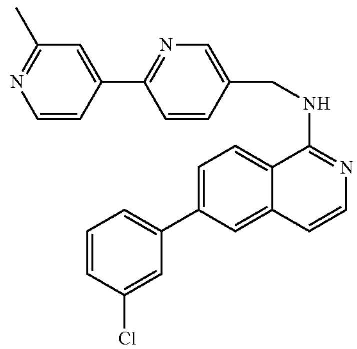 [SMILES: Cc1cc(-c2ccc(CNc3nccc4cc(-c5cccc(Cl)c5)ccc34)cn2)ccn1] | MS m/z = 437.2 (M + 1); |
| 60 | 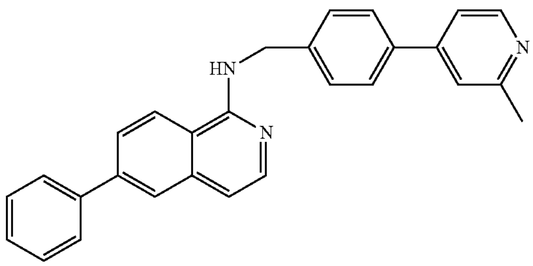 [SMILES: Cc1cc(-c2ccc(CNc3nccc4cc(-c5ccccc5)ccc34)cc2)ccn1] | MS m/z = 402.2 (M + 1); |
| 61 | 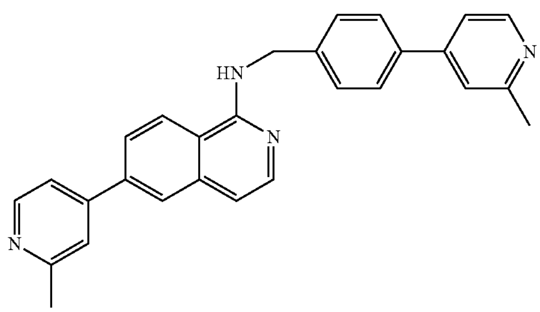 [SMILES: Cc1cc(-c2ccc(CNc3nccc4cc(-c5ccnc(C)c5)ccc34)cc2)ccn1] | MS m/z = 417.2 (M + 1); 1H NMR (300 MHz, CDCl3): δ 2.45 (s, 3H), 2.64 (s, 3H), 4.94 (d, J = 5.10 Hz, 2H), 5.93 (br, 1H), 7.00 (d, J = 5.70 Hz, 1H), 7.32 (d, J = 5.10 Hz, 1H), 7.36 (s, 1H), 7.54 (d, J = 8.10 Hz, 2H), 7.63 (d, J = 8.10 Hz, 2H), 7.80 (m, 2H), 8.20 (d, J = 6.00 Hz, 1H), 8.21 (s, 1H), 8.53 (m, 2H), 9.10 (s, 1H), 9.31 (s, 1H). |
| 62 | 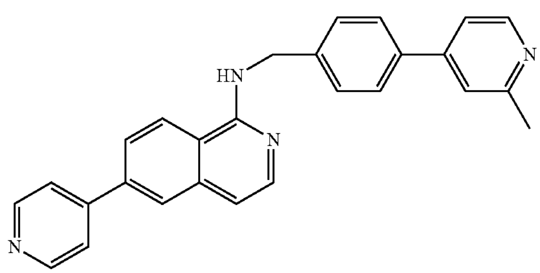 [SMILES: Cc1cc(-c2ccc(CNc3nccc4cc(-c5ccncc5)ccc34)cc2)ccn1] | MS m/z = 403.2 (M + 1); |
| 63 | 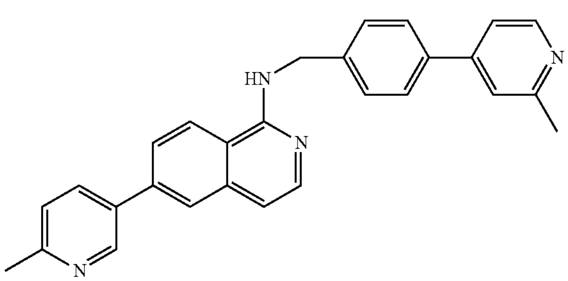 | MS m/z = 417.2 (M + 1); $^1$H NMR (300 MHz, CDCl$_3$): δ 2.63 (s, 3H), 2.65 (s, 3H), 4.93 (d, J = 5.10 Hz, 2H), 7.06 (d, J = 6.00 Hz, 1H), 7.30 (m, 2H), 7.37 (s, 1H), 7.55 (d, J = 8.10 Hz, 2H), 7.63 (d, J = 8.10 Hz, 2H), 7.67 (m, 1H), 7.88 (m, 3H), 8.07 (d, J = 6.00 Hz, 1H), 8.53 (d, J = 5.10 Hz, 1H), 8.82 (d, J = 2.40 Hz, 1H). |

-continued

| No. | Compound Structure | Compound physical characterization |
|---|---|---|
| 64 | 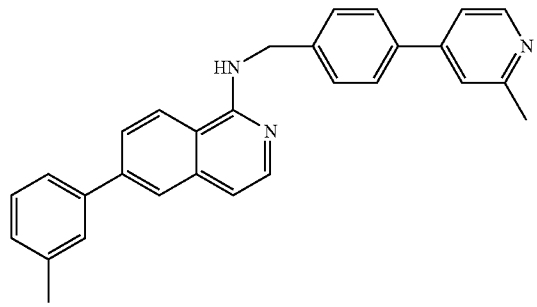 [SMILES: Cc1cccc(-c2ccc3c(NCc4ccc(-c5ccnc(C)c5)cc4)nccc3c2)c1] | MS m/z = 416.2 (M + 1); |
| 65 | 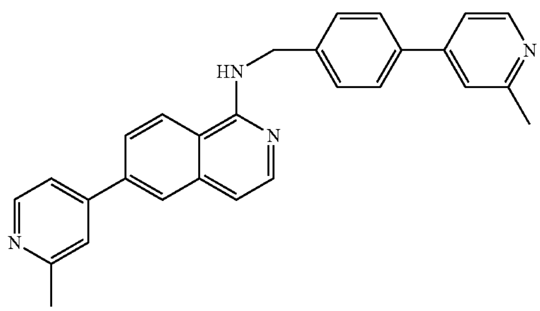 | MS m/z = 417.2 (M + 1); |
| 66 | 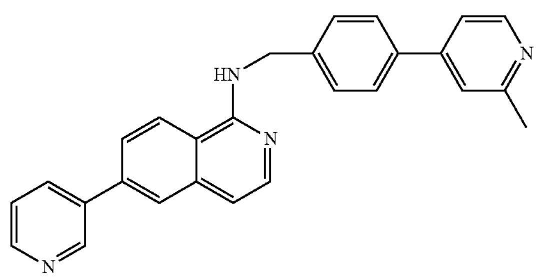 | MS m/z = 403.2 (M + 1); |
| 67 | 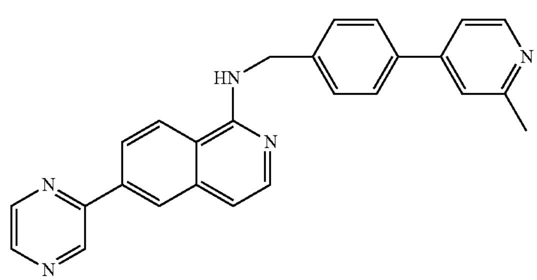 | MS m/z = 404.2 (M + 1); |
| 68 | 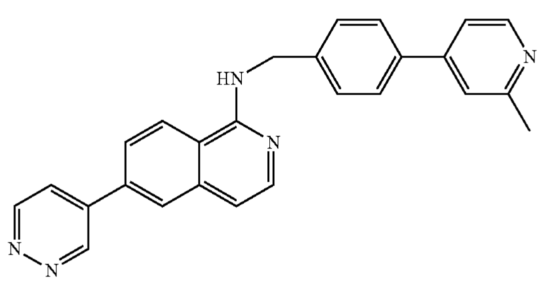 [SMILES: Cc1cc(-c2ccc(CNc3nccc4cc(-c5ccnnc5)ccc34)cc2)ccn1] | MS m/z = 404.2 (M + 1); |

-continued

| No. | Compound Structure | Compound physical characterization |
|---|---|---|
| 69 | 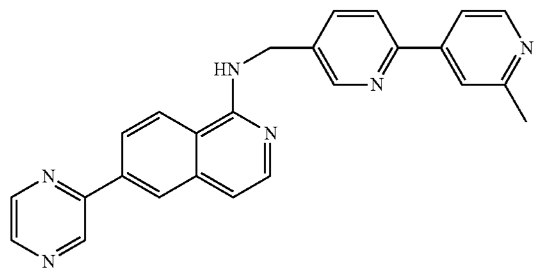 [SMILES: Cc1cc(-c2ccc(CNc3nccc4cc(-c5cnccn5)ccc34)cn2)ccn1] | MS m/z = 405.2 (M + 1); $^1$H NMR (400 MHz, DMSO-d6) δ 9.52 (d, J = 1.2 Hz, 1H), 8.92 (d, J = 2.0 Hz, 1H), 8.84-8.86 (m, 1H), 8.75-8.82 (m, 4H), 8.56 (d, J = 8.8 Hz, 1H), 8.42 (s, 1H), 8.31 (d, J = 8.8 Hz, 2H), 8.12 (d, J = 8.0 Hz, 1H), 7.78 (d, J = 6.8 Hz, 1H), 7.40 (d, J = 6.8 Hz, 1H), 5.76 (s, 1H), 5.00 (d, J = 5.6 Hz, 2H), 2.73 (s, 1H). |
| 70 | 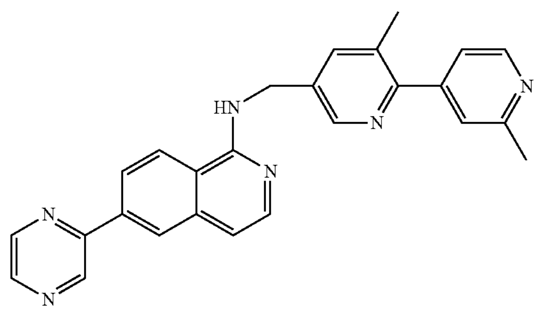 [SMILES: Cc1cc(-c2ncc(CNc3nccc4cc(-c5cnccn5)ccc34)cc2C)ccn1] | MS m/z = 419.2 (M + 1); |
| 71 | 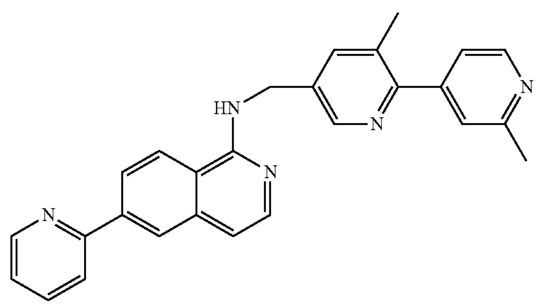 [SMILES: Cc1cc(-c2ncc(CNc3nccc4cc(-c5ccccn5)ccc34)cc2C)ccn1] | MS m/z = 418.2 (M + 1); |
| 72 | 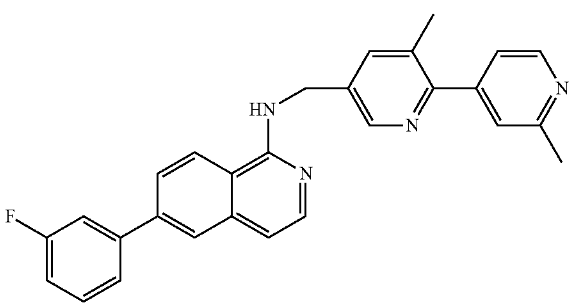 [SMILES: Cc1cc(-c2ncc(CNc3nccc4cc(-c5cccc(F)c5)ccc34)cc2C)ccn1] | MS m/z = 435.2 (M + 1); |
| 73 | 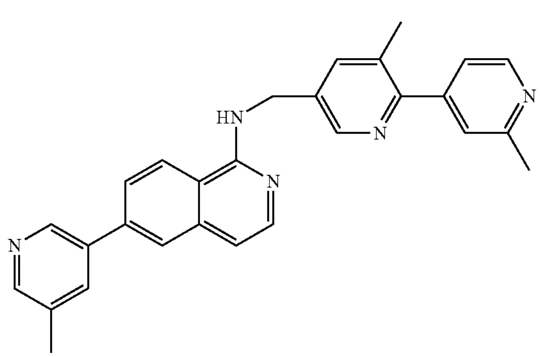 [SMILES: Cc1cncc(-c2ccc3c(NCc4cnc(-c5ccnc(C)c5)c(C)c4)nccc3c2)c1] | MS m/z = 432.2 (M + 1); |

| No. | Compound Structure | Compound physical characterization |
|---|---|---|
| 74 | 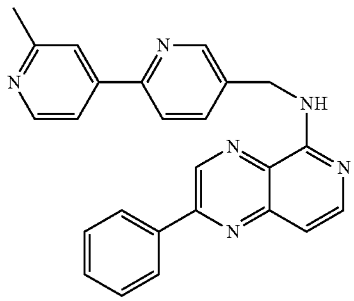 [SMILES: Cc1cc(-c2ccc(CNc3nccc4nc(-c5ccccc5)cnc34)cn2)ccn1] | MS m/z = 405.2 (M + 1); |
| 75 | 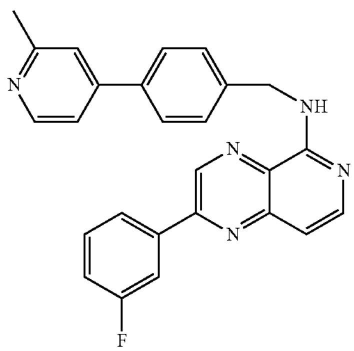 [SMILES: Cc1cc(-c2ccc(CNc3nccc4nc(-c5cccc(F)c5)cnc34)cc2)ccn1] | MS m/z = 422.2 (M + 1); |
| 76 | 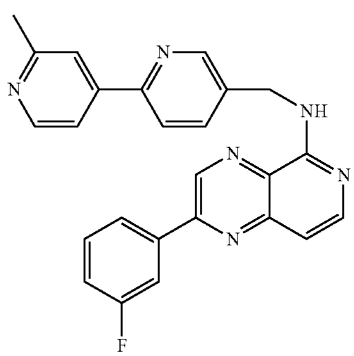 [SMILES: Cc1cc(-c2ccc(CNc3nccc4nc(-c5cccc(F)c5)cnc34)cn2)ccn1] | MS m/z = 423.2 (M + 1); |
| 77 | 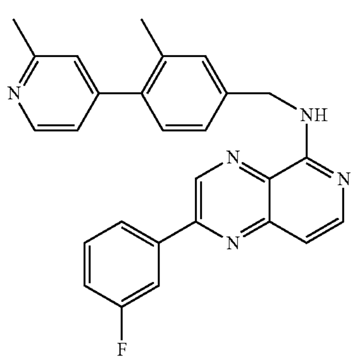 | MS m/z = 436.2 (M + 1); |

-continued

| No. | Compound Structure | Compound physical characterization |
|---|---|---|
| 78 | 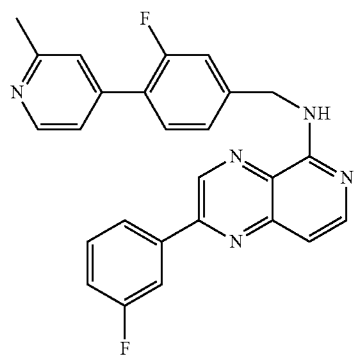 [SMILES: Cc1cc(-c2ccc(CNc3nccc4nc(-c5cccc(F)c5)cnc34)cc2F)ccn1] | MS m/z = 440.2 (M + 1); |
| 79 | 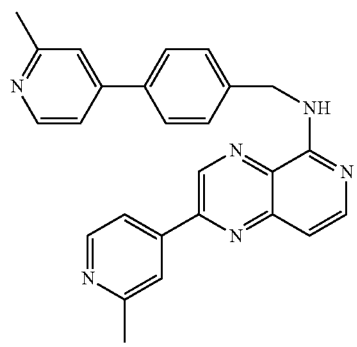 | MS m/z = 419.2 (M + 1); |
| 80 | 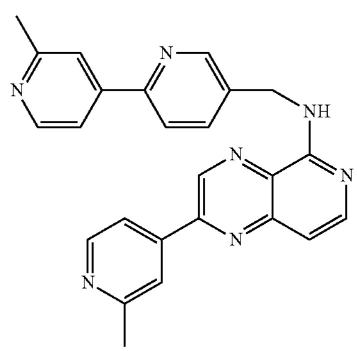 [SMILES: Cc1cc(-c2ccc(CNc3nccc4nc(-c5ccnc(C)c5)cnc34)cn2)ccn1] | MS m/z = 420.2 (M + 1); |
| 81 | 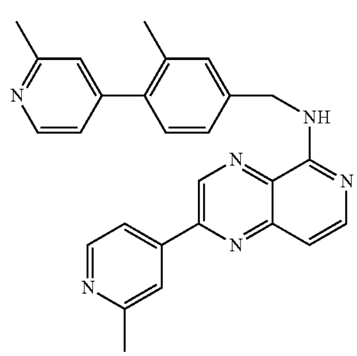 [SMILES: Cc1cc(-c2cnc3c(NCc4ccc(-c5ccnc(C)c5)c(C)c4)nccc3n2)ccn1] | MS m/z = 433.2 (M + 1); |

-continued

| No. | Compound Structure | Compound physical characterization |
|---|---|---|
| 82 | 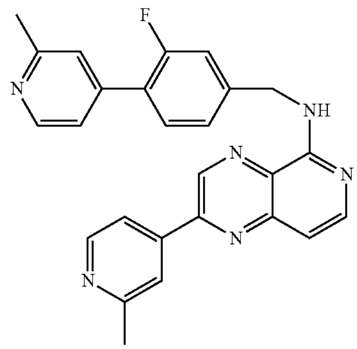 [SMILES: Cc1cc(-c2cnc3c(NCc4ccc(-c5ccnc(C)c5)c(F)c4)nccc3n2)ccn1] | MS m/z = 437.2 (M + 1); |
| 83 | 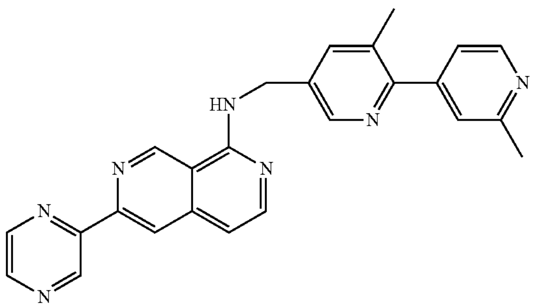 | MS m/z = 420.2 (M + 1); |
| 84 | 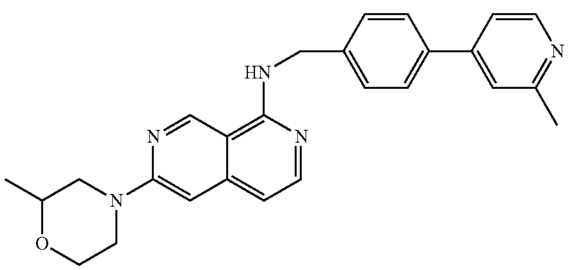 | MS m/z = 426.2 (M + 1); |
| 85 | 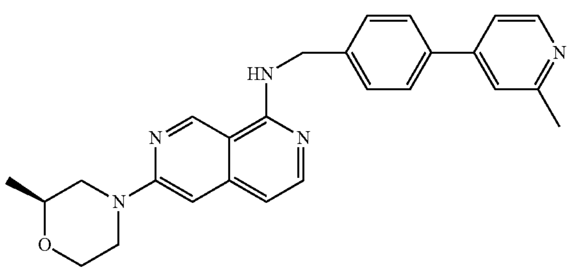 | MS m/z = 426.2 (M + 1); |
| 86 | 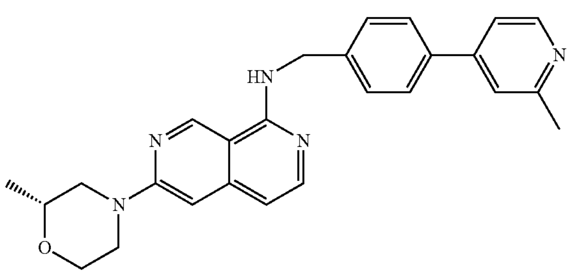 | MS m/z = 426.2 (M + 1); |

| No. | Compound Structure | Compound physical characterization |
|---|---|---|
| 87 | 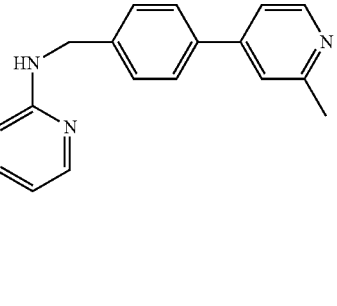 | MS m/z = 453.2 (M + 1); |
| 88 | 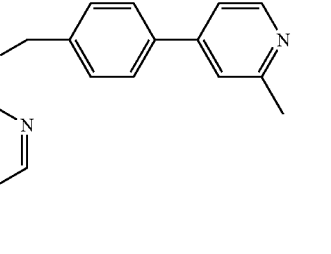 | MS m/z = 393.1 (M + 1); |
| 89 | 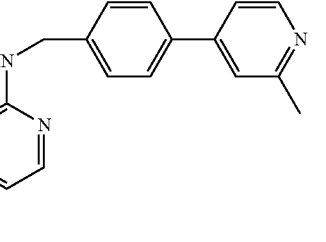 | MS m/z = 407.2 (M + 1); |
| 90 | 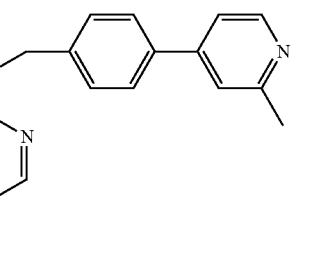 | MS m/z = 395.1 (M + 1); |
| 91 | 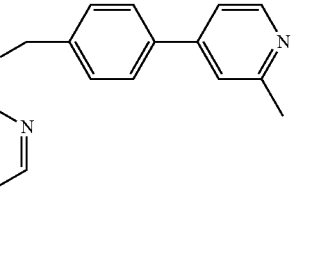 | MS m/z = 409.2 (M + 1); |

| No. | Compound Structure | Compound physical characterization |
|---|---|---|
| 92 | 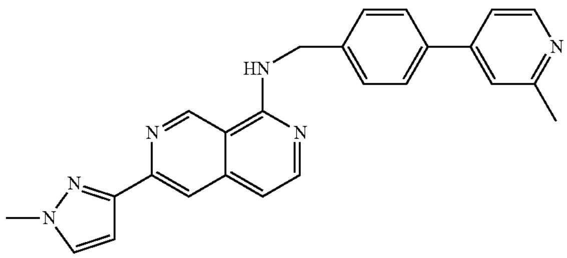 | MS m/z = 407.2 (M + 1); |
| 93 | 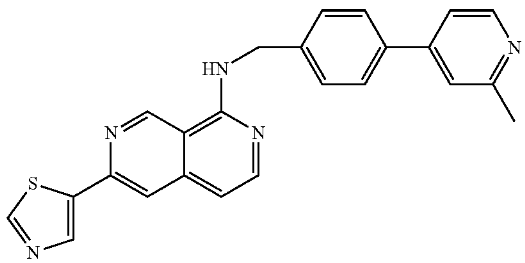 | MS m/z = 410.2 (M + 1); |
| 94 | 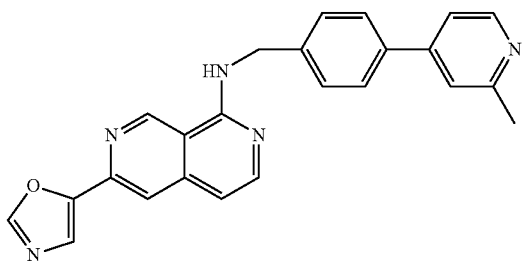 | MS m/z = 394.1 (M + 1); |
| 95 | 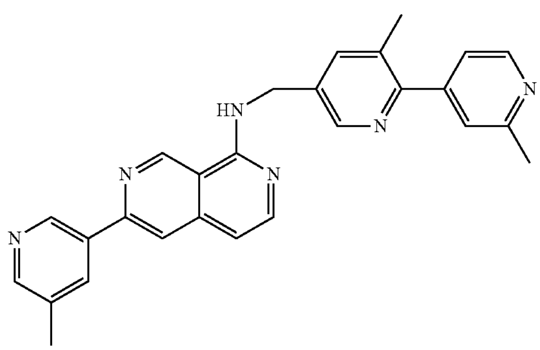 [SMILES: Cc1cncc(-c2cc3ccnc(NCc4cnc(-c5ccnc(C)c5)c(C)c4)c3cn2)c1] | MS m/z = 433.2 (M + 1); |
| 96 | 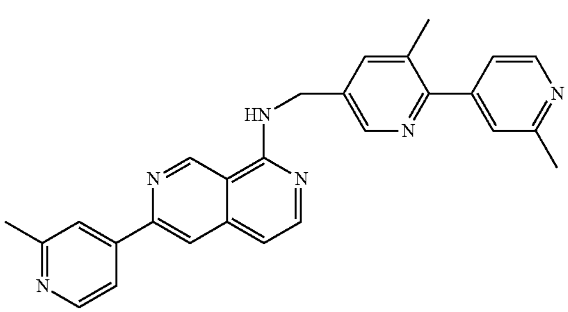 | MS m/z = 433.2 (M + 1); $^1$H NMR (300 MHz, CDCl3): δ 2.30 (s, 3H), 2.55 (s, 3H), 2.61 (s, 3H), 4.86 (d, J = 5.4 Hz, 2H), 5.98 (br, 1H), 6.94 (d, J = 5.7 Hz, 1H), 7.17 (m, 1H), 7.24 (s, 1H), 7.61 (s, 1H), 7.70 (d, J = 5.1 Hz, 1H), 7.79 (s, 1H), 7.89 (s, 1H), 8.14 (d, J = 6.0 Hz, 1H), 8.49 (d, J = 5.1 Hz, 1H), 8.56 (m, 2H), 9.25 (s, 1H). |

-continued

| No. | Compound Structure | Compound physical characterization |
|---|---|---|
| 97 | 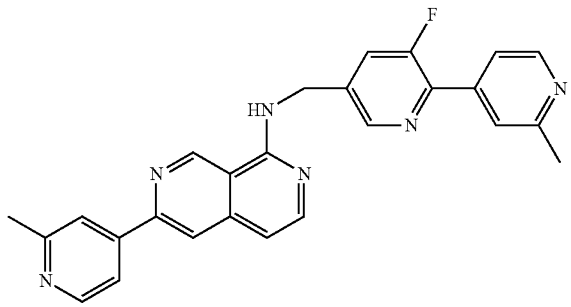 | MS m/z = 437.2 (M + 1); $^1$H NMR (300 MHz, CDCl3): δ 2.31 (s, 3H), 2.61 (s, 3H), 4.90 (d, J = 5.4 Hz, 2H), 6.00 (br, 1H), 6.94 (d, J = 5.7 Hz, 1H), 7.18 (m, 1H), 7.24 (s, 1H), 7.63 (s, 1H), 7.70 (d, J = 5.1 Hz, 1H), 7.80 (s, 1H), 7.90 (s, 1H), 8.14 (d, J = 6.0 Hz, 1H), 8.33 (s, 1H), 8.50 (d, J = 5.1 Hz, 1H), 8.54 (m, 1H), 9.25 (s, 1H). |
| 98 | 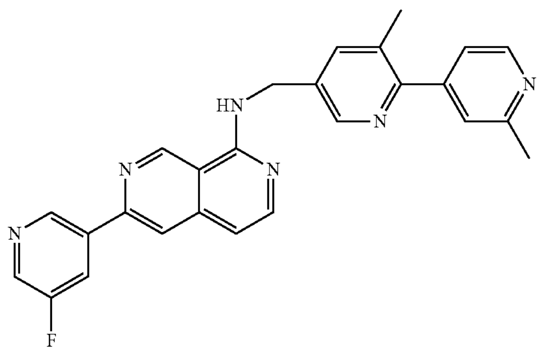 [SMILES: Cc1cc(-c2ncc(CNc3nccc4cc(-c5cncc(F)c5)ncc34)cc2C)ccn1] | MS m/z = 437.2 (M + 1); |
| 99 | 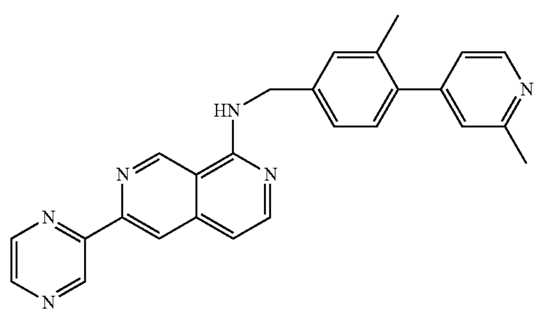 [SMILES: Cc1cc(-c2ccc(CNc3nccc4cc(-c5cnccn5)ncc34)cc2C)ccn1] | MS m/z = 419.2 (M + 1); |
| 100 | 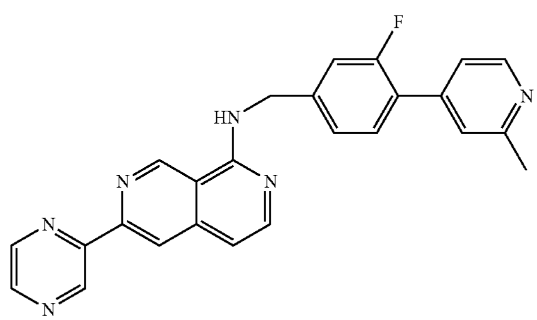 [SMILES: Cc1cc(-c2ccc(CNc3nccc4cc(-c5cnccn5)ncc34)cc2F)ccn1] | MS m/z = 423.2 (M + 1); |
| 101 | 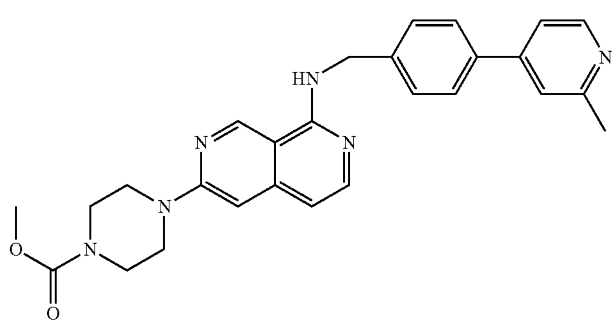 [SMILES: COC(=O)N1CCN(c2cc3ccnc(NCc4ccc(-c5ccnc(C)c5)cc4)c3cn2)CC1] | MS m/z = 469.2 (M + 1); |

| No. | Compound Structure | Compound physical characterization |
|---|---|---|
| 102 | 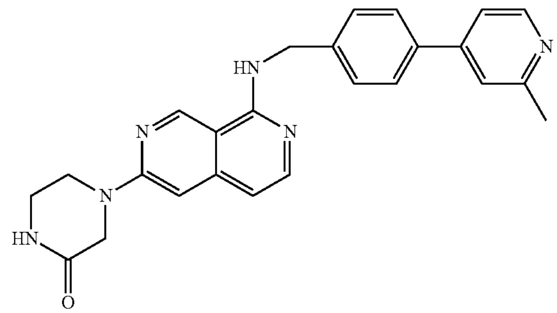 [SMILES: Cc1cc(-c2ccc(CNc3nccc4cc(N5CCNC(=O)C5)ncc34)cc2)ccn1] | MS m/z = 425.2 (M + 1); |
| 103 | 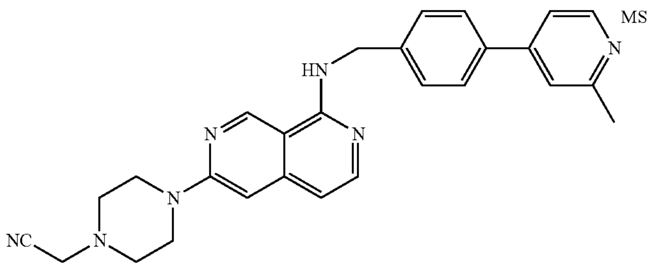 | MS m/z = 450.2 (M + 1); |
| 104 | 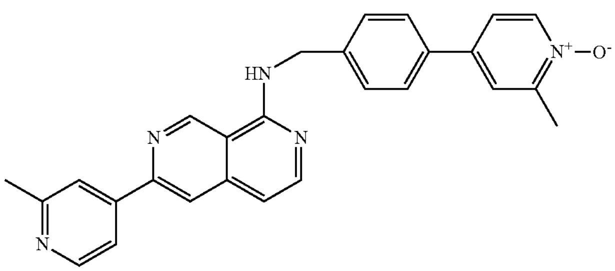 [SMILES: Cc1cc(-c2cc3ccnc(NCc4ccc(-c5cc[n+]([O-])c(C)c5)cc4)c3cn2)ccn1] | MS m/z = 434.2 (M + 1); |
| 105 | 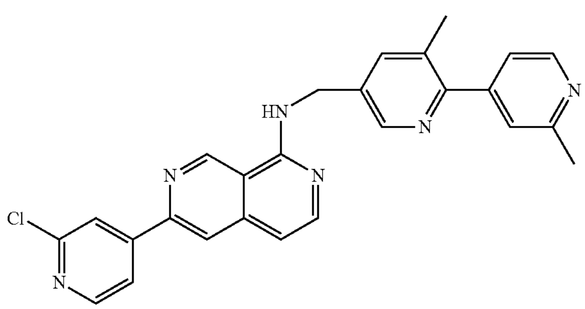 [SMILES: Cc1cc(-c2ncc(CNc3nccc4cc(-c5ccnc(Cl)c5)ncc34)cc2C)ccn1] | MS m/z = 453.2 (M + 1); |
| 106 | 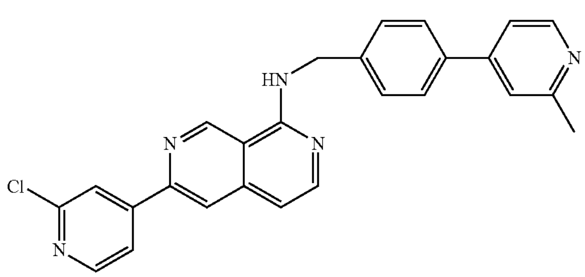 [SMILES: Cc1cc(-c2ccc(CNc3nccc4cc(-c5ccnc(Cl)c5)ncc34)cc2)ccn1] | MS m/z = 438.2 (M + 1); |

| No. | Compound Structure | Compound physical characterization |
|---|---|---|
| 107 | 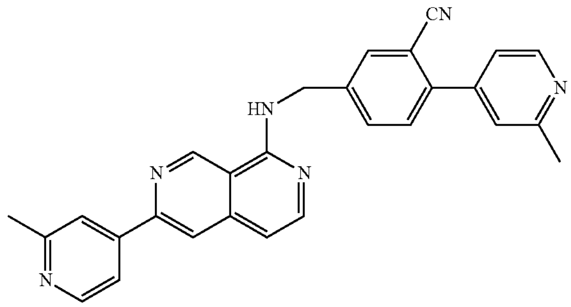 | MS m/z = 443.2 (M + 1); $^1$H NMR (300 MHz, CDCl3): δ 2.30 (s, 3H), 2.61 (s, 3H), 4.98 (d, J = 5.7 Hz, 2H), 6.00 (br, 1H), 7.03 (d, J = 5.70 Hz, 1H), 7.35 (s, 1H), 7.45 (d, J = 7.8 Hz, 2H), 7.62 (s, 1H), 7.79 (d, J = 5.1 Hz, 2H), 7.89 (s, 1H), 7.98 (s, 1H), 8.20 (d, J = 5.70 Hz, 1H), 8.56 (d, J = 5.10 Hz, 2H), 8.66 (d, J = 5.10 Hz, 2H), 9.30 (s, 1H). |
| 108 | 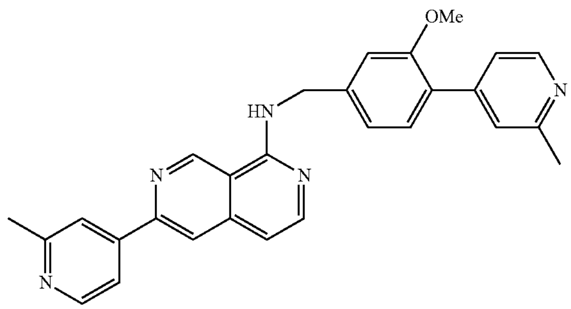 | MS m/z = 448.2 (M + 1); |
| 109 | 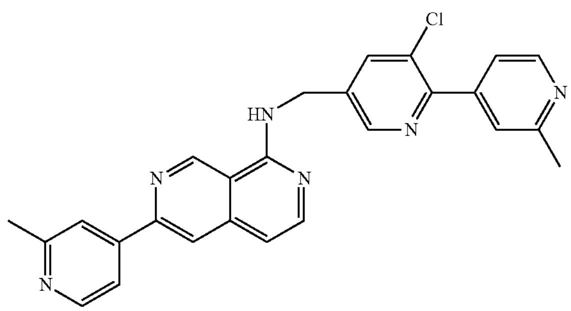 | MS m/z = 453.2 (M + 1); |
| 110 | 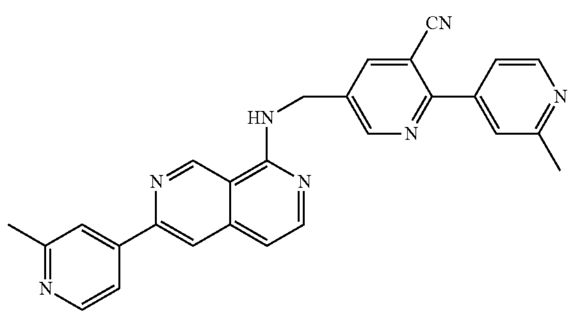 | MS m/z = 444.2 (M + 1); |
| 111 | 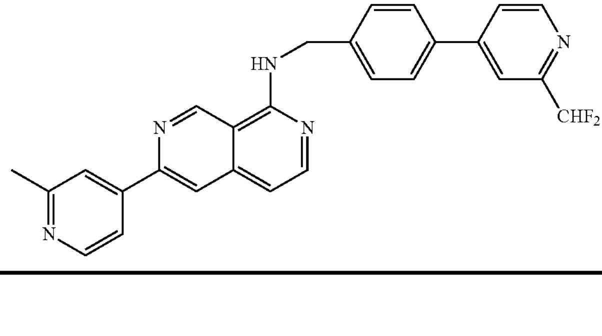 | MS m/z = 454.2 (M + 1); |

Example 6

WNT Pathway Reporter Gene Assay

Materials and Methods:

NIH3T3 mouse fibroblast cells (American Type Culture Collection, Manassas, Va.) were transfected with a plasmid containing a luciferase gene driven by 5 copies of TCF elements. Stale cells selected with 1 µg/mL of Zeocin (Gibco/Invitrogen, Carlsbad, Calif.) are cultured in Dulbecco's modified Eagle's medium (Invitrogen, Carlsbad, Calif.) supplemented with 10% FBS (Invitrogen), 50 unit/mL penicillin and 50 µg/mL of streptomycin (Invitrogen) at 37° C. with 5% CO2 in air atmosphere. Suspension HEK293 cells (ATCC) were transfected with a plasmid containing full-length human WNT-3a cDNA sequence driven by a CMV promoter, and stable cells were selected in FreeStyle 293 medium (Invitrogen) supplemented with 100 ug/mL G418.

The NIH3T3 TCF-Luc cells and 293 WNT3a cells were co-cultured in a 96-well plate with DMEM medium supplemented with 0.5% FBS. After 16 hours, the firefly luciferase activities are measured with the Steady-Glo™ Luciferase Assay System (Promega). The cells were treated with different concentrations of compounds of this invention during the co-culture. The IC50s were defined as the concentration when the compounds reduce the luminescence intensity by 50%. To normalize for cell quantity and viability, CellTiter Glo assay is next performed in a duplicate plate.

All compounds presented in the patent have $IC_{50}<5$ µM in WNT pathway reporter gene assay. Selective examples were listed in the table below.

| Compound No. | IC50 (µM) |
|---|---|
| 1 | <0.003 |
| 2 | <0.003 |
| 3 | 0.010 |
| 4 | 0.005 |
| 5 | 0.070 |
| 9 | 0.010 |
| 14 | 0.003 |
| 16 | 0.015 |
| 20 | 0.050 |
| 22 | 0.005 |
| 23 | 0.020 |
| 28 | <0.003 |
| 33 | 0.050 |
| 35 | <0.003 |
| 37 | 0.020 |
| 39 | 0.070 |
| 47 | 1.25 |
| 50 | 0.035 |
| 61 | 0.005 |
| 63 | 0.005 |
| 68 | 0.025 |
| 69 | 0.015 |
| 70 | <0.003 |
| 75 | 0.005 |
| 84 | 0.015 |
| 96 | 0.001 |
| 97 | 0.001 |
| 104 | 0.005 |
| 107 | 0.008 |
| 109 | 0.002 |

Example 7

Mechanistic Studies of the WNT Pathway Inhibitors

Compounds that inhibited the TCF reporter gene activity induced by the co-cultured Wnt-3a cells in the primary assay were followed up in a mechanistic study to identify the point of action of the compounds. Two different of activators were assessed, one with purified recombinant Wnt-3a protein (StemRD Inc., Burlingame, Calif.), the other with a GSK-3b inhibitor 6-bromoindirubin-3'-oxime (StemRD Inc., Burlingame, Calif.).

Results of such mechanistic studies showed that some of the active compounds in this invention inhibit WNT pathway activation at a point before the WNT-3a interaction with the receptors, as they did not inhibit the TCF reporter gene activation by recombinant WNT-3a protein. The candidates of such action include, but are not limited to wntless/ evenness interrupted (Wls/Evi), porcupine (Porcn), and Vps35p.

Example 5

Effect of WNT Pathway Inhibitors on Cancer Cells

Compounds that inhibit Wnt secretion and intracellular signal transduction are expected to inhibit proliferation of cancer cells that depend on autocrine Wnt signaling. The effect of the Wnt pathway inhibitors on cell proliferation in 2-D culture, anchorage independent growth and apoptosis resistance in cell lines known to require Wnt autocrine signaling. Compounds are evaluated by using standard assays on the Wnt dependent cell lines known in the published literature: PA-1 (ovarian teratocarcinoma cancer), MDA-MB-157 (breast cancer), Saos-2 (osteosarcoma) and SNU1076 (head and neck squamous carcinoma). Effects of the inhibitors are seen in these cell lines, further confirming the activities expected for the compounds.

REFERENCE

Akiri G, Cherian M M, Vijayakumar 5, Liu G, Bafico A, Aaronson S A. Wnt pathway aberrations including autocrine Wnt activation occur at high frequency in human non-small-cell lung carcinoma. Oncogene. 2009 May 28; 28(21):2163-72.

Bafico A, Liu G, Goldin L, Harris V, Aaronson S A. An autocrine mechanism for constitutive Wnt pathway activation in human cancer cells. Cancer Cell. 2004 November; 6(5):497-506.

Barker N, Clevers H. Mining the Wnt pathway for cancer therapeutics. Nat Rev Drug Discov. 2006 December; 5(12):997-1014.

Blom A B, van Lent P L, van der Kraan P M, van den Berg W B. To seek shelter from the WNT in osteoarthritis? WNT-signaling as a target for osteoarthritis therapy. Curr Drug Targets. 2010 May; 11(5):620-9.

Boonen R A, van Tijn P, Zivkovic D. Wnt signaling in Alzheimer's disease: up or down, that is the question. Ageing Res Rev. 2009 April; 8(2):71-82.

Camilli T C, Weeraratna A T. Striking the target in Wnt-y conditions: intervening in Wnt signaling during cancer progression. Biochem Pharmacol. 2010 Sep. 1; 80(5): 702-11.

Chan S L, Cui Y, van Hasselt A, Li H, Srivastava G, Jin H, Ng K M, Wang Y, Lee K Y, Tsao G S, Zhong S, Robertson K D, Rha S Y, Chan A T, Tao Q. The tumor suppressor Wnt inhibitory factor 1 is frequently methylated in nasopharyngeal and esophageal carcinomas. Lab Invest. 2007 July; 87(7): 644-50.

Chen B, Dodge M E, Tang W, Lu J, Ma Z, Fan C W, Wei S, Hao W, Kilgore J, Williams N S, Roth M G, Amatruda J F, Chen C, Lum L. Small molecule-mediated disruption of Wnt-dependent signaling in tissue regeneration and cancer. Nat Chem Biol. 2009 February; 5(2):100-7.

Cheng J H, She H, Han Y P, Wang J, Xiong S, Asahina K, Tsukamoto H. Wnt antagonism inhibits hepatic stellate cell activation and liver fibrosis. Am J Physiol Gastrointest Liver Physiol. 2008; 294(1):G39-49.

Chun J S, Oh H, Yang S, Park M. Wnt signaling in cartilage development and degeneration. BMB Rep. 2008 Jul. 31; 41(7):485-94.

Chien A J, Moon R T. WNTS and WNT receptors as therapeutic tools and targets in human disease processes. Front Biosci. 2007 Jan. 1; 12:448-57.

DeAlmeida V I, Miao L, Ernst J A, Koeppen H, Polakis P, Rubinfeld B. The soluble wnt receptor Frizzled-8CRD-hFc inhibits the growth of teratocarcinomas in vivo. Cancer Res. 2007 Jun. 1; 67(11):5371-9

D'Amour K A, Bang A G, Eliazer S, Kelly O G, Agulnick A D, Smart N G, Moorman M A, Kroon E, Carpenter M K, Baetge E E. Production of pancreatic hormone-expressing endocrine cells from human embryonic stem cells. Nat Biotechnol. 2006 November; 24(11):1392-401.

Herbst A, Kolligs F T. Wnt signaling as a therapeutic target for cancer. Method Mol 2007; 361:63-91.

Hoeppner L H, Secreto F J, Westendorf J J. Wnt signaling as a therapeutic target for bone diseases. Expert Opin Ther Targets. 2009 April; 13(4):485-96.

Hwang I, Seo E Y, Ha H. Wnt/beta-catenin signaling: a novel target for therapeutic intervention of fibrotic kidney disease. Arch Pharm Res. 2009 December; 32(12):1653-62.

Inestrosa N C, Arenas E. Emerging roles of Wnts in the adult nervous system. Nat Rev Neurosci. 2010 February; 11(2): 77-86.

Lie D C, Colamarino S A, Song H J, Desire L, Mira H, Consiglio A, Lein E S, Jessberger S, Lansford H, Dearie A R, Gage F H. WNT signalling regulates adult hippocampal neurogenesis. Nature 437 (7063): 1370-5, 2005.

Kansara M, et al. Wnt inhibitory factor 1 is epigenetically silenced in human osteosarcoma, and targeted disruption accelerates osteosarcomagenesis in mice. J Clin Invest. 2009 April; 119(4):837-51

MacDonald B T, Tamai K, He X. Wnt/beta-catenin signaling: components, mechanisms, and diseases. Dev Cell. 2009 July; 17(1):9-26.

Mikels A J, Nusse R. Wnts as ligands: processing, secretion and reception. Oncogene. 2006 Dec. 4; 25(57):7461-8.

Moon R T. Wnt/beta-catenin pathway. Sci STKE.; 2005 (271):cm1.

Morrisey E E. Wnt signaling and pulmonary fibrosis. Am J Pathol. 2003 May; 162(5): 1393-7.

Nusse R. WNT signaling and stein cell control". Cell Res. 18 (5): 823-7, 2008

Ouchi N, Higuchi A, Ohashi K, Oshima Y, Gokce N, Shibata R, Akasaki Y, Shimono A, Walsh K. Sfrp5 is an anti-inflammatory adipokine that modulates metabolic dysfunction in obesity. Science. 2010 Jul. 23; 329(5990):454-7.

Reya T, Clevers H. Wnt signalling in stem cells and cancer. Nature. 2005 Apr. 14; 434(7035):843-50.

Rhee C S, Sen M, Lu D, Wu C, Leoni L, Rubin J, Corr M, Carson D A. Wnt and frizzled receptors as potential targets for immunotherapy in head and neck squamous cell carcinomas. Oncogene. 2002 Sep. 26; 21(43):6598-605.

Sullivan G J, et al. Generation of functional human hepatic endoderm from human induced pluripotent stem cells. Hepatology. 2010 January; 51(1):329-35.

Takahashi-Yanaga F, Kahn M. Targeting Wnt signaling: can we safely eradicate cancer stem cells? Clin Cancer Res. 2010 Jun. 15; 16(12):3153-62.

Ten Berge, D. et al. WNT signaling mediates self-organization and axis formation in embryoid bodies. Cell Stem Cell 3, 508-518, 2008.

Yang L, Soonpaa M H, Adler E D, Roepke T K, Kattman S J, Kennedy M, Henckaerts E, Bonham K, Abbott G W, Linden R M, Field L J, Keller G M. Human cardiovascular progenitor cells develop from a KDR+embryonic-stem-cell-derived population. Nature. 2008 May 22; 453 (7194):524-8.

The invention claimed is:

1. A compound, having the structure of Formula I:

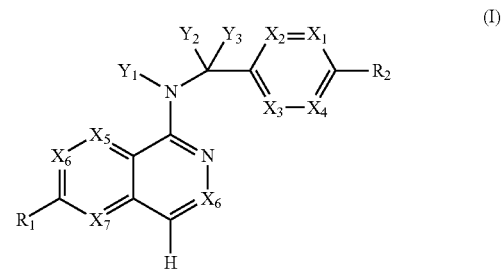

or a physiologically acceptable salt thereof, wherein $X_1$, $X_2$, $X_3$, $X_4$, and $X_6$ are independently $CR_4$ or N;

$X_5$, $X_7$, and $X_8$ are $CR_4$;

$Y_1$ is hydrogen or —$C(R_4)_3$, each $R_4$ is same or different;

$Y_2$ and $Y_3$ are independently hydrogen, halogen or —$C(R_3)_3$, each $R_3$ is same or different;

$R_1$ is selected from hydrogen, halogen, $C_{1-6}$ alkyl, quinolinyl,

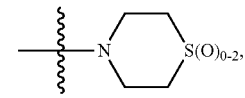

$C_{6-30}$ aryl, 3 to 6 membered heterocycloalkyl containing 1-2 heteroatoms selected from N, O and S, and 5 or 6 membered heteroaryl containing 1-4 heteroatoms selected from N, O and S, wherein each of quinolinyl,

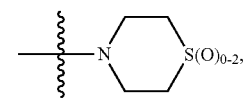

$C_{6-30}$ aryl, 3 to 6 membered heterocycloalkyl, and 5 or 6 membered heteroaryl can be optionally substituted with one or two, and same or different $R_4$;

$R_2$ is selected from halogen, $C_{1-6}$ alkyl, quinolinyl,

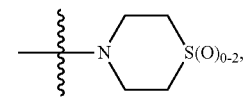

$C_{6-30}$ aryl, 3 to 6 membered heterocycloalkyl containing 1-2 heteroatoms selected from N, O and S, and 5 or 6 membered heteroaryl containing 1-4 heteroatoms selected from N, O and S, wherein each of quinolinyl;

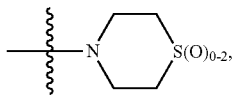

$C_{6-30}$ aryl, 3 to 6 membered heterocycloalkyl, and 5 or 6 membered heteroaryl can be optionally substituted with one or two, and same or different $R_4$;
wherein, if $X_6$ is $CR_4$, $R_2$ is quinolinyl,

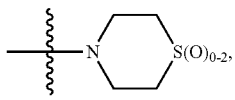

unsubstituted $C_{6-30}$ aryl, 3 to 6 membered heterocycloalkyl containing 1-2 heteroatoms selected from N O and S or 5 or 6 membered heteroaryl containing 1-4 heteroatoms selected from N, O and S, wherein each of quinolinyl;

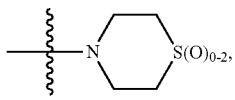

3 to 6 membered heterocycloalkyl, or 5 or 6 membered heteroaryl can be optionally substituted with one or two, and same or different $R_4$;
  each $R_3$ is independently selected from hydrogen, halogen, cyano, $C_{1-6}$ alkyl, and $C_{1-6}$ alkoxy, wherein each of the $C_{1-6}$ alkyl and $C_{1-6}$ alkoxy can be optionally substituted with halo, amino, hydroxyl, $C_{1-6}$ alkoxy or cyano;
  each $R_4$ is independently selected from hydrogen, halogen, cyano, $C_{1-6}$ alkoxy, —$S(O)_2R_5$, —$C(O)OR_5$, —$C(O)R_5$, —$C(O)NR_6R_7$, $C_{1-6}$ alkyl, $C_{2-6}$ alkenyl and $C_{2-6}$ alkynyl, wherein each of $C_{1-6}$ alkoxy, —$S(O)_2R_5$, —$C(O)OR_5$, —$C(O)R_5$, —$C(O)NR_6R_7$, $C_{1-6}$ alkyl, $C_{2-6}$ alkenyl and $C_{2-6}$ alkynyl can be optionally substituted with halo, amino, hydroxyl, $C_{1-6}$ alkoxy or cyano;
  $R_5$, $R_6$ and $R_7$ are independently selected from hydrogen, $C_{1-6}$ alkyl, $C_{2-6}$ alkenyl and $C_{2-6}$ alkynyl, in which each of the $C_{1-6}$ alkyl, $C_{2-6}$ alkenyl and $C_{2-6}$ alkynyl can be optionally substituted with halo, amino, hydroxyl, $C_{1-6}$ alkoxy or cyano.

2. The compound of claim 1, wherein the core structure of Formula I defined by $X_5$, $X_6$, $X_7$ and $X_8$ is selected from:

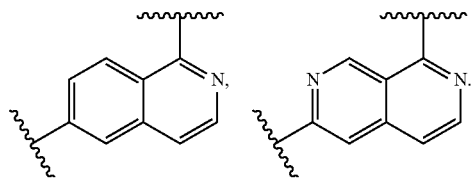 [SMILES: *c1ccc2c(*)nccc2c1 ; *c1cc2ccnc(*)c2cn1]

3. The compound of claim 1, wherein the ring in Formula I defined by $X_1$, $X_2$, $X_3$ and $X_4$ is selected from:

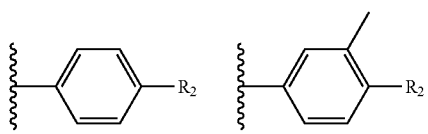

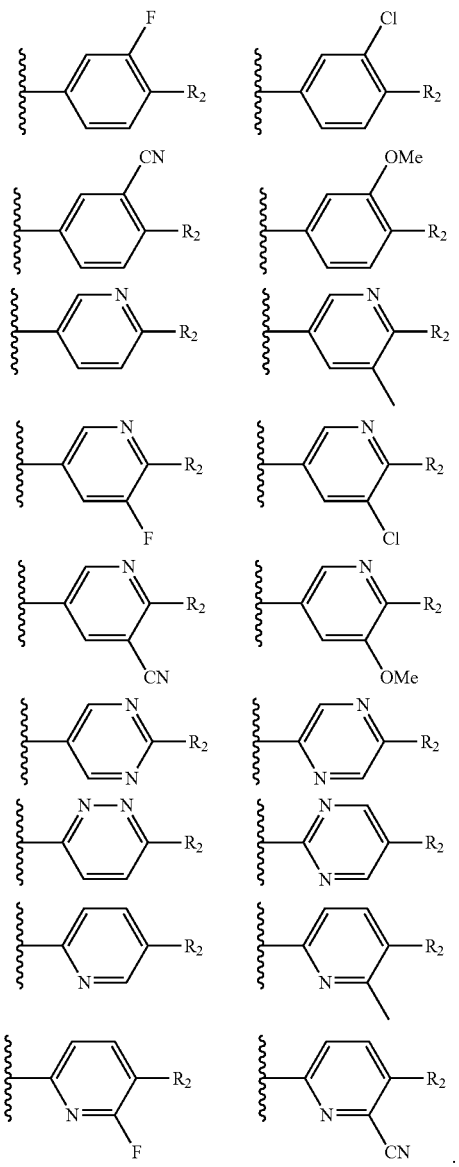

4. The compound of claim 2, wherein $R_1$ and $R_2$ are independently selected from hydrogen, fluorine, chlorine, methyl,

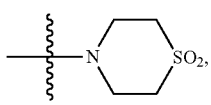

phenyl, morpholinyl, piperazinyl, and the 5 or 6 membered heteroaryl is selected from:

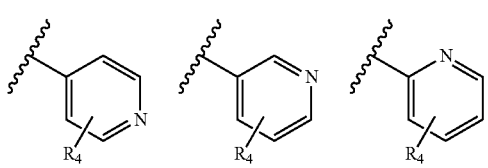

-continued

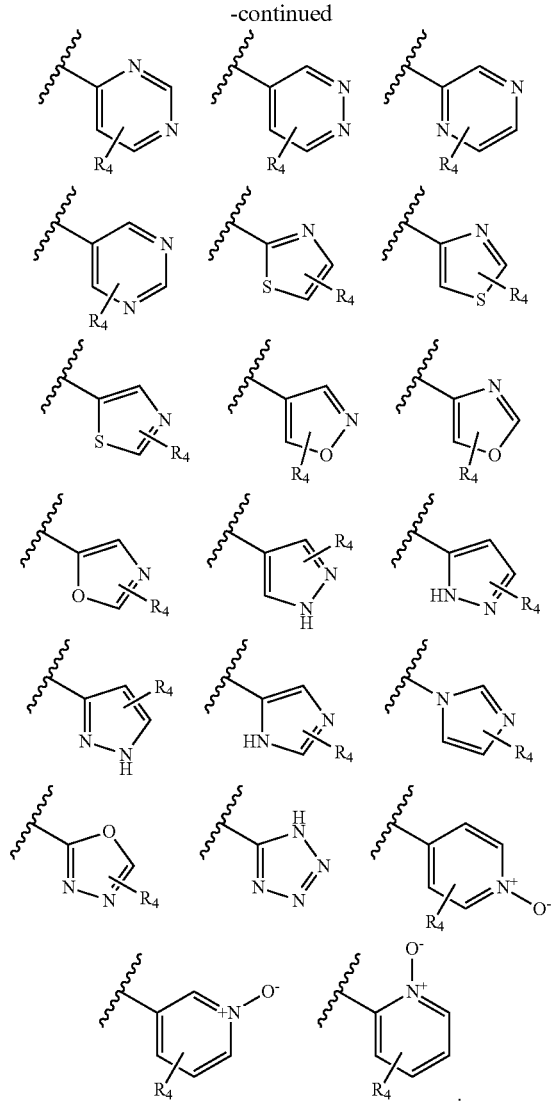

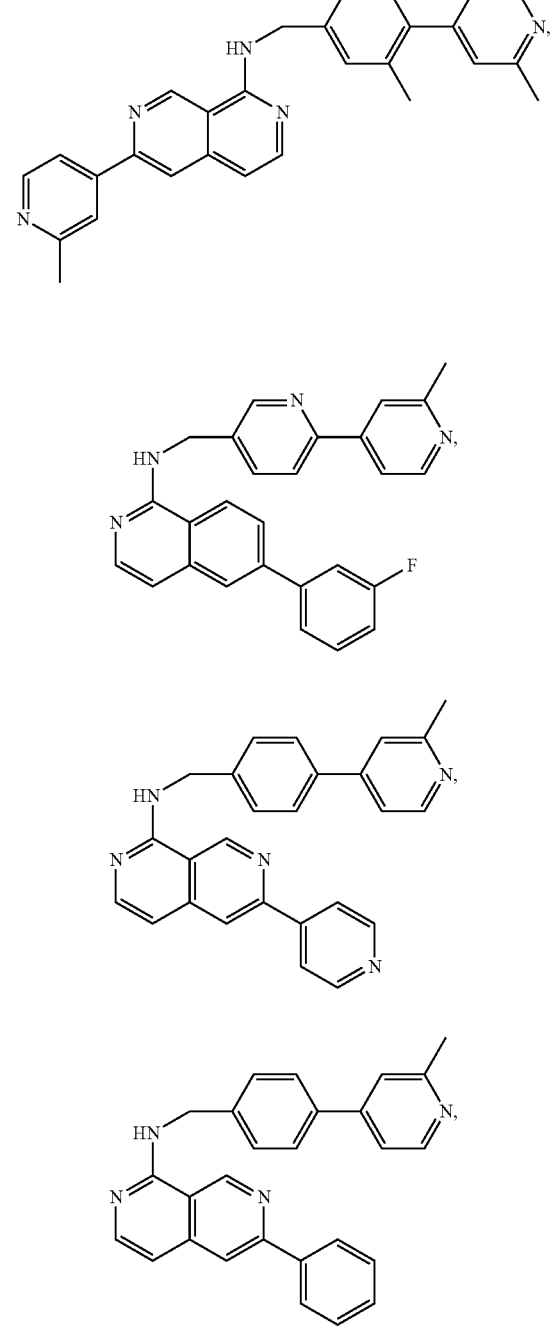

5. The compound of claim 2, wherein each $R_4$ is independently selected from hydrogen, chlorine, fluorine, cyano, —$CH_3$, —$CHF_2$, —$CF_3$, —$OCH_3$, —$COOCH_3$.

6. The compound of claim 2, wherein at least one atom in Formula I is at least one of corresponding isotope(s) selected from $^2H$, $^3H$, $^{11}C$, $^{13}C$, $^{14}C$, $^{15}N$, $^{17}O$, $^{18}O$, $^{35}S$, $^{18}F$, $^{36}Cl$ and $^{123}I$.

7. The compound of claim 1, being selected from:

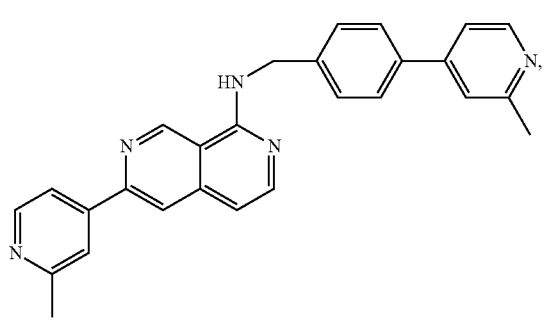

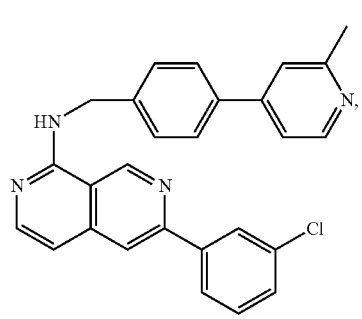

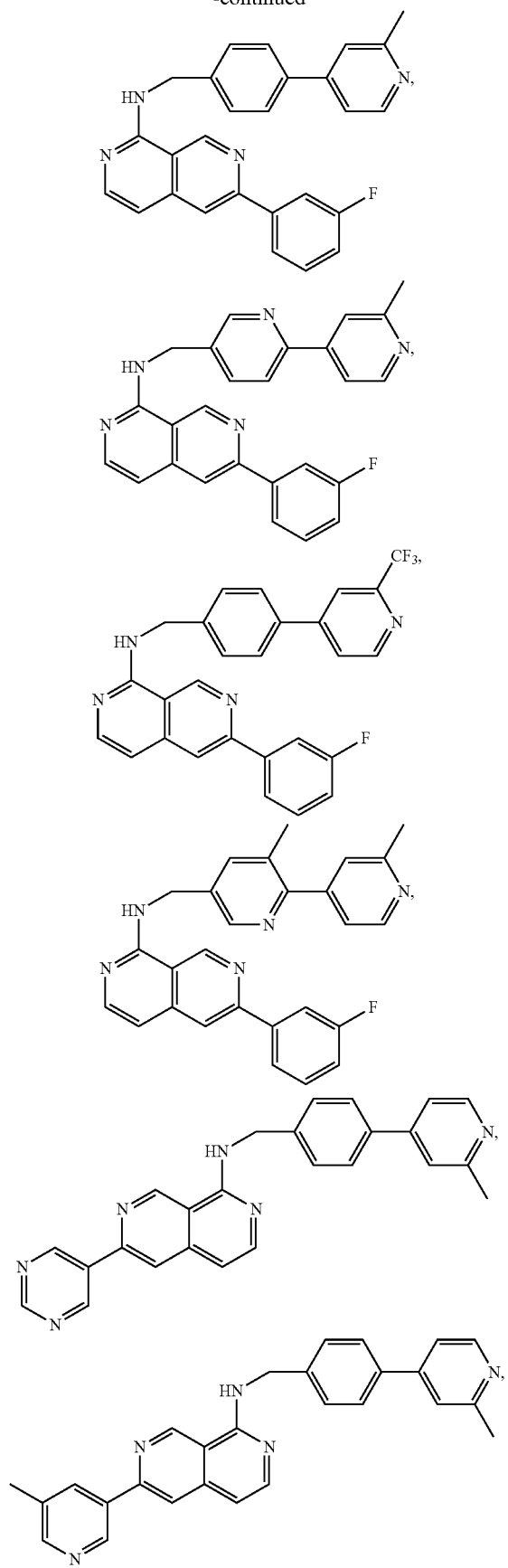
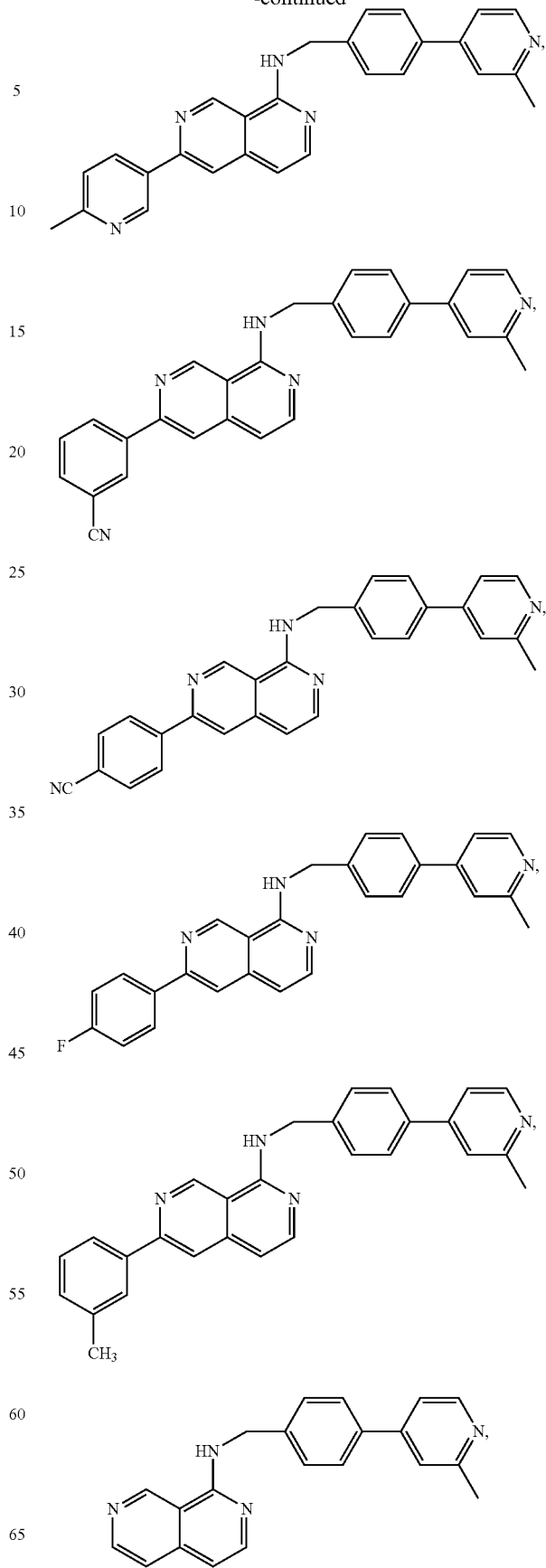

85
-continued
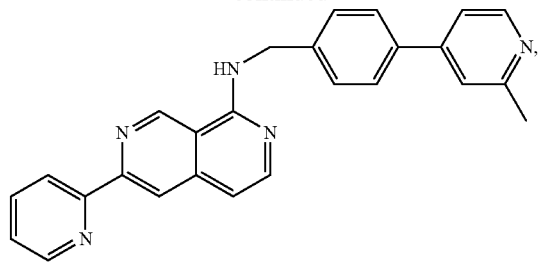
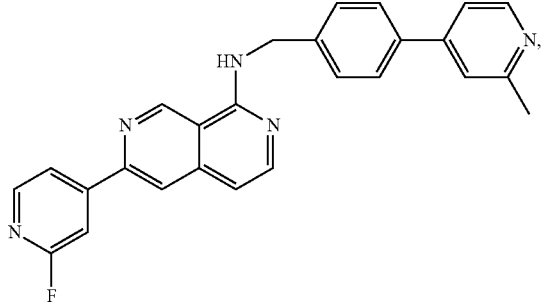
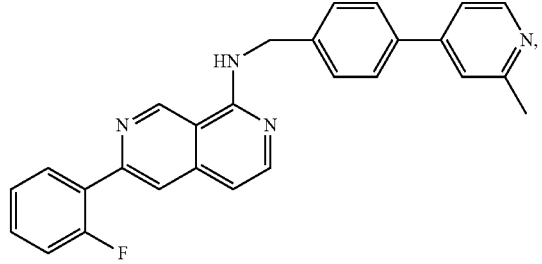
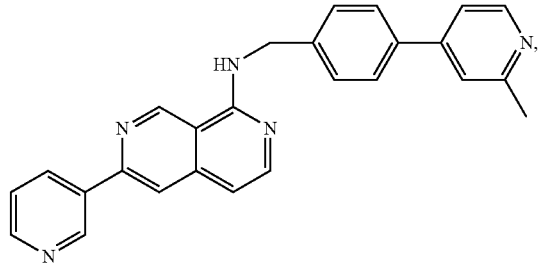
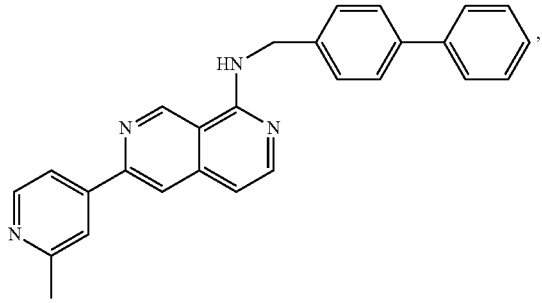
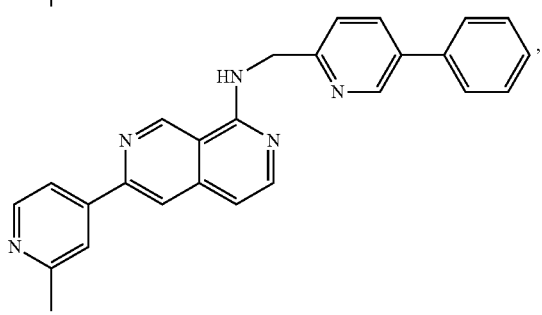
86
-continued
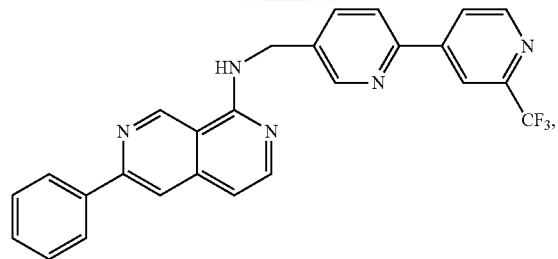
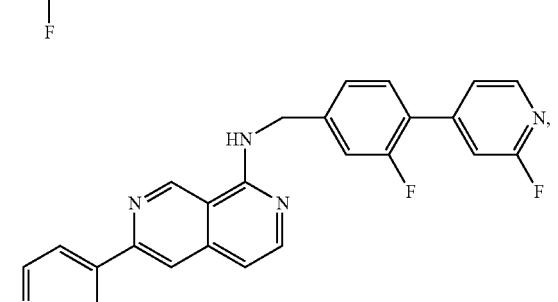
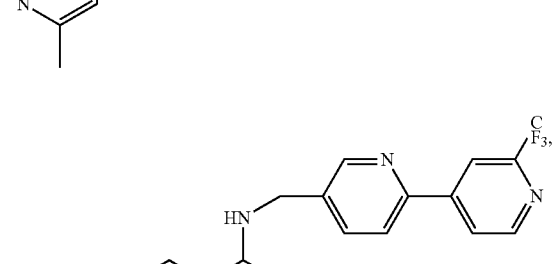
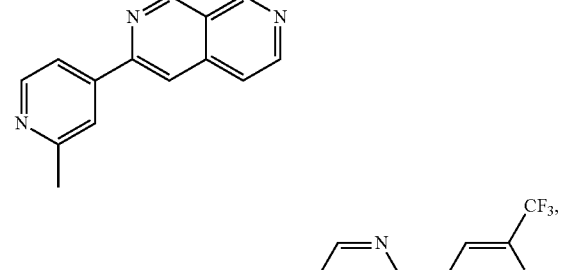
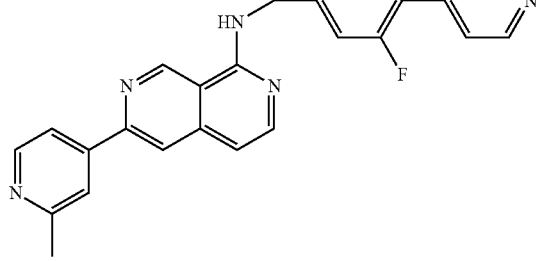
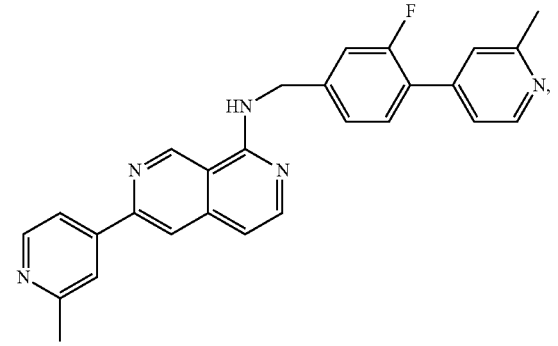

87
-continued
88
-continued
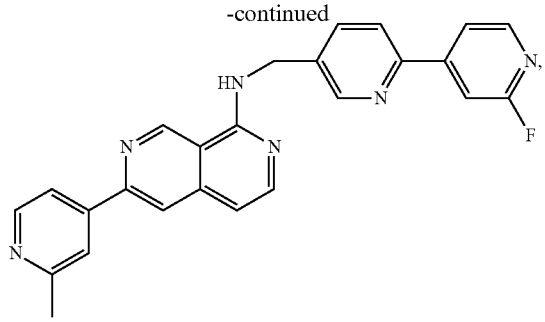
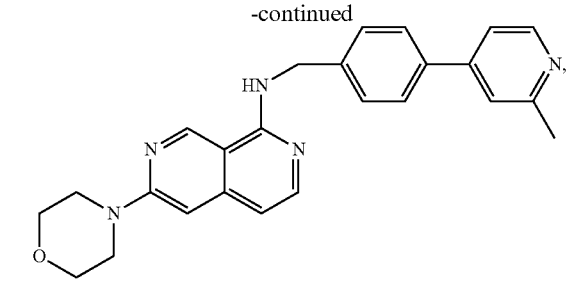

89
-continued
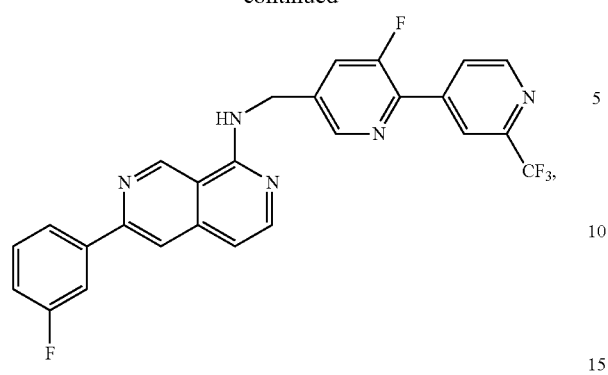
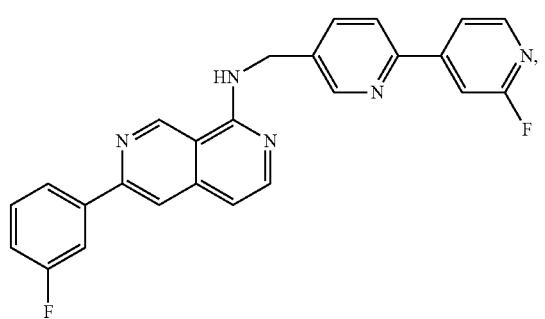
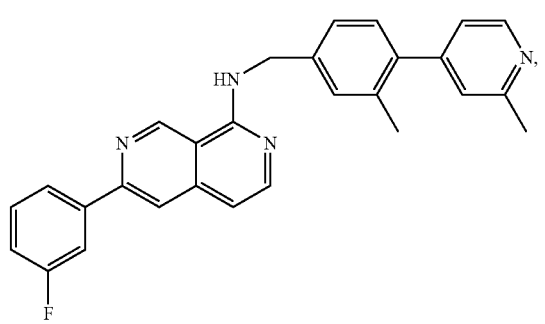
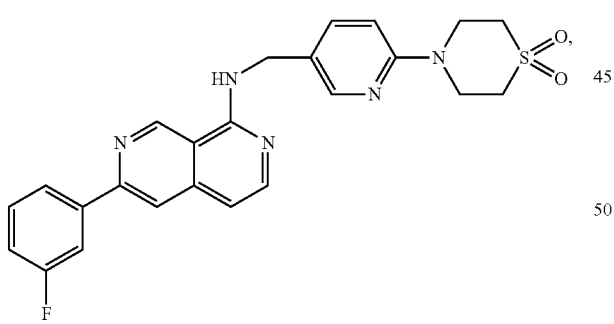
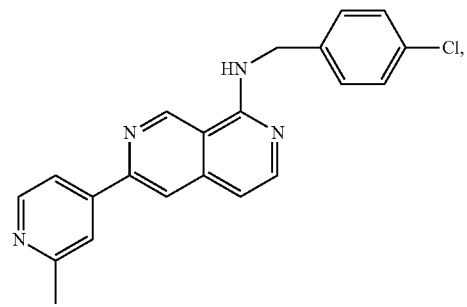
90
-continued
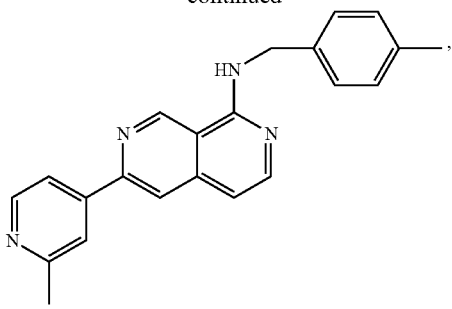
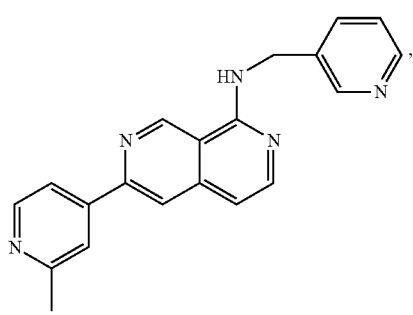
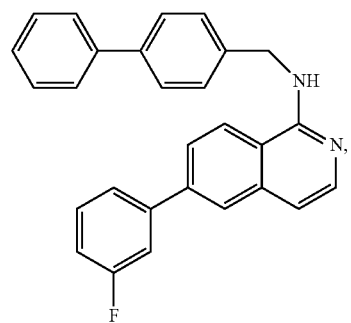
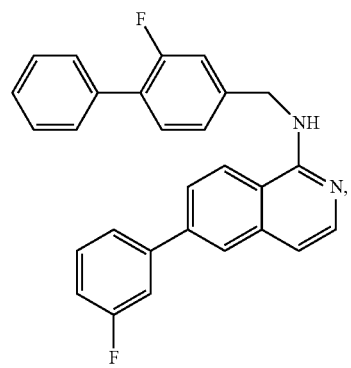
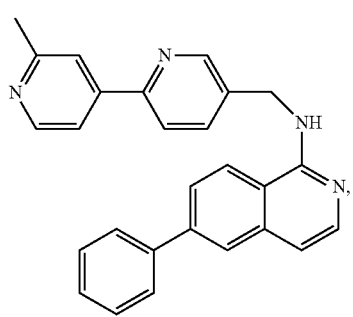

91
-continued
92
-continued
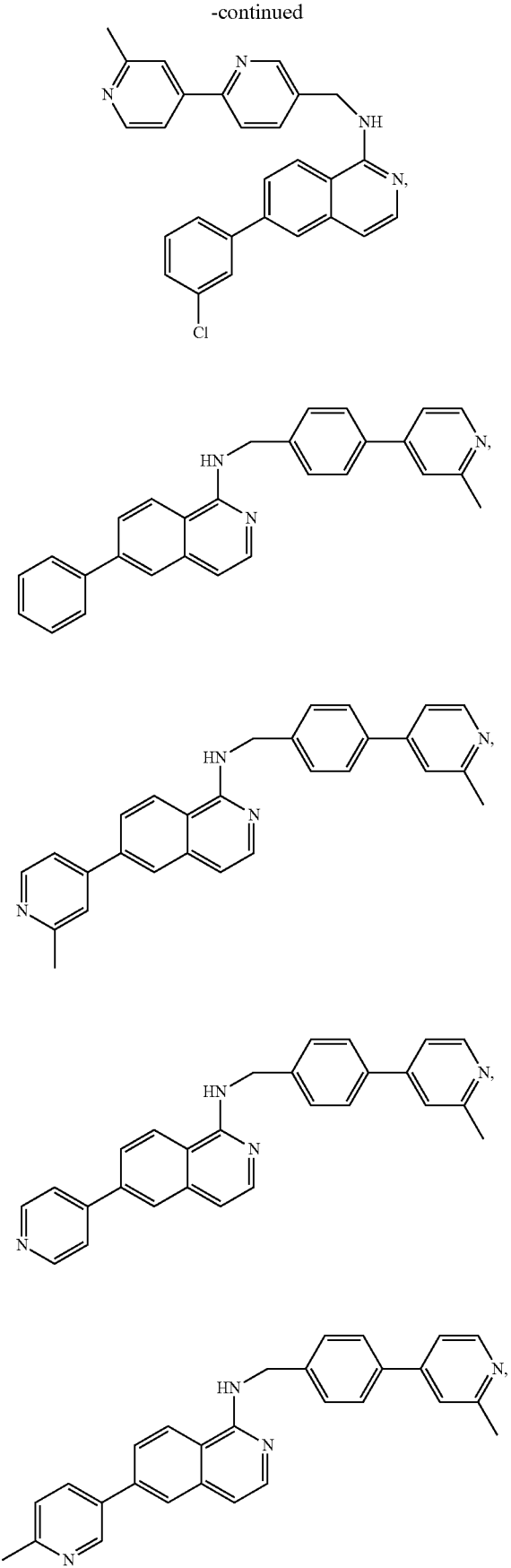
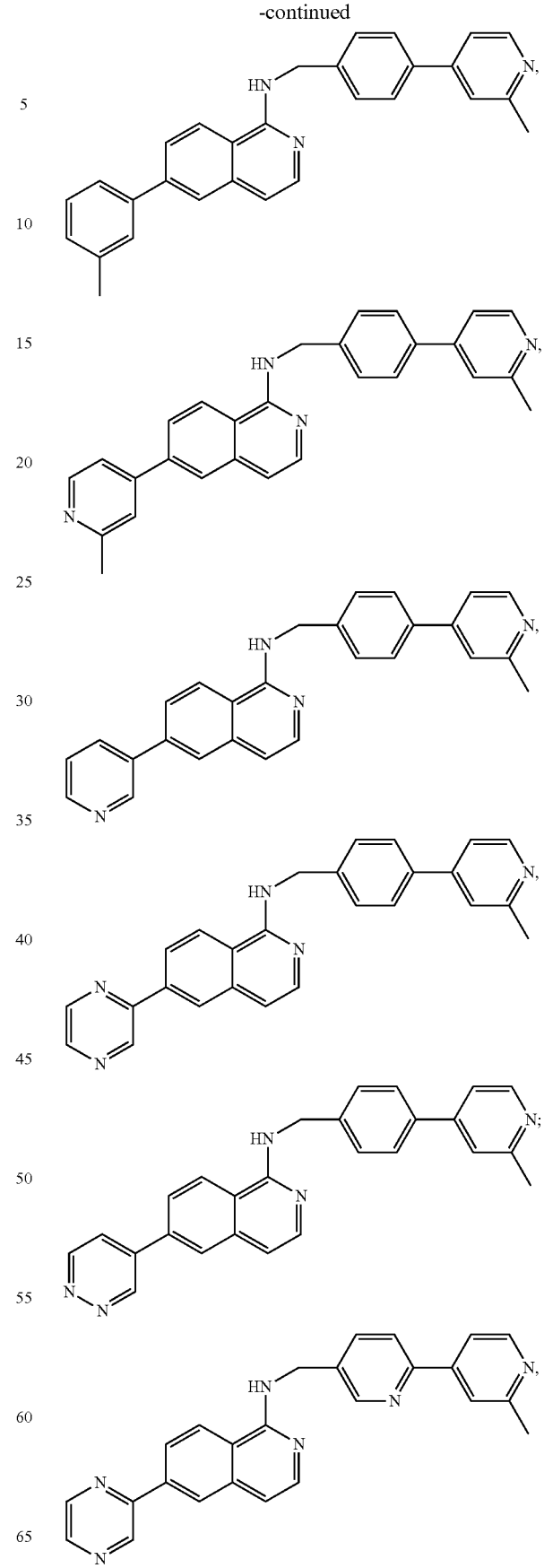

93
-continued
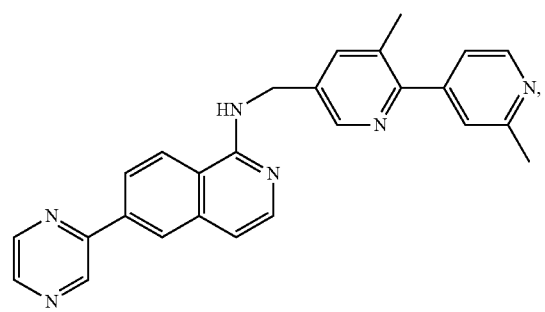
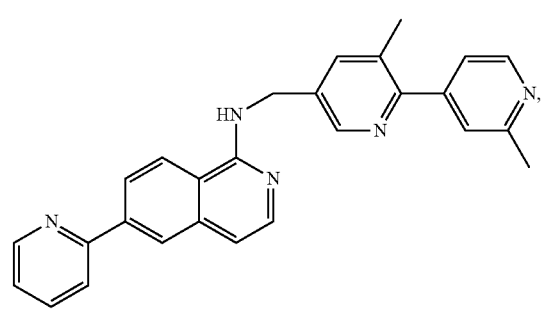
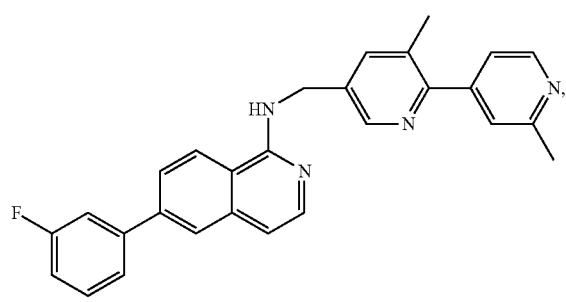
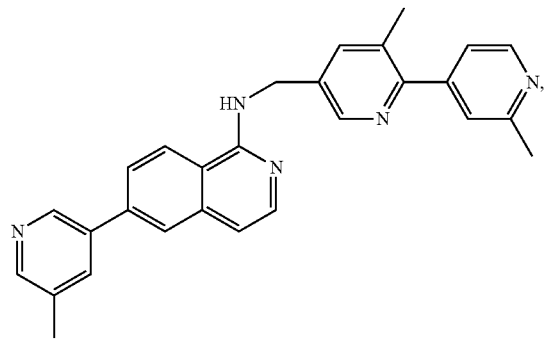
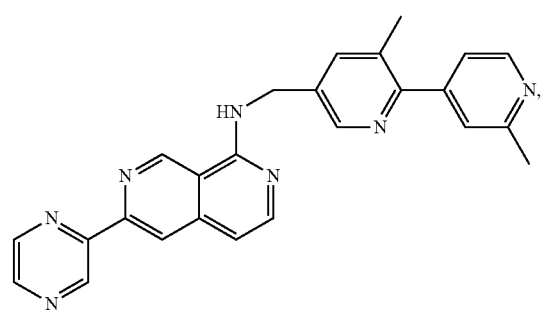
94
-continued
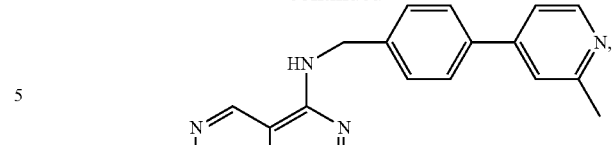
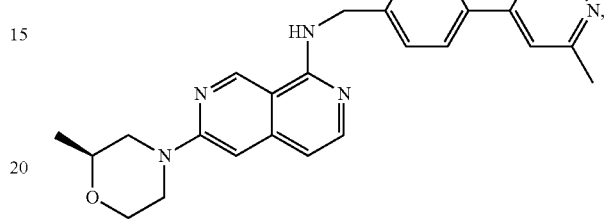
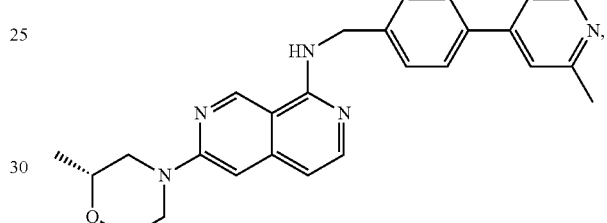
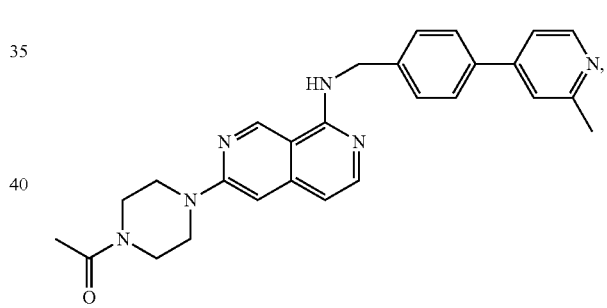
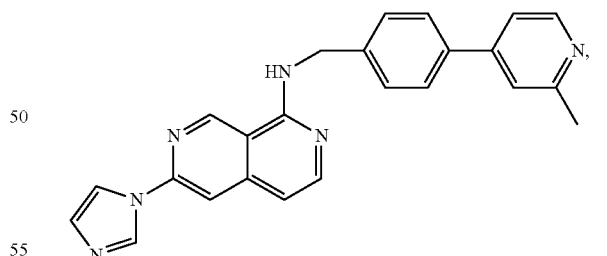
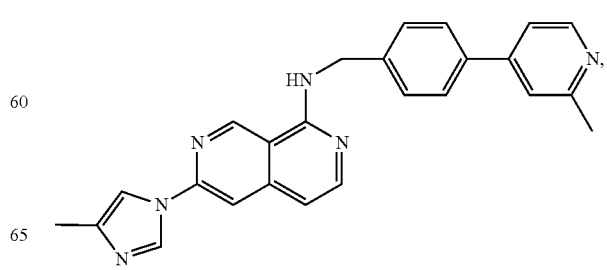

95
-continued
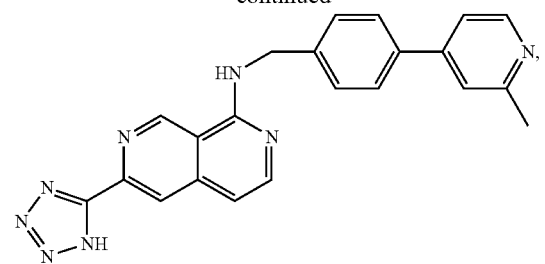
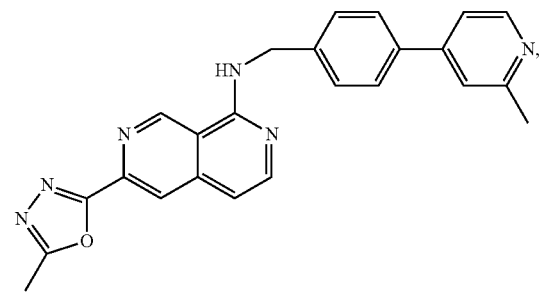
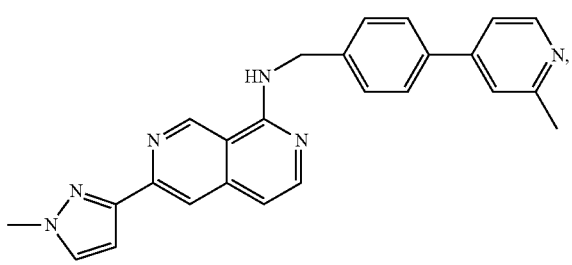
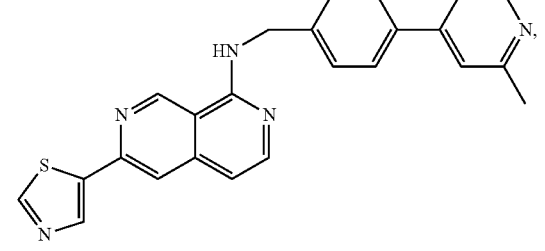
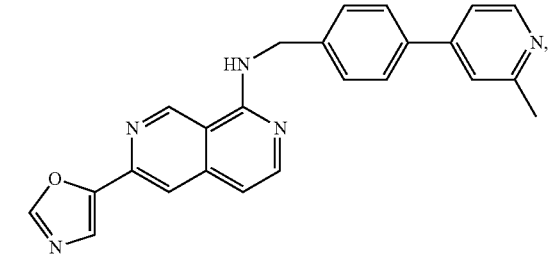
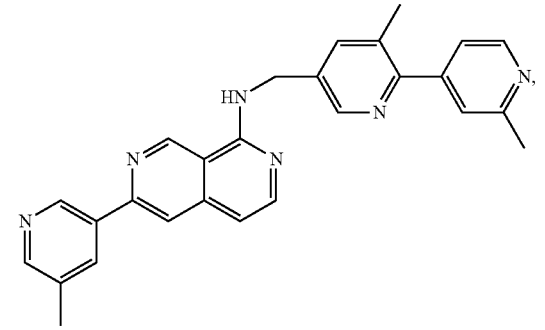
96
-continued
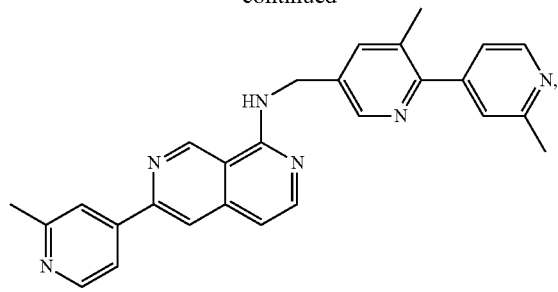
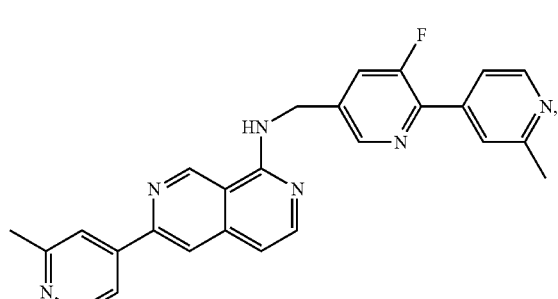
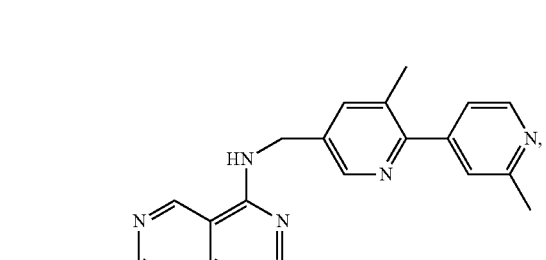
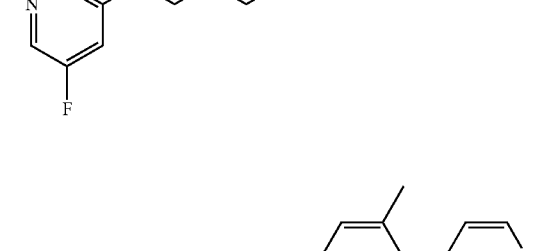
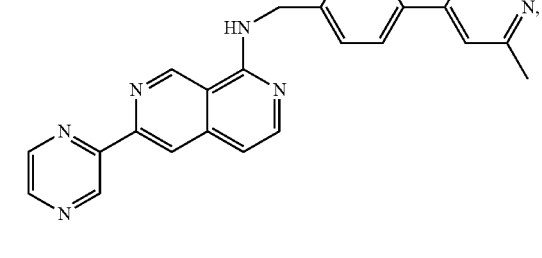
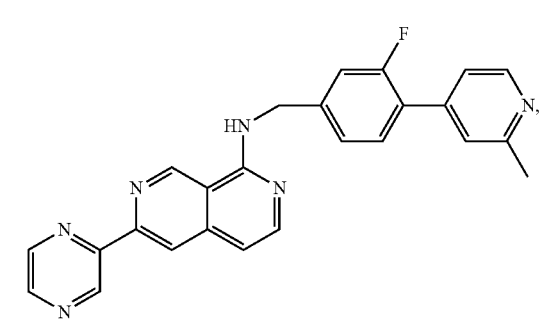

-continued

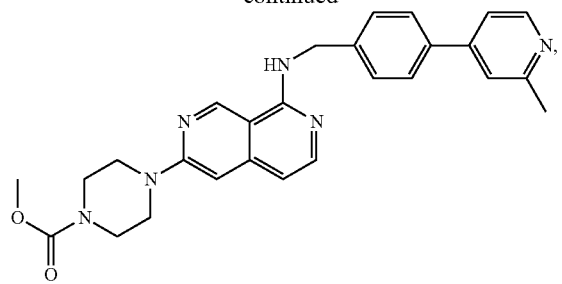

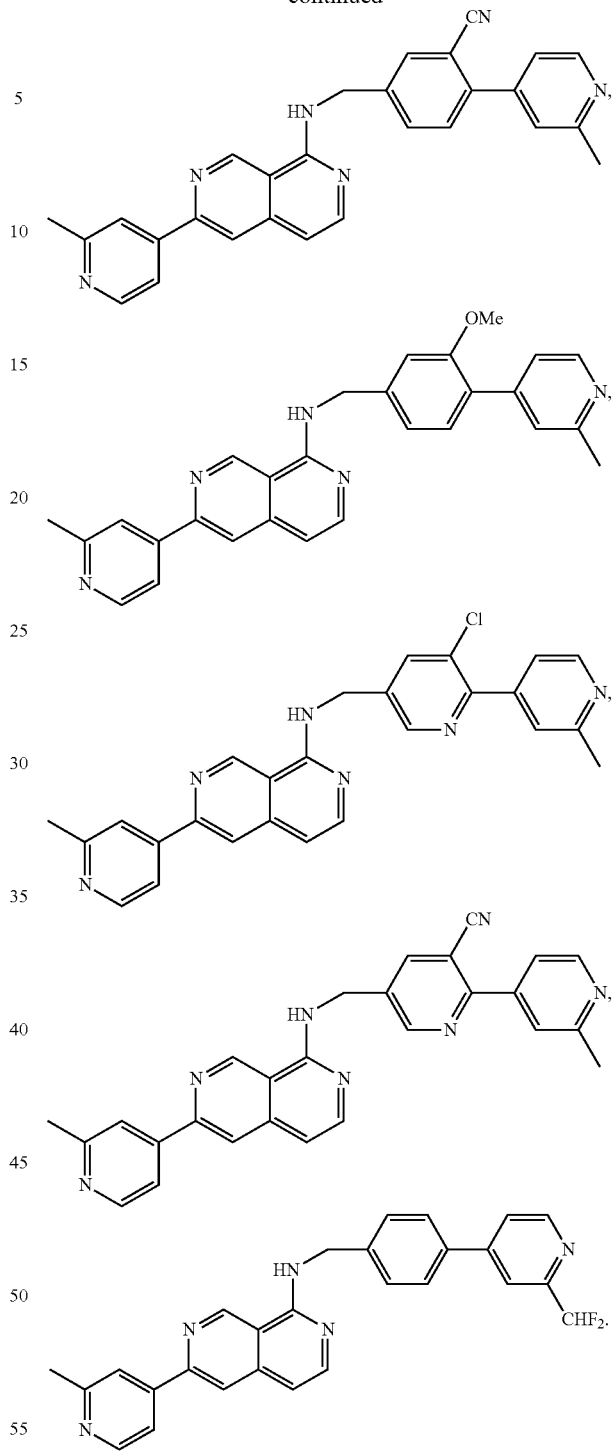

8. A pharmaceutical composition comprising the compound or physiologically acceptable salt thereof of claim 1.

9. The pharmaceutical composition of claim 8 that is an oral composition, an injectable composition or a suppository.

10. A method of inhibiting WNT secretion from a cell, comprising contacting the cell with an effective amount of the compound or physiologically acceptable salt thereof of claim 1.

11. A method of inhibiting WNT signaling in a cell, comprising contacting the cell with an effective amount of the compound or physiologically acceptable salt thereof of claim 1.

12. A method for treating colorectal cancer in a subject suffering therefrom, comprising administering to the subject a therapeutically effective amount of the compound or physiologically acceptable salt thereof of claim 1.

13. The method of claim 12, wherein the therapeutically effective amount is about 0.03 to 2.5 mg/kg per body weight at daily dosages.

14. The method of claim 13, wherein the therapeutically effective amount is about 0.5 mg to 1000 mg for humans.

15. The method of claim 12, wherein the compound is administrated enterally, orally, parenterally, topically or in a nasal or suppository form.

16. The compound of claim 1, having the core structure of:

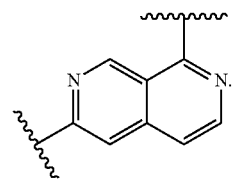 [SMILES: *c1cc2ccnc(*)c2cn1]

17. A method of inhibiting WNT secretion from a cell, comprising contacting the cell with an effective amount of the pharmaceutical composition of claim 8.

18. A method of inhibiting WNT signaling in a cell, comprising contacting the cell with an effective amount of the pharmaceutical composition of claim 8.

19. A method for treating colorectal cancer in a subject suffering therefrom, comprising administering to the subject a therapeutically effective amount of the pharmaceutical composition of claim 8.

* * * * *